United States Patent
Hsieh-Wilson et al.

(10) Patent No.: US 9,645,151 B2
(45) Date of Patent: May 9, 2017

(54) TARGETING PHOSPHOFRUCTOKINASE AND ITS GLYCOSYLATION FORM FOR CANCER

(71) Applicant: California Institute of Technology, Pasadena, CA (US)

(72) Inventors: Linda C. Hsieh-Wilson, South Pasadena, CA (US); Wen Yi, Hangzhou (CN)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/417,889

(22) PCT Filed: Aug. 19, 2013

(86) PCT No.: PCT/US2013/055606
§ 371 (c)(1),
(2) Date: Jan. 28, 2015

(87) PCT Pub. No.: WO2014/028939
PCT Pub. Date: Feb. 20, 2014

(65) Prior Publication Data
US 2015/0369809 A1 Dec. 24, 2015

Related U.S. Application Data

(60) Provisional application No. 61/684,549, filed on Aug. 17, 2012.

(51) Int. Cl.
*G01N 33/574* (2006.01)
*C07K 16/40* (2006.01)

(52) U.S. Cl.
CPC ....... *G01N 33/57423* (2013.01); *C07K 16/40* (2013.01); *G01N 33/574* (2013.01); *C07K 2317/21* (2013.01); *C07K 2317/24* (2013.01); *C07K 2317/34* (2013.01); *G01N 2333/912* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,225,539 A | 7/1993 | Winter |
| 5,292,658 A | 3/1994 | Cormier et al. |
| 5,418,155 A | 5/1995 | Cormier et al. |
| 5,464,758 A | 11/1995 | Gossen et al. |
| 5,484,892 A | 1/1996 | Tedder et al. |
| 5,530,101 A | 6/1996 | Queen et al. |
| 5,585,089 A | 12/1996 | Queen et al. |
| 5,585,097 A | 12/1996 | Bolt et al. |
| 5,589,362 A | 12/1996 | Bujard et al. |
| 5,631,146 A | 5/1997 | Szostak et al. |
| 5,650,298 A | 7/1997 | Bujard et al. |
| 5,683,888 A | 11/1997 | Campbell |
| 5,691,145 A | 11/1997 | Pitner et al. |
| 5,693,761 A | 12/1997 | Queen et al. |
| 5,693,762 A | 12/1997 | Queen et al. |
| 5,728,851 A | 3/1998 | Frankie |
| 5,741,668 A | 4/1998 | Ward et al. |
| 5,777,079 A | 7/1998 | Tsien et al. |
| 5,804,387 A | 9/1998 | Cormack et al. |
| 5,821,337 A | 10/1998 | Carter et al. |
| 5,846,534 A | 12/1998 | Waldmann et al. |
| 5,859,205 A | 1/1999 | Adair et al. |
| 5,874,304 A | 2/1999 | Zolotukhin et al. |
| 5,876,995 A | 3/1999 | Bryan |
| 5,925,558 A | 7/1999 | Tsien et al. |
| 6,054,297 A | 4/2000 | Carter et al. |
| 6,057,153 A | 5/2000 | George et al. |
| 6,180,370 B1 | 1/2001 | Queen et al. |
| 6,313,373 B1 | 11/2001 | Eckert et al. |
| 6,407,213 B1 | 6/2002 | Carter et al. |
| 6,491,916 B1 | 12/2002 | Bluestone et al. |
| 6,966,424 B2 | 11/2005 | Cram |
| 6,982,321 B2 | 1/2006 | Winter |
| 7,405,227 B2 | 7/2008 | Kun et al. |
| 2003/0108548 A1 | 6/2003 | Bluestone et al. |
| 2004/0006216 A1 | 1/2004 | Waldmann et al. |
| 2004/0166099 A1 | 8/2004 | Rao |
| 2006/0002921 A1 | 1/2006 | Winsor-Hines et al. |

(Continued)

FOREIGN PATENT DOCUMENTS

| WO | WO 92/01047 A1 | 1/1992 |
|---|---|---|
| WO | WO 92/15673 A1 | 9/1992 |

(Continued)

OTHER PUBLICATIONS

Šmerc et al. (PLoS ONE May 2011 6(5): e19645).*
Hsieh-Wilson, L (FASEB J. Meeting Info.: Joint Annual Meeting of the ASPET/BPS at Experimental Biology, Apr. 20-24, 2013).*
Macmillan Dictionary (Kit, http://www.macmillandictionary.com/dictionary/american/kit, retrieved Aug. 23, 2013).*
Santa Cruz Biotechnology (PKF-1 (G-11): SC-166722, Dec. 7, 2010).*
Wang et al. (245th ACS National Meeting Exposition Apr. 7-11, 2013, CARB-71).*
Yi et al. (Glycoconjugate Journal May 2013 30(4): 292, Abs. No. 012).*
Adang, et al. The reconstruction and expression of a *Bacillus thuringiensis* cryIIIA gene in protoplasts and potato plants. Plant Mol Biol. Mar. 1993;21(6):1131-45.
Armitage, et al. Molecular and biological characterization of a murine ligand for CD40. Nature. May 7, 1992;357(6373):80-2.
Ausubel, et al. Current Protocols in Molecular Biology, 1987.
Ausubel, et al. Short Protocols in Molecular Biology. 3rd Edition, John Wiley and Sons, 1999.

(Continued)

*Primary Examiner* — Peter J Reddig
(74) *Attorney, Agent, or Firm* — Wilson Sonsini Goodrich & Rosati

(57) ABSTRACT

The present invention relates to methods of treating cancer, suppressing or inhibiting tumorigenesis, tumor growth or cancer progression, and suppressing or inhibiting cancer cells from altering cellular metabolism in favor of cancerous growth. Also provided are compositions comprising an agent that decreases glycosylation of phosphofructokinase 1 or increases phosphofructokinase 1 expression or activity.

9 Claims, 29 Drawing Sheets

(56) References Cited

U.S. PATENT DOCUMENTS

| | | | |
|---|---|---|---|
| 2011/0136201 A1 | 6/2011 | Mao et al. | |
| 2012/0039811 A1* | 2/2012 | Admon | A61K 39/0011 424/9.1 |

FOREIGN PATENT DOCUMENTS

| | | |
|---|---|---|
| WO | WO 95/07463 A1 | 3/1995 |
| WO | WO 98/14605 A1 | 4/1998 |
| WO | WO 98/26277 A2 | 6/1998 |
| WO | WO 99/49019 A2 | 9/1999 |
| WO | WO 01/23426 A2 | 4/2001 |
| WO | WO 2012/065139 A2 | 5/2012 |

OTHER PUBLICATIONS

Baines, et al. Purification of immunoglobulin g (IgG). Methods Mol Biol. 1992;10:79-104. doi: 10.1385/0-89603-204-3:79.

Bambot, et al. Efficient total gene synthesis of 1.35-kb hybrid alpha-lytic protease gene using the polymerase chain reaction. PCR Methods Appl. Feb. 1993;2(3):266-71.

Bitter, et al. Expression and secretion vectors for yeast. Methods Enzymol. 1987;153:516-44.

Bruggemann, et al. Production of human antibody repertoires in transgenic mice. Curr Opin Biotechnol. Aug. 1997;8(4):455-8.

Cairns, et al. Regulation of cancer cell metabolism. Nat Rev Cancer. Feb. 2011;11(2):85-95. doi: 10.1038/nrc2981.

Caldwell, et al. Nutrient sensor O-GlcNAc transferase regulates breast cancer tumorigenesis through targeting of the oncogenic transcription factor FoxM1. Oncogene. May 13, 2010;29(19):2831-42. doi: 10.1038/onc.2010.41. Epub Mar. 1, 2010.

Carter, et al. Humanization of an anti-p185HER2 antibody for human cancer therapy. Proc Natl Acad Sci U S A. May 15, 1992;89(10):4285-9.

Chalfie, et al. Green fluorescent protein as a marker for gene expression. Science. Feb. 11, 1994;263(5148):802-5.

Chen, et al. TiProD: the Tissue-specific Promoter Database. Nucleic Acids Res. Jan. 1, 2006;34(Database issue):D104-7.

Clark. Antibody humanization: a case of the 'Emperor's new clothes'? Immunol Today. Aug. 2000;21(8):397-402.

Coligan, et al. Current Protocols in Immunology. John Wiley and Sons, 1991.

Deng, et al. Phosphorylation of bad at Thr-201 by JNK1 promotes gycolysis through activation of phosphofructokinase-1. J Biol Chem, Jul. 25, 2008, vol. 283, No. 30, pp. 20754-20760, entire document.

Dillon, et al. Use of polymerase chain reaction for the rapid construction of synthetic genes. Methods Mol Biol. 1993;15:263-8. doi: 10.1385/0-89603-244-2:263.

Dube, et al. Glycans in cancer and inflammation—potential for therapeutics and diagnostics. Nat Rev Drug Discov, Jun. 2005, vol. 4, No. 6, pp. 477-488, entire document.

Eglitis, et al. Retroviral vectors for introduction of genes into mammalian cells. Biotechniques. Jul.-Aug. 1988;6(7):608-14.

Fang, et al. The ER UDPase ENTPD5 promotes protein N-glycosylation, the warburg effect, and proliferation in the PTEN pathway. Cell, Nov. 24, 2010, vol. 143, No. 5, pp. 711-724, entire document.

Frauwirth, et al. Regulation of T lymphocyte metabolism. The Jounral of Immunology, Apr. 15, 2004, vol. 172, No. 8, pp. 4661-4665, entire document.

Freshney. Culture of Animal Cells: A Manual of Basic Technique, 1987.

GenBank Accession No. U55762, pEGFP-N1 Vector Information. Gene 173 (1 SPEC NO), 33-38 (1996).

Gold, et al. Diversity of oligonucleotide functions. Annu Rev Biochem. 1995;64:763-97.

Gossen, et al. Tight control of gene expression in mammalian cells by tetracycline-responsive promoters. Proc Natl Acad Sci U S A. Jun. 15, 1992;89(12):5547-51.

Griffiths, et al. Strategies for selection of antibodies by phage display. Curr Opin Biotechnol. Feb. 1998;9(1):102-8.

Haller, et al. In vitro selection of a 7-methyl-guanosine binding RNA that inhibits translation of capped mRNA molecules. Proc Natl Acad Sci U S A. Aug. 5, 1997;94(16):8521-6.

Harlow, et al. Antibodies: A Laboratory Manual, 1988.

Hart, et al. Cycling of O-linked-N-acetylglucosamine on nucleocytoplasmic proteins. Nature, Apr. 26, 2007, vol. 446, No. 7139, pp. 1017-1022, entire document.

Heim, et al. Engineering green fluorescent protein for improved brightness, longer wavelengths and fluorescence resonance energy transfer. Curr Biol. Feb. 1, 1996;6(2):178-82.

Hue, et al. Role of fructose 2,6-biphosphate in the control of glycolysis in mammalian tissues. Biochem. J, Jul. 15, 1987, vol. 245, No. 2,313-324, entire document.

Ichiki, et al. Regulation of the expression of human C epsilon germline transcript. Identification of a novel IL-4 responsive element. J Immunol. Jun. 15, 1993;150(12):5408-17.

International search report dated Jan. 30, 2014 for PCT/US2013/055606.

Jones, et al. Replacing the complementarity-determining regions in a human antibody with those from a mouse. Nature. May 29-Jun. 4, 1986;321(6069):522-5.

Kang, et al. O-GlcNAc protein modification in cancer cells increases in response to glucose deprivation through glycogen degradation. J Biol Chem, Dec. 11, 2009, vol. 284, No. 50, pp. 34777-34784, entire document.

Kaufman, et al. Amplification and expression of sequences cotransfected with a modular dihydrofolate reductase complementary dna gene. J Mol Biol. Aug. 25, 1982;159(4):601-21.

Levine, et al. The control of the metabolic switch in cancers by oncogenes and tumor suppressor genes. Science. Dec. 3, 2010;330(6009):1340-4. doi: 10.1126/science.1193494.

Lynch, et al. Critical role of O-Linked β-N-acetylglucosamine transferase in prostate cancer invasion, angiogenesis, and metastasis. J Biol Chem. Mar. 30, 2012;287(14):11070-81. doi: 10.1074/jbc.M111.302547. Epub Jan. 24, 2012.

Mattaini, et al. Cancer glycosylation to adapt to stress. Science, Aug. 24, 2012, vol. 337, No. 6097, pp. 925-926, entire document.

McPherson, et al. Methods in Enzymology: PCR 2: A Practical Approach. Academic Press, 1995.

Nolan, et al. Fluorescence-activated cell analysis and sorting of viable mammalian cells based on beta-D-galactosidase activity after transduction of *Escherichia coli* lacZ. Proc Natl Acad Sci U S A. Apr. 1988;85(8):2603-7.

O'Connor, et al. Humanization of an antibody against human protein C and calcium-dependence involving framework residues. Protein Eng. Apr. 1998;11(4):321-8.

Pathania, et al. Opportunities in discovery and delivery of anticancer drugs targeting mitochondria and cancer cell metabolism. Advanced Drug Delivery Reviews, Nov. 30, 2009, vol. 61, No. 14, pp. 1250-1275, entire document.

Possemato, et al. Functional genomics reveal that the serine synthesis pathway is essential in breast cancer. Nature. Aug. 18, 2011;476(7360):346-50. doi: 10.1038/nature10350.

Queen, et al. A humanized antibody that binds to the interleukin 2 receptor. Proc Natl Acad Sci U S A. Dec. 1989;86(24):10029-33.

Remington's Pharmaceutical Sicences. 18th Edition, 1990.

Riechmann, et al. Reshaping human antibodies for therapy. Nature. Mar. 24, 1988;332(6162):323-7.

Sambrook, et al. Molecular Cloning: A Laboratory Manual. 2nd Edition, 1989.

Scahill, et al. Expression and characterization of the product of a human immune interferon cDNA gene in Chinese hamster ovary cells. Proc Natl Acad Sci U S A. Aug. 1983;80(15):4654-8.

Sidorenko, et al. Comparison of metabolic flux distributions for MDCK cell growth in glutamine- and pyruvate-containing media. Biotechnol Prog. Mar.-Apr. 2008;24(2):311-20. doi: 10.1021/bp0702673. Epub Jan. 24, 2008.

Slawson, et al. O-GlcNAc signalling: implications for cancer cell biology. Nat Rev Cancer. Aug. 18, 2011;11(9):678-84. doi: 10.1038/nrc3114.

(56) References Cited

OTHER PUBLICATIONS

Sola-Penna, et al. Regulation of mammalian muscle type 6-phosphofructo-1-kinase and its implication for the control of the metabolism. IUBMB Life. Nov. 2010;62(11):791-6. doi: 10.1002/iub.393.

Southern, et al. Transformation of mammalian cells to antibiotic resistance with a bacterial gene under control of the SV40 early region promoter. J Mol Appl Genet. 1982;1(4):327-41.

Stauber, et al. Development and applications of enhanced green fluorescent protein mutants. Biotechniques. Mar. 1998;24(3):462-6, 468-71.

Steinberg. Protein gel staining methods: an introduction and overview. Methods Enzymol. 2009;463:541-63. doi: 10.1016/S0076-6879(09)63031-7.

Su, et al. Human H+ ATPase a4 subunit mutations cuasing renal tubular acidosis reveal a role for interaction with phosphofructokinase-1. Am J Physiol, Oct. 2008, vol. 295, No. 4, pp. F950-F958, entire document.

Subramani, et al. Expression of the mouse dihydrofolate reductase complementary deoxyribonucleic acid in simian virus 40 vectors. Mol Cell Biol. Sep. 1981;1(9):854-64.

Taylor, et al. Glucose deprivation stimulates O-GlcNAc modification of proteins through up-regulation of O-linked N-acetylglucosaminyltransferase. J Biol Chem. Mar. 7, 2008;283(10):6050-7. doi: 10.1074/jbc.M707328200. Epub Jan. 3, 2008.

Urbano, et al. Effects of overexpression of the liver subunit of 6-phosphofructo-1-kinase on the metabolism of a culture mammalian cell line. Biochem J, Dec. 15, 2000, vol. 352, Pt. 3, pp. 921-927, entire document.

Urlaub, et al. Isolation of Chinese hamster cell mutants deficient in dihydrofolate reductase activity. Proc Natl Acad Sci U S A. Jul. 1980;77(7):4216-20.

Vander-Heiden, et al. Understanding the Warburg effect: the metabolic requirements of cell proliferation. Science. May 22, 2009;324(5930):1029-33. doi: 10.1126/science.1160809.

Verhoeyen, et al. Reshaping human antibodies: grafting an antilysozyme activity. Science. Mar. 25, 1988;239(4847):1534-6.

Wang, et al. A DNA aptamer which binds to and inhibits thrombin exhibits a new structural motif for DNA. Biochemistry. Mar. 2, 1993;32(8):1899-904.

Wilson, et al. A cloning of the B cell membrane protein CD22: a mediator of B—B cell interactions. J Exp Med. Jan. 1, 1991;173(1):137-46.

Wilson, et al. Genomic structure and chromosomal mapping of the human CD22 gene. J Immunol Jun. 1, 1993;150(11):5013-24.

Wu, et al. Receptor-mediated in vitro gene transformation by a soluble DNA carrier system. J Biol Chem. Apr. 5, 1987;262(10):4429-32.

Yi, et al. Phosphofructokinase 1 glycosylation regulatres cell growth and metabolism. Science, Aug. 24, 2012, vol. 337, No. 6097, pp. 975-980, entire document.

\* cited by examiner

C

D

B

| | | |
|---|---|---|
| Homo sapiens | IVMCVIPATISNNVPGTDF | 537 |
| Rattus norvegicus | IPFVVIPATVSNNVPGSDF | 538 |
| Mus musculus | IVMCVIPATISNNVPGTDF | 537 |
| Cricetulus griseus | IVMCVIPATISNNVPGTDF | 506 |
| Macaca fascicularis | IPFVVIPATVSNNVPGSDF | 538 |
| Pongo abelii | IPFVVIPATVSNNVPGSDF | 538 |
| Nomascus leucogenys | IPFVVIPATVSNNVPGSDF | 538 |
| Danio rerio | IPMVIIPATVSNNVPGSDF | 539 |
| Drosophila melanogaster | IPIVVIPSTISNNVPGTEF | 547 |
| Saccharomyces cerevisiae | IPMCLIPATVSNNVPGTEY | 532 |
| Pichia pastoris | IPMCCLPATVSNNVPGTEY | 737 |

C

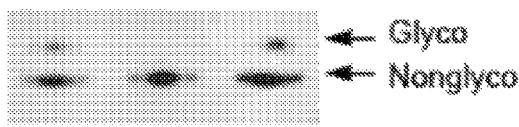

TARGETING PHOSPHOFRUCTOKINASE AND ITS GLYCOSYLATION FORM FOR CANCER

CROSS-REFERENCE

This application is a National Stage Entry of International Patent Application No. PCT/US2013/055606, filed on Aug. 19, 2013, which claims the benefit under 35 USC §119(e) of U.S. Provisional Application No. 61/684,549, filed on Aug. 17, 2012, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 5, 2013, is named 38075-717.601_SL.txt and is 20,597 bytes in size.

STATEMENT AS TO FEDERALLY SPONSORED RESEARCH

This invention was made with government support under R01 GM084724 awarded by the National Institutes of Health. The government has certain rights in the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Cancer cells have developed highly regulated processes to meet the metabolic demands of rapid cell growth. Unlike normal cells, which utilize mitochondrial oxidative phosphorylation to generate ATP needed for cellular processes, most cancer cells instead rely on aerobic glycolysis for ATP generation even under aerobic conditions. (Heiden et al., Science 324, 1029 (2009)). Further, cancer cells alter the metabolism of major classes of macromolecules, including carbohydrates, lipids and nucleic acids, to increase biosynthesis of macromolecules and maintain redox homeostasis. (Cairns et al., Nature Reviews Cancer 11, 85-95 (2011)). These altered cellular metabolisms allow cancer cells to grow and reproduce within a stressful and dynamic microenvironment that would otherwise have blocked proliferation.

Cancer cells acquire the altered metabolic phenotypes partially through genetic alterations in oncogenes and tumor suppressor genes involved in many key cancer-producing pathways. (Levine et al., Science 330, 1340 (2010)). In addition, dysregulation of posttranslational modifications such as protein phosphorylation and glycosylation also contributes to the metabolic reprogramming of cancer cells. (Slawson et al., Nature Reviews Cancer 11, 678-684 (2011)). Posttranslational modifications are rapid and reversible, and have emerged as critical contributing factors for tumor growth.

Glycosylation of proteins with O-linked β-N-acetylglucosamine (O-GlcNAcylation) is one way of posttranslational modification, which serves as a crucial mechanism for cells to respond to various stimuli, and couples nutrient status and cellular metabolism to the regulation of critical signaling pathways. (Hart et al., Nature 446, 1017 (2007)). O-GlcNAc transferase (OGT) catalyzes the covalent attachment of β-D-N-acetylglucosamine (GlcNAc) sugars to serine or threonine residues of many cytoplasmic proteins important for cancer-relevant processes. Alteration in O-GlcNAcylation allows the cancer cell to evade the cell cycle checkpoint controls and acquire adaptability to the local environment. (Slawson et al., Nature Reviews Cancer 11, 678-684 (2011)). Indeed, OGT and O-GlcNAcylation are elevated in multiple cancer types and reducing OGT levels blocks breast cancer growth and prostate cancer metastasis. (Caldwell et al., Oncogene 29, 2831-2842 (2010); Lynch et al., J. Biol. Chem., 287, 11070 (2012)).

There is a need to develop effective cancer therapeutics targeting the metabolic dependencies of cancer cells. While current treatment such as surgery, radiation, and chemotherapy, alone or in combination, has achieved some limited success, effective treatment of cancer remains a major challenge to modern medicine.

BRIEF SUMMARY OF THE INVENTION

Strategies that restore altered metabolic pathways in cancer cells by modifying glycosylation of proteins can provide a new avenue to combat cancer. The present invention provides compositions and methods directed to cancer treatment. The findings disclosed herein demonstrate cancer cell growth and metabolism are regulated by Phosphofructokinase 1 glycosylation.

One aspect of the invention is a method of detecting a cancer tissue. The method comprises (a) providing a sample of a subject; (b) detecting a level of glycosylated phosphofructokinase 1 (PFK-1) by performing a binding assay with a binding agent that specifically binds PFK-1, said assay yielding a detectable signal indicative of said level of glycosylated PFK-1; (c) designating the sample as cancerous if the detected level of glycosylated PFK-1 in the sample is at least 1.5 times a baseline level of glycosylated PFK-1 in a non-cancerous control sample. Optionally, the method further comprises (d) reporting the result of step (c) to a designated person or entity. In some embodiments, the binding assay comprises (a) isolating glycosylated proteins from other proteins in the sample, and contacting the isolated proteins with the binding agent; or (b) contacting protein derived from the sample with the binding agent, and further wherein the binding agent specifically binds glycosylated PFK-1. In some embodiments, designating the sample as cancerous further comprises designating a stage of cancer progression. In some embodiments, the sample is designated as early stage cancer if the detected level of glycosylated PFK-1 in the sample is between 1.5-3 times a baseline level of glycosylated PFK-1 in a non-cancerous control sample. In some embodiments, the sample is designated as late-stage cancer if the detected level of glycosylated PFK-1 in the sample is at least 2.5 times a baseline level of glycosylated PFK-1 in a non-cancerous control sample. In some embodiments, the glycosylated PFK-1 comprises glycosylation at serine 529. In some embodiments, the binding agent in step (b) is an antibody. In some embodiments, the antibody has a target binding affinity ($K_D$) of 50 nM or less as measured by surface plasmon resonance at 37° C. In some embodiments, the cancer tissue is lung cancer tissue. In some embodiments, the lung cancer tissue is adenocarcinoma. Optionally, the method further comprises the step of administering a therapeutic agent based on the results of step (c). In some embodiments, therapeutic agent promotes deglycosylation of PFK-1, or inhibits glycosylation of PFK-1.

Also provided herein is a purified antibody, or antigen-binding antibody fragment thereof, directed specifically to glycosylated phosphofructokinase 1 (PFK-1). In some embodiments, the antibody is a monoclonal antibody. In some embodiments, the antibody is a humanized antibody. In some embodiments, the antibody is a human antibody. In some embodiments, the antibody binds an epitope comprising glycosylated serine 529 of PFK-1. In some embodiments, the antibody comprises a detectable label.

In another aspect, the present invention provides a kit for detecting glycosylated phosphofructokinase 1 (PFK-1) in a cancer tissue. The kit comprises (a) a purified antibody, or antigen-binding antibody fragment thereof, directed specifically to glycosylated phosphofructokinase 1 (PFK-1); and (b) instructions for use of the purified antibody, or antigen-binding antibody fragment thereof. In some embodiments, the antibody is a monoclonal antibody. In some embodiments, the antibody is a humanized antibody. In some embodiments, the antibody is a human antibody. In some embodiments, the antibody binds an epitope comprising glycosylated serine 529 of PFK-1.

In another aspect, the present invention provides a method of developing an anti-cancer agent that reduces phosphofructokinase 1 (PFK-1) glycosylation. The method comprises (a) contacting a cancer cell that expresses PFK-1 with a candidate agent; (b) detecting a reduction in PFK-1 glycosylation in the cell relative to a control cell; and (c) selecting the agent as a candidate that specifically reduces PFK-1 glycosylation if the level of PFK-1 glycosylation is reduced relative to the control cell. In some embodiments, the agent binds to serine 529 of PFK-1 and blocks glycosylation. In some embodiments, the agent binds to a site adjacent to serine 529 of PFK-1 thereby reducing glycosylation at serine 529. In some embodiments, the agent reduces activity or expression of O-GlcNAc transferase (OGT). In some embodiments, the agent enhances activity or expression of O-GlcNAcase (OGA). In some embodiments, the reduction of PFK-1 glycosylation is characterized by an increased glycolytic rate in the cell. In some embodiments, the reduction of PFK-1 glycosylation is characterized by an increased lactate production in the cell. In some embodiments, the reduction of PFK-1 glycosylation is characterized by a decreased pentose phosphate pathway (PPP) activity or a decreased pentose phosphate pathway (PPP) flux. In some embodiments, the reduction of PFK-1 glycosylation is characterized by a decreased NADPH level or GSH level. In some embodiments, the reduction of PFK-1 glycosylation is characterized by promotion of PFK-1 association into tetramers and higher oligomers. In some embodiments, the cancer cell is a lung cancer cell, an osteosarcoma cell, a breast cancer cell, a colon cancer cell, a gastric cancer cell, a pancreatic cancer cell, a prostate cancer cell or a melanoma cell. In some embodiments, the cancer cell is a lung cancer cell. In some embodiments, the agent is selected from the group consisting of an antisense oligonucleotide, peptide, an antibody, a liposome, a small interfering RNA, small organic compound and an inorganic compound. In some embodiments, detecting step involves an affinity-based assay. In some embodiments, the affinity-based assay is s an immunoassay or an enzyme-based assay.

The present invention further provides a method of reducing cancer formation or cancer progression. The method comprises administering to a cancer cell an effective amount of (i) a therapeutic anti-cancer agent identified by a method comprising: a) contacting a cancer cell that expresses PFK-1 with a candidate agent; and b) identifying the candidate agent as a therapeutic anti-cancer agent when the cell exhibits a decreased level of phosphofructokinase 1 (PFK-1) glycosylation relative to a control cell upon contacting said candidate agent; (ii) a therapeutic anti-cancer agent that specifically reduces glycosylation at serine 529 of PFK-1; or (iii) a therapeutic anti-cancer agent that binds to a site encompassing serine 529.

The present invention further provides a method of inducing cancer cell death. The method comprises contacting the cancer cell with an effective amount of (i) a therapeutic anti-cancer agent identified by a method comprising: a) contacting a cancer cell that expresses PFK-1 with a candidate agent; and b) identifying said candidate agent as a therapeutic anti-cancer agent when the cell exhibits a decreased level of phosphofructokinase 1 (PFK-1) glycosylation relative to a control cell upon contacting said candidate agent; (ii) a therapeutic anti-cancer agent that specifically reduces glycosylation at serine 529 of PFK-1; or (iii) a therapeutic anti-cancer agent that binds to a site encompassing serine 529.

The present invention further provides a method of reducing PFK-1 glycosylation at serine 529 in a cell. The method comprises contacting a cell with an agent that reduces glycosylation at serine 529.

The present invention further provides a method of increasing PFK-1 activity in a cell. The method comprises contacting the cell with an agent that reduces PFK-1 glycosylation thereby reducing PFK-1 activity.

In some embodiments, the therapeutic anti-cancer agent or the agent is an antibody or antigen-binding antibody fragment thereof. In some embodiments, the antibody or antigen-binding antibody fragment thereof specifically binds to an epitope comprising serine 529 of PFK-1. In some embodiments, the epitope comprising non-glycosylated serine 529. In some embodiments, the antibody or antigen-binding antibody fragment thereof binds to an epitope adjacent to non-glycosylated serine 529 of PFK-1 thereby reduces glycosylation at serine 529. In some embodiments, the antibody is a monoclonal antibody, a humanized antibody, or a human antibody.

In another aspect, the present invention provides a method of producing a modified PFK-1. The method comprises expressing a vector comprising polynucleotide encoding a PFK-1 in which amino acid 529 is not serine. In some embodiments, the modified PFK-1 has PFK-1 activity. In some embodiments, the mutation comprises a S529A substitution.

In yet another aspect, the present invention provides a modified phosphofructokinase 1 (PFK-1) protein comprising a mutation at serine 529. In some embodiments, the mutation is S529A. The present invention also provides a synthetic nucleic acid encoding the PFK-1 comprising a mutation at serine 529 or an isolated nucleic acid encoding the PFK-1 comprising a mutation at serine 529. The present invention further provides a vector encoding the modified phosphofructokinase 1 (PFK-1) protein comprising a mutation at serine 529, and a cell expressing the modified phosphofructokinase 1 (PFK-1) protein comprising a mutation at serine 529.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DEFINITIONS

Figure 1:
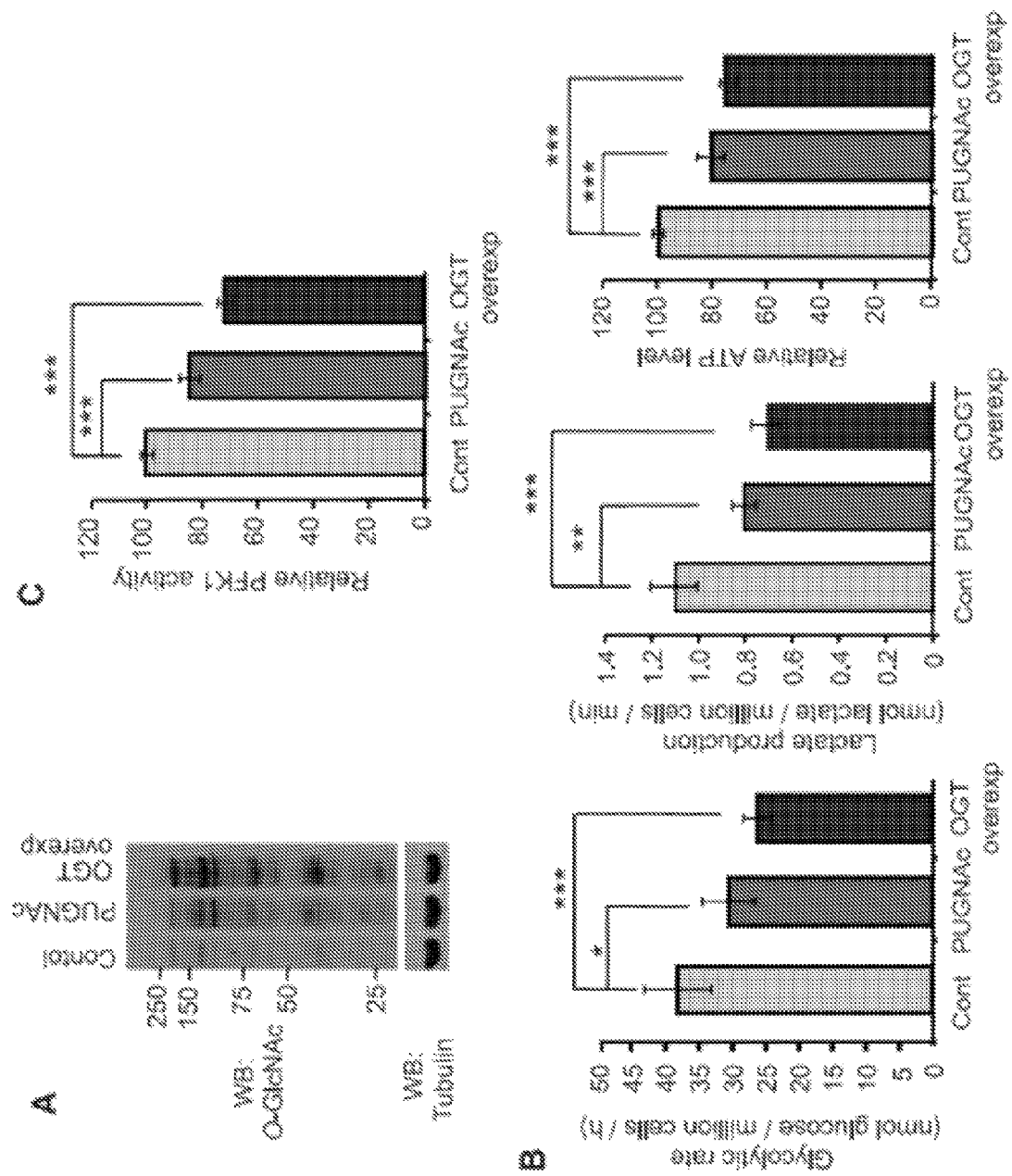
FIG. 1A shows results of an immunoblot for O-GlcNAc in control cells, cells treated with the OGA inhibitor PUG-NAc, and cells overexpressing OGT.
FIGS. 1B-C show bar graphs indicating effects of PUG-NAc treatment or OGT overexpression relative to controls.
FIG. 1D shows results of an immunoblot for PFK1 after treatment to purify glycosylated protein.
FIG. 1E shows results of an immunoblot for Flag-tagged PFK1, where glycosylated PFK1 was selectively labeled with a 5-kD PEG mass tag.
FIG. 1F shows results of an immunoblot illustrating induction of PFK1 glycosylation under hypoxic conditions.
FIG. 1G shows results of an immunoblot illustrating PFK1 glycosylation levels in human lung tumor (T) tissues compared to matched normal (N) tissues.
Figure 1:
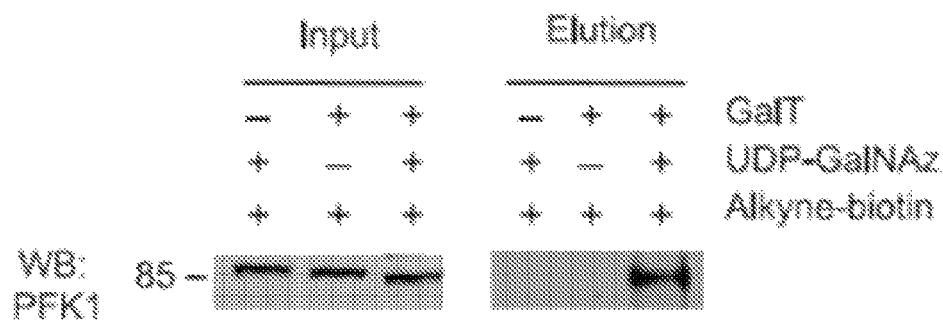
Figure 1:
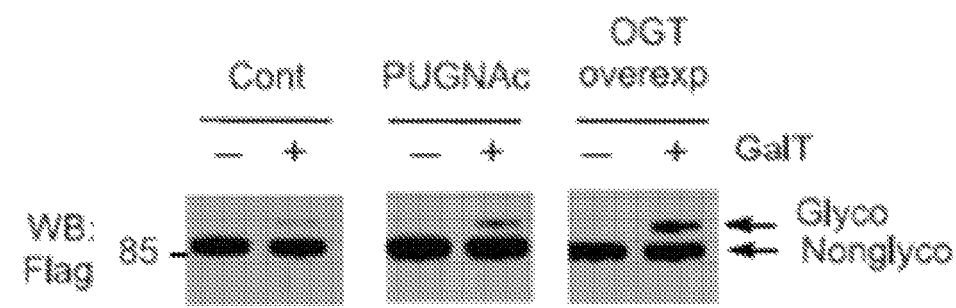
Figure 1:
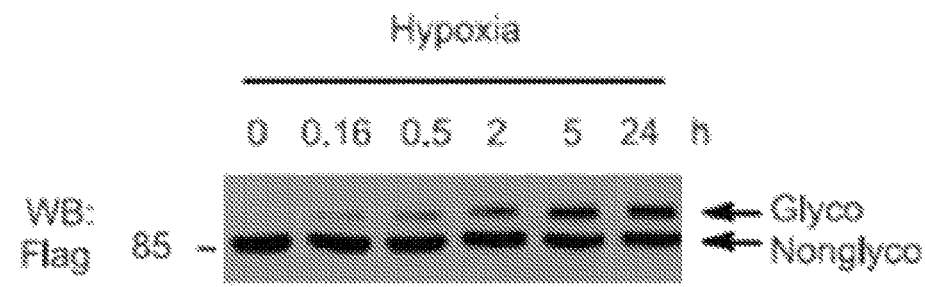
Figure 1:
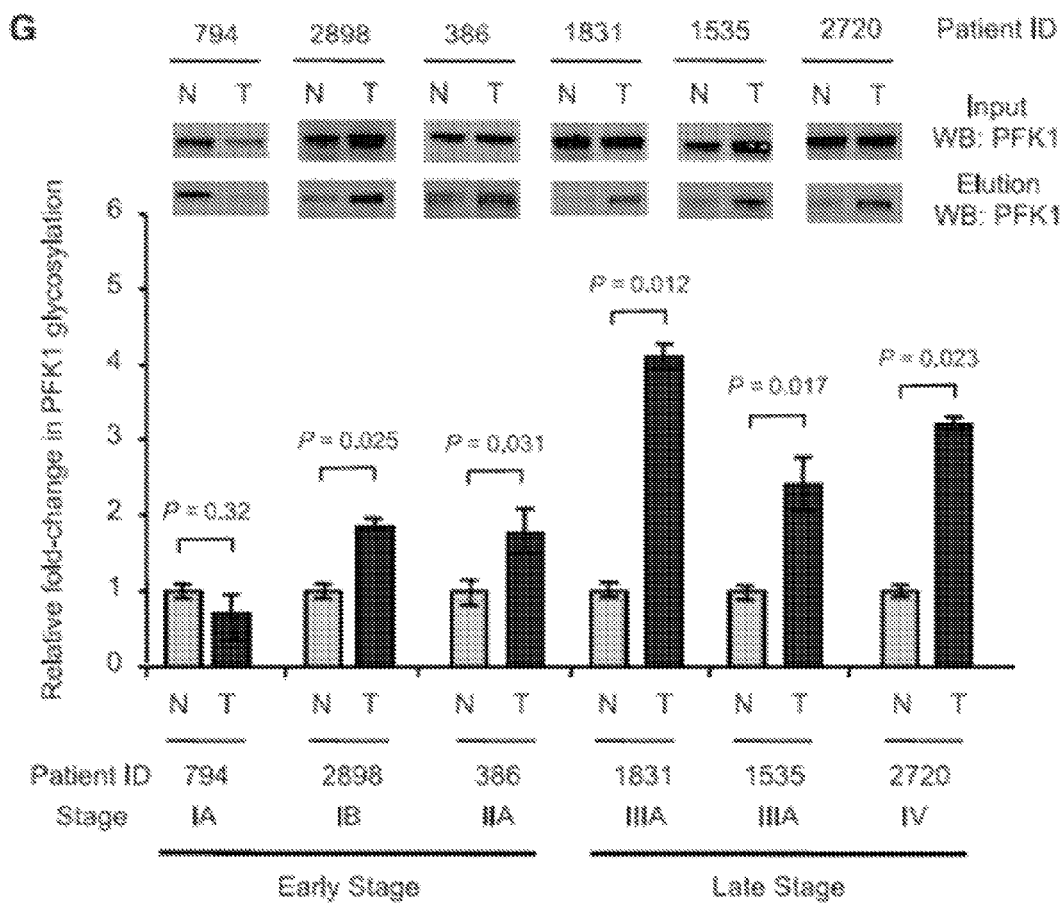

As used in the specification and claims, the singular form "a", "an" and "the" include plural references unless the context clearly dictates otherwise. For example, the term "a cell" includes a plurality of cells, including mixtures thereof.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "vector" as used herein, refers to a polynucleotide molecule, such as a DNA molecule. It can be derived, from a plasmid, bacteriophage, yeast or virus, into which a polynucleotide can be inserted or cloned. A vector can contain one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector can comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. A vector can be one which is operably functional in a bacterial cell, such as a cyanobacterial cell. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A "subject," "individual" or "patient" is used interchangeably herein, which refers to a vertebrate, preferably a mammal, more preferably a human. Mammals include, but are not limited to mice, rats, dogs, pigs, monkey (simians) humans, farm animals, sport animals, and pets. Tissues, cells and their progeny of a biological entity obtained in vivo or cultured in vitro are also encompassed.

The term "therapeutic agent" refers to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

The terms "treatment" or "treating" refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "antagonist" as used herein refers to a molecule having the ability to inhibit a biological function of a target polypeptide. Accordingly, the term "antagonist" is defined in the context of the biological role of the target polypeptide. While preferred antagonists herein specifically interact with (e.g. bind to) the target, molecules that inhibit a biological activity of the target polypeptide by interacting with other members of the signal transduction pathway of which the target polypeptide is a member are also specifically included within this definition. Antagonists, as defined herein, without limitation, include oligonucleotide decoys, apatmers, anti-chemokine antibodies and antibody variants, peptides, peptidomimetics, non-peptide small molecules, antisense molecules, and small organic molecules.

The term "agonist" as used herein refers to a molecule having the ability to initiate or enhance a biological function of a target polypeptide. Accordingly, the term "agonist" is defined in the context of the biological role of the target polypeptide. While preferred agonists herein specifically interact with (e.g. bind to) the target, molecules that inhibit a biological activity of the target polypeptide by interacting with other members of the signal transduction pathway of which the target polypeptide is a member are also specifically included within this definition. Agonists, as defined herein, without limitation, include oligonucleotide decoys, apatmers, anti-chemokine antibodies and antibody variants, peptides, peptidomimetics, non-peptide small molecules, antisense molecules, and small organic molecules.

The term "effective amount" or "therapeutically effective amount" refers to the amount of an agent that is sufficient to effect beneficial or desired results. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose will vary depending on the particular agent chosen, the dosing regimen to be followed, whether it is administered in combination with other compounds, timing of administration, the tissue to be imaged, and the physical delivery system in which it is carried.

In one embodiment, comparatively low doses of an entire, naked antibody or combination of entire, naked antibodies are used. In some embodiments, antibody fragments are utilized, thus less than the complete antibody. In other embodiments, conjugates of antibodies with drugs, toxins or therapeutic radioisotopes are useful. Bispecific antibody fusion proteins which bind to the chemokine antigens can be used according to the present invention, including hybrid antibodies which bind to more than one antigen. Therefore, antibody encompasses naked antibodies and conjugated antibodies and antibody fragments, which may be monospecific or multispecific.

As used herein, a "binding agent" refers to any molecule that is capable of specifically binding a target glycosylated PFK-1. Examples of binding agents include polypeptides, nucleic acids, small organic molecules, small inorganic molecules, ligands, aptamers, and antibodies. A binding agent includes an agent that distinguish glycosylated PFK-1 from non-glycosylated PFK-1 by exhibiting preferential binding to glycosylated PFK-1. Examples of binding agents include antibodies and aptamers.

The term "antibody" as used herein includes all forms of antibodies such as recombinant antibodies, humanized antibodies, chimeric antibodies, single chain antibodies, humanized antibodies, fusion proteins, monoclonal antibodies, etc.

Antibodies according to the present invention may be modified in a number of ways. The term "antibody" includes any antibody, antigen binding antibody fragments, derivatives, functional equivalents and homologues of antibodies, including synthetic molecules and molecules whose shape mimics that of an antibody enabling it to bind an antigen or epitope. Antibodies also include any protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. Antibody herein is meant to include full length antibodies and antibody fragments, and may refer to a natural antibody from any organism, an engineered antibody, or an antibody generated recombinantly for experimental, therapeutic, or other purposes. The term "antibody" includes antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. Particularly preferred are full length antibodies that comprise Fc variants. The term "antibody" also includes monoclonal and polyclonal antibodies. Antibodies can be antagonists, agonists, neutralizing, inhibitory, or stimulatory.

The antibodies of the present invention may be nonhuman, chimeric, humanized, or fully human. For a description of the concepts of chimeric and humanized antibodies see Clark et al., 2000 and references cited therein (Clark, 2000, Immunol Today 21:397-402). Chimeric antibodies comprise the variable region of a nonhuman antibody, for example VH and VL domains of mouse or rat origin, operably linked to the constant region of a human antibody (see for example U.S. Pat. No. 4,816,567). In a preferred embodiment, the antibodies of the present invention are humanized. By "humanized" antibody as used herein is meant an antibody comprising a human framework region (FR) and one or more complementarity determining regions (CDR's) from a non-human (such as mouse or rat) antibody. The non-human antibody providing the CDR's is called the "donor" and the human immunoglobulin providing the framework is called the "acceptor." Humanization relies principally on the grafting of donor CDRs onto acceptor (human) VL and VH frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (See e.g. U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). The humanized antibody optimally also will comprise at least a portion of an immunoglobulin constant region, typically that of a human immunoglobulin, and thus will typically comprise a human Fc region. Methods for humanizing non-human antibodies are well known in the art, and can be essentially performed following the method of Winter and co-workers (Jones et al., 1986, Nature 321:522-525; Riechmann et al., 1988, Nature 332:323-329; Verhoeyen et al., 1988, Science, 239:1534-1536). Additional examples of humanized murine monoclonal antibodies are also known in the art, for example antibodies binding human protein C (O'Connor et al., 1998, Protein Eng 11:321-8), interleukin 2 receptor (Queen et al., 1989, Proc Natl Acad Sci, USA 86:10029-33), and human epidermal growth factor receptor 2 (Carter et al., 1992, Proc Natl Acad Sci USA 89:4285-9). In some embodiments, the antibodies of the present invention may be fully human, that is the sequences of the antibodies are completely or substantially human. A number of methods are known in the art for generating fully human antibodies, including the use of transgenic mice (Bruggemann et al., 1997, Curr Opin Biotechnol 8:455-458) or human antibody libraries coupled with selection methods (Griffiths et al., 1998, Curr Opin Biotechnol 9:102-108).

Also included within the definition of "antibody" are aglycosylated antibodies. By "aglycosylated antibody" as used herein is meant an antibody that lacks carbohydrate attached at position 297 of the Fc region, wherein numbering is according to the EU system as in Kabat. The aglycosylated antibody may be a deglycosylated antibody, which is an antibody for which the Fc carbohydrate has been removed, for example chemically or enzymatically. Alternatively, the aglycosylated antibody may be a nonglycosylated or unglycosylated antibody, that is an antibody that was expressed without Fc carbohydrate, for example by mutation of one or more residues that encode the glycosylation pattern or by expression in an organism that does not attach carbohydrates to proteins, for example bacteria.

Also included within the definition of "antibody" are full-length antibodies that contain an Fc variant portion. By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, Cg1, Cg2, and Cg3. In some mammals, for example in camels and llamas, IgG antibodies may consist of only two heavy chains, each heavy chain comprising a variable domain attached to the Fc region. By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3.

In some embodiments, antibodies are immobilized on a substrate. Antibodies may be non-diffusibly bound to an insoluble support having isolated sample-receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes, and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. In some cases magnetic beads and the like are included.

In general, an antibody or other suitable binding partner is specific for a desired target antigen. In some embodiments, an antibody is specific to a particular glycosylated PFK-1 polypeptide (e.g. PFK-1 glycosylated at serine 529), and binds the particular glycosylated PFK-1 polypeptide with greater affinity than other PFK-1 polypeptides. Accordingly, in one aspect, the invention provides an isolated antibody or antigen-binding antibody fragment thereof, directed specifically to a human glycosylated PFK-1 polypeptide, or protein fragment thereof comprising glycosylated serine 529. In some embodiments, the affinity with which an antibody binds a particular glycosylated PFK-1 polypeptide (e.g. PFK-1 glycosylated at serine 529) is about or more than about 2, 3, 4, 5, 6, 7, 8, 9, 10, 15, 20, 25, 50, 75, 100, 150, 200, 300, 400, 500, 1000, $1\times10^4$, $1\times10^5$, $1\times10^6$, $1\times10^7$, $1\times10^8$, or more fold greater than the affinity with which the antibody binds other PFK-1 polypeptides.

The term "aptamer" as applied to bioactive agent includes DNA, RNA or peptides that are selected based on specific binding properties to a particular molecule. For example, an aptamer(s) can be selected for binding a particular gene or gene product, where selection is made by methods known in the art and familiar to one of skill in the art. Subsequently, said aptamer(s) can be administered to a subject to modulate or regulate an immune response. Some aptamers having affinity to a specific protein, DNA, amino acid and nucleotides have been described (e.g., K. Y. Wang, et al., *Biochemistry* 32:1899-1904 (1993); Pitney et al., U.S. Pat. No. 5,691,145; Gold, et al., *Ann. Rev. Biochem.* 64:763-797 (1995); Szostak et al., U.S. Pat. No. 5,631,146). High affinity and high specificity binding aptamers have been derived from combinatorial libraries (supra, Gold, et al.). Aptamers may have high affinities, with equilibrium dissociation constants ranging from micromolar to sub-nanomolar depending on the selection used. Aptamers may also exhibit high selectivity, for example, showing a thousand fold discrimination between 7-methylG and G (Haller and Sarnow, *Proc. Natl. Acad. Sci. USA* 94:8521-8526 (1997)) or between D and L-tryptophan (supra, Gold et al.).

The term "glycosylation" refers to covalent modifications of proteins with carbohydrates. Glycosylation can be achieved through N-glycosylation or O-glycosylation. O-linked protein glycosylation refers to glycosylation that involves the O-linkage of N-acetylglucosamine (GlcNAc) to serine or threonine residues in the protein backbone. The enzyme performing this protein modification is O-linked N-acetylglucosamine transferase (OGT).

DETAILED DESCRIPTION

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2$^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The present invention relates to phosphofructokinase 1 (PFK-1) and its involvement in cancer formation and/or progression. The present invention provides methods and compositions particularly useful for diagnosis, prognosis, and/or treatment of cancer associated with the glycosylation state of PFK-1.

Methods of the Present Invention

In one aspect, the invention provides a method of detecting a cancer tissue. In one embodiment, the method comprises (a) providing a sample of a subject; (b) detecting a level of glycosylated phosphofructokinase 1 (PFK-1) by performing a binding assay with a binding agent that specifically binds PFK-1, said assay yielding a detectable signal indicative of said level of glycosylated PFK-1; (c) designating the sample as cancerous if the detected level of glycosylated PFK-1 in the sample is at least 1.5 times a baseline level of glycosylated PFK-1 in a non-cancerous control sample; and (d) reporting the result of step (c) to a designated person or entity. In some embodiments, PFK-1 glycosylation comprises glycosylation at serine 529. In some embodiments, the binding assay comprises isolating glycosylated proteins from other proteins in the sample, and contacting the isolated proteins with the binding agent. In some embodiments, the binding assay comprises contacting protein derived from the sample with the binding agent, and the binding agent specifically binds a glycosylated form of PFK-1.

Samples utilized in the present method may be obtained by any suitable means, including but not limited to needle aspiration, fine needle aspiration, core needle biopsy, vacuum assisted biopsy, large core biopsy, incisional biopsy, excisional biopsy, punch biopsy, shave biopsy, skin biopsy, and venipuncture. The samples can be collected from a subject for analysis. In some embodiments, the samples comprise a blood sample, a plasma sample, a urine sample, a saliva sample, a nasal mucus sample, or a combination thereof. In some embodiments, the samples comprise tissue samples from any origin including but not limited to liver, lung, brain, kidney, bladder, heart, skin, ovary, testicle, tissue cultures or cells derived therefrom, and the progeny thereof. A sample may be analyzed directly for its contents, or may be processed to purify one or more of its contents for analysis. Methods of direct analysis of samples are known in the art and include, without limitation, mass spectrometry and histological staining procedures. In some embodiments, one or more components are isolated from the sample for the detection of PFK-1 glycosylation. In some embodiments, the isolated component of the sample comprises a protein (e.g. total protein, cytoplasmic protein, or membrane protein). Methods for the protein purification from a sample are known in the art.

Any cancer may be analyzed according to the methods of the invention. Many kinds of cancers are known in the art. Examples of types of cancers include, without limitation, cancers originating from epithelial cell tissue (carcinomas), blood cells (leukemias, lymphomas, myelomas), connective tissue (sarcomas), or glial or supportive cells (gliomas). In some embodiments, the target cancers are carcinomas and/or blood cell malignancies. In some embodiments, the target cancers are lung tumors, breast tumors, ovarian tumors, pancreatic tumors, glioblastoma tumors, and/or sarcomas. Cancers may comprise solid and/or non-solid tumors. Cancers may comprise primary and/or secondary tumors. Non-limiting examples of cancers that may be analyzed according to the methods of the invention include Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Müllerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, primary or secondary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Szary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, and Wilms' tumor. Other non-limiting examples of cancer types are described in U.S. Pat. No. 7,405,227, incorporated herein by reference in its entirety.

In some embodiments, a sample is assayed to designate a stage of cancer progression. As used herein, "cancer progression" refers to any measure of cancer growth, development, and/or maturation including metastasis. Cancer progression includes increase in cell number, cell size, tumor size, and number of tumors, as well as morphological and other cellular and molecular changes and other characteristics. As an example, one measure of cancer progression is the use of staging characteristics. As an additional example, one measure of cancer progression is the use of detecting expression, whether at the protein or mRNA level, of certain genes. In some embodiments, the stage of cancer progression is indicated by the detected level of glycosylated PFK-1 in the sample.

In some embodiments, a sample is designated cancerous if the detected level of glycosylated PFK-1 in the sample is at least 1.0 times, 1.5 times, 2.0 times, 2.5 times, 3.0 times, 5.0 times, 10.0 times, 20.0 times, 50.0 times, or more as compared to a baseline glycosylated PFK-1. In some embodiments, the sample is designated as early stage cancer if the detected level of glycosylated PFK-1 in the sample is between 1.5-3 times a baseline level of glycosylated PFK-1 in a non-cancerous control sample. In some embodiments, a sample is designated as early stage cancer if the detected level of glycosylated PFK-1 in the sample is between 1.5-1.8, 1.8-2.0, 2.0-2.2, 2.2-2.5, 2.5-2.7, or 2.7-3.0 times a baseline level of glycosylated PFK-1 in a non-cancerous control sample. In some embodiments, a sample is designated as early stage cancer if the detected level of glycosylated PFK-1 in the sample is 1.8 times a baseline level of glycosylated PFK-1 in a non-cancerous control sample.

In some embodiments, a sample is designated as late-stage cancer if the detected level of glycosylated PFK-1 in the sample is at least 2.5, 3.0, or 3.5 times a baseline level of glycosylated PFK-1 in a non-cancerous control sample. In some embodiments, a sample is designated as late-stage cancer if the detected level of glycosylated PFK-1 in the sample is between 2.5-2.7, 2.7-3.0, 3.0-3.2, 3.2-3.5, 3.5-3.7, 3.7-4.0, or more than 4.0, times a baseline level of glycosylated PFK-1 in a non-cancerous control sample. In some embodiments, a sample is designated as late-stage cancer if the detected level of glycosylated PFK-1 in the sample is at least 3.2 times a baseline level of glycosylated PFK-1 in a non-cancerous control sample.

Glycosylation level of PFK-1 can be determined by methods known in the art. For example, glycosylation of PFK-1 may be detected by a variety of assays (e.g., binding assays) discussed below. For example, one can compare the molecular weight. Molecular weight of a glycosylated PFK-1 is larger than that of predicted size calculated from the amino acid sequence of the polypeptide by addition of glycoside chain. Furthermore, when the molecular weight of glycosylated protein might be reduced by glycosidase treatment (e.g., O-GlcNAcase treatment), it was confirmed that the difference of the molecular weight is caused by addition of glycoside chain. Methods for estimating a molecular weight of a protein are well known (e.g., mass spectroscopy). For example, glycosylation level of PFK-1 in a cell may be estimated by separation of cell lysate. For example, SDS-polyacrylamide gel can be used for separating the polypeptide. The polypeptide separated in the gels is transferred to nitrocellulose membranes for immunoblotting analysis.

Exemplary binding Assays

Glycosylation level of PFK-1 can be determined using enzyme-based methods. For example, click chemistry, utilizing specific enzymes, may be used to label and isolate glycosylated proteins. In particular, a protein that is O-β-GlcNAcylated or that carries with a terminal GlcNAc (either purified or in a protein mixture) can be incubated with GALT (β-1,4-galactosyltransferase), which specifically adds an azidogalactose to GlcNAc. The modified O-GlcNAc is then allowed to react with a fluorescent alkyne, the sample is resolved on SDS-PAGE, and the modified protein is visualized by UV, using a gel imager (T. H. Steinberg, Methods in Enzymology, vol. 463, no. C, pp. 541-563, 2009). O-GlcNAcylated peptides can be labeled and further analyzed by mass spectrometry.

In some embodiments, PFK-1 glycosylation in a sample is identified by first isolating glycosylated proteins from other proteins in the sample, following by contacting the isolated proteins with a binding agent that specifically binds PFK-1.

For example, glycosylated PFK-1 can be detected using reagents that selectively bind glycoside chain with high affinity. Such reagents are known in the art or can be determined by screening assays known in the art. For example, lectins are well known as glycoside chain specific probe. Lectin reagent conjugated with detectable label such as alkaline-phosphatase is also commercially available.

In some embodiments, PFK-1 glycosylation in a sample is identified by contacting protein derived from the sample with a binding agent that specifically binds glycosylated PFK-1, such that detection of the binding between the glycosylated PFK-1 and the binding agent indicates the presence of PFK-1 glycosylation.

In some embodiments, glycosylated PFK-1 can be detected using reagents that selectively recognize glycosylated level of the polypeptide. For example, the glycosylation level of PFK-1 can be detected by immunological method. Any immunological techniques using an antibody recognizing glycosylated polypeptide can be used for the detection. For example, an antibody against glycosylated polypeptide is commercial available (CTD 110.1 or RL2). ELISA or immunoblotting with antibodies recognizing glycosylated polypeptide can be used for the present invention.

In some embodiments, antibodies, or fragments or equivalents thereof, are used in the detection of PFK-1 glycosylation, or in the treatment of a subjection having a cancer comprising a glycosylated PFK-1. Antibody-based detection methods are known in the art, and include without limitation, ELISA, immunohistochemistry, agglutination, Western blotting, and others. An antibody against glycosylated polypeptide is commercial available (CTD 110.1).

Methods of producing antibodies are known in the art. Preferred antibodies are isolated, in the sense of being purified to reduce the presence of contaminants such as antibodies able to bind other polypeptides and/or other serum components. Monoclonal antibodies are preferred for some purposes, though polyclonal antibodies are within the scope of the present invention.

Antibodies may be obtained using techniques which are standard in the art. Methods of producing antibodies include immunizing a mammal (e.g. mouse, rat, rabbit) with a polypeptide comprising the target antigen. Antibodies may be obtained from immunized animals using any of a variety of techniques known in the art, and screened, preferably using binding of antibody to antigen of interest. For instance, Western blotting techniques or immunoprecipitation may be used (Armitage et al, Nature, 357:80-82, 1992).

As an alternative or supplement to immunizing a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

In some embodiments, the antibody for detection of PFK-1 glycosylation is a purified antibody, or antigen-binding antibody fragment thereof, directed specifically to glycosylated PFK-1. The antibody can be a monoclonal antibody, a humanized antibody, or a human antibody. In some embodiments, the antibody is an antibody that binds an epitope comprising glycosylated serine 529 of PFK-1. In some embodiments, the antibody comprises a detectable label.

Detection of PFK-1 glycosylation may be accomplished by utilizing a variety of labels known in the art. In some embodiments, the detection of PFK-1 glycosylation is done using a label. The term "label" is used to refer to a molecule that can be directly (i.e., a primary label) or indirectly (i.e., a secondary label) detected; for example a label can be visualized and/or measured or otherwise identified so that its presence or absence can be known. A compound can be directly or indirectly conjugated to a label which provides a detectable signal, e.g. radioisotopes, fluorescent moieties, enzymes, antibodies, particles such as magnetic particles, chemiluminescent moieties, or specific binding molecules, etc. Specific binding molecules include pairs, such as biotin and streptavidin, digoxin and antidigoxin etc. Preferred labels include, but are not limited to, optical fluorescent and chromogenic dyes including labels, label enzymes, and radioisotopes.

In some embodiments, radiolabeled donor for glycosylation may be used for detecting the addition of glycoside chain to PFK-1. Transfer of the radiolabel to PFK-1 can be detected, for example, by SDS-PAGE electrophoresis and fluorography. Alternatively, following the glycosylation reaction, PFK-1 can be separated from the glycosyl donor by filtration, and the amount of radiolabel retained on the filter quantitated by scintillation counting. Other suitable labels (e.g., fluorescent labels) that can be attached to glycosyl donor, such as chromogenic and fluorescent labels, and methods of detecting transfer of these labels to the substrate, are known in the art.

In some embodiments, detection of PFK-1 glycosylation through the use of a binding partner such as an antibody may be accomplished by any of a variety of methods known in the art. In some embodiments, the binding partner comprises a label.

Non-limiting exemplary labels include isotopic labels, which may be radioactive or heavy isotopes; magnetic, electrical, and thermal labels; colored, optical labels including luminescent, phosphorous and fluorescent dyes or moieties; and binding partners. Labels can also include enzymes (horseradish peroxidase, etc.) and magnetic particles. In some embodiments, the label is PEG mass tag (as detailed in the examples).

In some embodiments, the detection label is a primary label. A primary label is one that can be directly detected, such as a fluorophore. Preferred labels include optical labels such as fluorescent dyes or moieties. Fluorophores include "small molecule" fluors, and proteinaceous fluors (e.g. green fluorescent proteins and all variants thereof).

The term "fluorescent label" encompasses any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAE-DANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference.

Suitable fluorescent labels also include, but are not limited to, green fluorescent protein (GFP; Chalfie, et al., Science 263(5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12):5408-5417 (1993)), β-galactosidase (Nolan, et al., Proc Natl Acad Sci USA 85(8):2603-2607 (April 1988)) and Renilla WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558). All of the above-cited references are expressly incorporated herein by reference.

Illustrative examples of useful labels include, but are not limited to: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). In some embodiments, the label is a DNA-binding dye. Non-limiting examples of DNA-binding dyes suitable for this application include SYBR green, SYBR blue, DAPI, propidium iodine, Hoechst stain, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like. Further non-limiting examples of suitable labels include EvaGreen® (Biotium, Hayward, Calif.), SYBR® Green I, PicoGreen™, LC Green™, SYBR GreenER®, PO-PRO®.-1, BO-PRO®.-1, SYTO® 9, SYTO®™43, SYTO®. 44, SYTO®. 45, SYTOX® Blue, POPO™.-1, POPO™.-3, BOBO™.-1, BOBO™-3, LO-PRO™-1, JO-PRO™-1, YO-PRO®-1, TO-PRO®-1, SYTO® 9, SYTO®11, SYTO®13, SYTO®15, SYTO®16, SYTO®20, SYTO®23, TOTO™3, YOYO®-3 (Molecular Probes, Inc., Eugene, Oreg.), GelStar® (Cambrex Bio Science Rockland Inc., Rockland, Me.), Ethidium Bromide, thiazole orange (Aldrich Chemical Co., Milwaukee, Wis.), BEBO, BETO, BOXTO (TATAA Biocenter AB., Goteborg, Sweden). Additional examples of labels are described in US20110136201, incorporated herein by reference. Tandem conjugate protocols for Cy5PE, Cy5.5PE, Cy7PE, Cy5.5APC, Cy7APC are known in the art. Quantitation of fluorescent probe conjugation may be assessed to determine degree of labeling and protocols including dye spectral properties are also well known in the art.

In some embodiments, a secondary detectable label is used. A secondary label is one that is indirectly detected; for example, a secondary label can bind or react with a primary label for detection, or can act on an additional product to generate a primary label (e.g. enzymes), etc. Secondary labels include, but are not limited to, one of a binding partner pair; chemically modifiable moieties; nuclease inhibitors; and enzymes such as horseradish peroxidase, alkaline phosphatases, luciferases.

In some embodiments, the secondary label is a one of a pair of binding partners. For example, the label may be a hapten or antigen, which will bind its binding partner. For example, suitable binding partner pairs include, but are not limited to: antigens (such as proteins (including peptides) and small molecules) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Preferred binding partner pairs include, but are not limited to, biotin (or imino-biotin) and streptavidin, digoxigenin and antibodies, and Prolinx™ reagents.

In some embodiments, the binding partner pair comprises an antigen and an antibody that will specifically bind to the antigen. The binding should be sufficient to remain bound under the conditions of the assay, including wash steps to remove non-specific binding. In some embodiments, the dissociation constants of the pair will be less than about $10^{-4}$ to $10^{-9}$ $M^{-1}$, with less than about $10^{-5}$ to $10^{-9}$ $M^{-1}$ being preferred and less than about $10^{-7}$ to $10^{-9}$ $M^{-1}$ being particularly preferred.

Other possible labels include macromolecular colloidal particles or particulate material such as latex beads that are colored, magnetic or paramagnetic, and biologically or chemically active agents that can directly or indirectly cause detectable signals to be visually observed, electronically detected or otherwise recorded. Other methods may also be used to detect interaction between the protein and the antibody, including physical methods such as surface plasmon resonance, agglutination, light scattering or other means.

Reporting Results

In some embodiments, a method of the invention comprises reporting results of an assay. Reporting may be by any manner of communication known in the art. Communication may local to where the results were generated, or may be communicated to another location, such as by wired or wireless communication. Non-limiting examples of wireless communication include bluetooth, RTM technology, or wireless internet connection. Various communication methods can be utilized, such as a dial-up wired connection with a modem, a direct link such as a T1, ISDN, or cable line. In some embodiments, a wireless connection is established using exemplary wireless networks such as cellular, satellite, or pager networks, or a local data transport system such as Ethernet or token ring over a local area network. In some embodiments, the information is encrypted before it is transmitted over a wireless network. In some embodiments, the communication assembly may contain a wireless infrared communication component for sending and receiving information. In some embodiments, results are reported to a particular person or entity. Non-limiting examples of persons or entities to whom results may be reported include a patient, medical personnel, clinicians, laboratory personnel, insurance company personnel, or others in the health care industry.

In some embodiments, results are communicated to an external device. In some embodiments the external device can be a computer system, server, PDA, cell phone, or other electronic device capable of storing information or processing information. In some embodiments the external device includes one or more computer systems, servers, or other electronic devices capable of storing information or processing information. In some embodiments an external device may include a database of patient information, for example but not limited to, medical records or patient history, clinical trial records, or preclinical trial records. A server can include a database and system processes. A database can reside within the server, or it can reside on another server system that is accessible to the server. As the information in a database may contain sensitive information, a security system can be implemented that prevents unauthorized users from gaining access to the database.

Screening Assays

Accordingly, in one embodiment, the present invention provides method of developing an anti-cancer agent that reduces phosphofructokinase 1 (PFK-1) glycosylation. The method comprises (a) contacting a cancer cell that expresses PFK-1 with a candidate agent; (b) detecting a reduction in PFK-1 glycosylation in the cell relative to a control cell; and (c) selecting the agent as a candidate that specifically reduces PFK-1 glycosylation if the level of PFK-1 glycosylation is reduced relative to the control cell.

The cancer cell can be any cancer cell. For example, the cancer cell can be a lung cancer cell, an osteosarcoma cell, a breast cancer cell, a colon cancer cell, a gastric cancer cell, a pancreatic cancer cell, a prostate cancer cell or a melanoma cell. In some embodiments, the cancer cell is a lung cancer cell.

The candidate agent can be a peptide, antibody, aptamer, siRNA, miRNA, EGS, antisense molecule, peptidomimetic, or small molecule. For example, the candidate agent can be an antisense oligonucleotide, peptide, an antibody, a liposome, a small interfering RNA, small organic compound and an inorganic compound. In some embodiments, the agent binds to serine 529 of PFK-1 and blocks glycosylation. In some embodiments, the agent binds to a site adjacent to serine 529 of PFK-1 thereby reducing glycosylation at serine 529. In some embodiments, the agent reduces activity or expression of O-GlcNAc transferase (OGT). In some embodiments, the agent enhances activity or expression of O-GlcNAcase (OGA).

The detecting step can be accomplished by any method known in the art. For example, the detecting step can involve an affinity-based assay. Exemplary affinity-based assays include an immunoassay or an enzyme-based assay.

The reduction of PFK-1 glycosylation can be characterized by any method known in the art. For example, the reduction of PFK-1 glycosylation can be characterized by an increased glycolytic rate in the cell, by an increased lactate production in the cell, by a decreased pentose phosphate pathway (PPP) activity or a decreased pentose phosphate pathway (PPP) flux, by a decreased NADPH level or GSH level, or by promotion of PFK-1 association into tetramers and higher oligomers.

Compositions of the Present Invention

The present invention provides an agent that reduces phosphofructokinase 1 (PFK-1) glycosylation. The agents effective for reducing PFK-1 glycosylation can be a peptide, an antibody, an aptamer, a siRNA, a miRNA, an EGS, an antisense molecule, a peptidomimetic, or a small molecule. For example, the agent can be a molecule (e.g., an antibody) that directly binds to serine 529 of PFK-1 and blocks glycosylation, or a molecule (e.g., an antibody) that binds to a site adjacent to serine 529 of PFK-1 thereby reduces glycosylation at serine 529. The agent can also be a molecule effective in modulating the expression or activity level of other genes or proteins associated with PFK-1 glycosylation. In some embodiments, the agent is a molecule that specifically increases PFK-1 expression or activity to counteract the effects of PFK-1 glycosylation. In some embodiments, the agent is a molecule that activates the glycosylated form of PFK-1 to counteract the effects of glycosylation without decreasing the level of PFK-1 glycosylation.

For example, the agent can be a molecule that reduces activity or expression of O-GlcNAc transferase (OGT), or a molecule that increases activity or expression of O-GlcNAcase (OGA). Examples of an agent that reduces activity or expression of OGT (i.e., an OGT antagonist) include, but are not limited to, an OGT antagonistic antibody, an OGT antagonistic aptamer, siRNA against OGT, miRNA against OGT, EGS against OGT, antisense molecule against OGT, and small molecules. Examples of an agent that increases activity or expression of OGA (i.e., an OGA agonist) include an OGA agonistic antibody, an OGA agonistic aptamer, an OGA polypeptide, an OGA peptide or peptidomimetic, a nucleic acid encoding OGA, and small molecules.

In some embodiments, an antibody or antigen-binding antibody fragment thereof is used to reduce PFK-1 glycosylation. Examples of such antibody agents include an antibody or antigen-binding antibody fragment thereof that directly binds to serine 529 of PFK-1 and blocks glycosylation, or an antibody or antigen-binding antibody fragment thereof that binds to a site adjacent to serine 529 of PFK-1 thereby reduces glycosylation at serine 529, or an antibody targeting one or more genes implicated in PFK-1 glycosylation (e.g., an OGT antagonistic antibody or an OGA agonistic antibody).

Producing antibodies specific for polypeptides encoded by any of the preceding genes, or specific to any epitopes thereof, is known to one of skill in the art, such as disclosed in U.S. Pat. Nos. 6,491,916; 6,982,321; 5,585,097; 5,846,534; 6,966,424 and U.S. Patent Application Publication Nos. 2005/0054832; 2004/0006216; 2003/0108548, 2006/002921 and 2004/0166099, each of which is incorporated herein by reference. For example, monoclonal antibodies can be obtained by injecting mice with a composition comprising the antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen that was injected, culturing the clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan et al., (eds.), *CURRENT PROTOCOLS IN IMMUNOLOGY*, pages 2.7.1 to 2.7.12 and pages 2.9.1 to 2.9.3 (John Wiley & Sons, Inc. 1991). Also, see Baines et al., *"Purification of Immunoglobulin G (IgG),"* in *METHODS IN MOLECULAR BIOLOGY, VOL.* 10, pages 79 to 104 (The Humana Press, Inc. 1992).

Suitable amounts of well-characterized antigen for production of antibodies can be obtained using standard techniques. As an example, an antigen can be immunoprecipitated from cells using the deposited antibodies described by Tedder et al., U.S. Pat. No. 5,484,892. Alternatively, such antigens can be obtained from transfected cultured cells that overproduce the antigen of interest. Expression vectors that comprise DNA molecules encoding each of these proteins can be constructed using published nucleotide sequences. See, for example, Wilson et al., *J. Exp. Med.* 173:137-146 (1991); Wilson et al., *J. Immunol.* 150:5013-5024 (1993). As an illustration, DNA molecules encoding CD3 can be obtained by synthesizing DNA molecules using mutually priming long oligonucleotides. See, for example, Ausubel et al., (eds.), *CURRENT PROTOCOLS IN MOLECULAR BIOLOGY*, pages 8.2.8 to 8.2.13 (1990). Also, see Wosnick et al., *Gene* 60:115-127 (1987); and Ausubel et al. (eds.), *SHORT PROTOCOLS IN MOLECULAR BIOLOGY*, 3rd Edition, pages 8-8 to 8-9 (John Wiley & Sons, Inc. 1995).

Established techniques using the polymerase chain reaction provide the ability to synthesize genes as large as 1.8 kilobases in length. (Adang et al., *Plant Molec. Biol.* 21: 1131-1145 (1993); Bambot et al., *PCR Methods and Applications* 2:266-271 (1993); Dillon et al., *"Use of the Polymerase Chain Reaction for the Rapid Construction of Synthetic Genes,"* in *METHODS IN MOLECULAR BIOLOGY*, Vol. 15: *PCR PROTOCOLS: CURRENT METHODS AND APPLICATIONS*, White (ed.), pages 263 268, (Humana Press, Inc. 1993)). In a variation, monoclonal antibody can be obtained by fusing myeloma cells with spleen cells from mice immunized with a murine pre-B cell line stably transfected with cDNA which encodes the antigen of interest. See Tedder et al., U.S. Pat. No. 5,484,892.

In other embodiments, an external guide sequence (EGS) is used to target a gene (e.g., OGT) (see for example, U.S. Pat. Nos. 5,728,521, 6,057,153). In one aspect, the agent of the present invention may utilize RNA interference (RNAi) as a mechanism to reduce OGT expression and/or activity. For example, RNAi may be used to target OGT expression and/or activity, thereby reducing PFK-1 glycosylation. RNAi is a process of sequence-specific, post-transcriptional gene silencing initiated by double stranded RNA (dsRNA) or siRNA. RNAi is seen in a number of organisms such as *Drosophila*, nematodes, fungi and plants, and is believed to be involved in anti-viral defense, modulation of transposon activity, and regulation of gene expression. During RNAi, dsRNA or siRNA induces degradation of target mRNA with consequent sequence-specific inhibition of gene expression. In some embodiments, miRNA is used to target OGT.

A small interfering RNA (siRNA) is a RNA duplex of nucleotides that is targeted to a gene interest. A RNA duplex refers to the structure formed by the complementary pairing between two regions of a RNA molecule. siRNA is targeted to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' and/or 5' overhang portions. In some embodiments, the overhang is a 3' and/or a 5' overhang 0, 1, 2, 3, 4 or 5 nucleotides in length. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

The agents can be expressed in cells or tissues so that such agents are expressed to impart their desired function such as reduction of PFK-1 glycosylation. Typically, gene expression is placed under the control of certain regulatory elements including constitutive or inducible promoters, cell type specific expression regulatory elements, and enhancers. Such a gene is said to be operably linked to the regulatory elements. For example, constitutive, inducible or cell/tissue specific promoters can be incorporated into an expression vector to regulate expression of a gene that is expressed in a host cell. Therefore, depending on the promoter elements utilized, an agent can be expressed as desired so as to reduce PFK-1 glycosylation.

Expression of the agents that reduce PFK-1 glycosylation can be temporally regulated by utilizing various expression systems. In some embodiments, a gene encoding a polypeptide agent can be operably linked to a controllable promoter element, such as a tet-responsive promoter. For example, where and when desired an inducible agent (e.g., tetracycline or analog thereof) can be administered to cells or a subject to induce expression of the polypeptide agent in a cell/tissue specific manner (e.g., mere tetracycline is delivered in a localized/limited manner). Such a system can provide tight control of gene expression in eukaryotic cells, by including the "off-switch" systems, in which the presence of tetracycline inhibits expression, or the "reversible" Tet system, in which a mutant of the *E. coli* TetR is used, such that the presence of tetracycline induces expression. These systems are disclosed, e.g., in Gossen and Bujard (*Proc. Natl. Acad. Sci. U.S.A.* (1992) 89:5547) and in U.S. Pat. Nos. 5,464,758; 5,650,298; and 5,589,362 by Bujard et al.

Additional examples of inducible promoters include MMTV, heat shock 70 promoter, GAL1-GAL10 promoter, metallothien inducible promoters (e.g., copper inducible ACE1; other metal ions), hormone response elements (e.g., glucocorticoid, estrogen, progestrogen), phorbol esters (TRE elements), calcium ionophore responsive element, or uncoupling protein 3, α human folate receptor, whey acidic protein, prostate specific promoter, as well as those disclosed in U.S. Pat. No. 6,313,373; see also, online at <biobase/de/pages/products/transpor.html> (providing a database with over 15,000 different promoter sequences classified by genes/activity); and Chen et al. *Nuc. Acids. Res.* 2006, 34: Database issue, D104-107.

Yet other inducible promoters include the growth hormone promoter; promoters which would be inducible by the helper virus such as adenovirus early gene promoter inducible by adenovirus E1A protein, or the adenovirus major late promoter; herpesvirus promoter inducible by herpesvirus proteins such as VP16 or 1CP4; promoters inducible by a vaccinia or pox virus RNA polymerases; or bacteriophage promoters, such as T7, T3 and SP6, which are inducible by T7, T3, or SP6 RNA polymerase, respectively.

In other embodiments, constitutive promoters may be desirable. For example, there are many constitutive promoters suitable for use in the present invention, including the adenovirus major later promoter, the cytomegalovirus immediate early promoter, the β actin promoter, or the β globin promoter. Many others are known in the art and may be used in the present invention. In yet further embodiments, a regulatory sequence can be altered or modified to enhance expression (i.e., increase promoter strength). For example, intronic sequences comprising enhancer function can be utilized to increase promoter function.

Furthermore, expression of the polypeptide agent may be desired in a particular subcellular location. When desired, the nucleic acid sequence encoding the polypeptide agent can be operably linked to the corresponding subcellular localization sequence by recombinant DNA techniques widely practiced in the art. Exemplary subcellular localization sequences include, but are not limited to, (a) a signal sequence that directs secretion of the gene product outside of the cell; (b) a membrane anchorage domain that allows attachment of the protein to the plasma membrane or other membraneous compartment of the cell; (c) a nuclear localization sequence that mediates the translocation of the encoded protein to the nucleus; (d) an endoplasmic reticulum retention sequence (e.g. KDEL sequence (SEQ ID NO: 4)) that confines the encoded protein primarily to the ER; (e) proteins can be designed to be farnesylated so as to associate the protein with cell membranes; or (f) any other sequences that play a role in differential subcellular distribution of a encoded protein product.

The agents of the present invention may also be in the form of a vector, such as a vector comprising a nucleic acid sequence encoding a polypeptide (e.g., an OGA polypeptide). Vectors utilized in in vivo or in vitro methods can include derivatives of SV-40, adenovirus, retrovirus-derived DNA sequences and shuttle vectors derived from combinations of functional mammalian vectors and functional plasmids and phage DNA. Eukaryotic expression vectors are well known, e.g. such as those described by Southern and Berg, *J. Mol. Appl. Genet.* 1:327-341 (1982); Subramini et al., *Mol. Cell. Biol.* 1:854-864 (1981), Kaufinann and Sharp, I 159:601-621 (1982); Scahill et al., *Proc. Natl. Acad. Sci. USA* 80:4654-4659 (1983) and Urlaub and Chasin, *Proc. Natl. Acad. Sci. USA* 77:4216-4220 (1980), which are hereby incorporated by reference. The vector used in the methods of the present invention may be a viral vector, preferably a retroviral vector. Replication deficient adenoviruses are preferred. For example, a "single gene vector" in which the structural genes of a retrovirus are replaced by a single gene of interest, under the control of the viral regulatory sequences contained in the long terminal repeat, may be used, e.g. Moloney murine leukemia virus (MoMuIV), the Harvey murine sarcoma virus (HaMuSV), murine mammary tumor virus (MuMTV) and the murine myeloproliferative sarcoma virus (MuMPSV), and avian retroviruses such as reticuloendotheliosis virus (Rev) and Rous Sarcoma Virus (RSV), as described by Eglitis and Andersen, *BioTechniques* 6(7):608-614 (1988), which is hereby incorporated by reference. Expression constructs may be viral or nonviral vectors. Viral vectors that are considered part of the invention include, but are not limited to, adenovirus, adeno-associated virus, herpesvirus, retrovirus (including lentiviruses), polyoma virus, or vaccinia virus.

Recombinant retroviral vectors into which multiple genes may be introduced may also be used according to the methods of the present invention. Vectors with internal promoters containing a cDNA under the regulation of an independent promoter, e.g. SAX vector derived from N2 vector with a selectable marker ($noe^R$) into which the cDNA for human adenosine deaminase (hADA) has been inserted with its own regulatory sequences, the early promoter from SV40 virus (SV40), may be designed and used in accordance with the methods of the present invention by methods known in the art.

Specific initiation signals can also be required for efficient translation of the nucleic sequences encoding the agents. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, may be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See e.g., Bittner et al., *Methods in Enzymol.* 153:516-544 (1987)).

In some embodiments, the agent is an inhibitor that downregulates OGT output, such as an inhibitor of OGT or inhibitor of another component of the OGT pathway. Examples of OGT inhibitors include, without limitation, the small molecule antagonists described in Gross et al., *J Am Chem Soc* 130:440-441, 2008 (e.g.,), the small molecule antagonists described in Gross et al., *J Am Chem Soc* 130:440-441, 2008 (e.g.,)

and the OGT inhibitors described in US2008/0182805 and US2012/0108605.

The present invention also provides a modified PFK-1 polypeptide comprising a mutation at serine 529 which is resistant to glycosylation. Typically, the modified PFK-1 polypeptides exhibit at least some PFK-1 activity. In some embodiments, the modified PFK-1 polypeptides have decreased PFK-1 activity relative to a wild-type PFK-1 polypeptide. In some embodiments, the mutant PFK-1 polypeptides have increased PFK-1 activity relative to a wild-type PFK-1 polypeptide. In some embodiments, the modified PFK-1 polypeptides have equivalent PFK-1 activity relative to a wild-type PFK-1 polypeptide. The modified PFK-1 polypeptides can be recombinant proteins or purified from a host cell. Typically, the modified PFK-1 polypeptide is resistant to glycosylation and has an increased PFK-1 activity relative to a wild-type PFK-1 polypeptide.

Provided herein is an isolated or synthetic modified PFK-1 polypeptide or a variant thereof having increased PFK-1 activity comprising a modification at an amino acid position corresponding to amino acid position 529 of the amino acid sequence set forth in SEQ ID NO: 1, wherein the modification confers resistance of the modified PFK-1 polypeptide or variant to glycosylation.

In some embodiments, the modification comprises a substitution or a deletion of the amino acid at amino acid position 529 compared to a wild type PFK-1 polypeptide set forth in SEQ ID NO: 1. In some embodiments, the modification comprises substitution of the amino acid at position 529 compared to a wild type PFK-1 polypeptide set forth in SEQ ID NO: 1. In some embodiments, the modification is a substitution of serine to an amino acid selected from among leucine, isoleucine, valine, alanine, glycine, methionine, cysteine, phenylalanine, tryptophan, lysine, arginine, histidine, proline, tyrosine, asparagine, glutamine, aspartic acid and glutamic acid at amino acid position 529 of the PFK-1 polypeptide. In some embodiments, the modification is a substitution of serine to an amino acid selected from among alanine or glycine at amino acid position 529 of the PFK-1 polypeptide. In some embodiments, the modification is a substitution of serine to alanine at amino acid position 529 of the PFK-1 polypeptide. In some embodiments, the modification comprises a deletion of amino acid position 529 of the wild-type PFK-1 polypeptide set forth in SEQ ID NO: 1. In some embodiments, the modified PFK-1 polypeptide comprises the sequence of amino acids set forth in SEQ ID NO: 2.

In some embodiments, the modified PFK-1 polypeptide comprises a substitution of the amino acid at position 529 compared to a wild type PFK-1 polypeptide set forth in SEQ ID NO: 1 and one or more additional amino acid substitutions. In some embodiments, the modified PFK-1 polypeptide comprises the sequence of amino acids set forth in SEQ ID NO: 1 or a variant that has at least about 60%, 70%, 75%, 80%, 85%, 90%, 95%, 96%, 97%, 98%, 99% or more sequence identity with the polypeptide having the sequence set forth in SEQ ID NO: 1, wherein the amino acid at position 529 is not serine or threonine. In some embodiments the modified PFK-1 polypeptide comprises a polypeptide having an alanine at the position corresponding to amino acid position 529 and having 65%, 70%, 75%, 80%, 85%, 90%, 95%, 96%, 97%, 98%, or 99% amino acid sequence identity to the polypeptide having the sequence set forth in SEQ ID NO: 2.

In some embodiments, the modified PFK-1 polypeptide comprises a modification at amino acid position 529 and a modification at one or more additional amino acid positions. In some embodiments, the modified PFK-1 polypeptide comprises a modification at amino acid position 529 and a modification at 1, 2, 3, 4, 5, 6, 7, 8, 9, 10, 11, 12, 13, 14, 15, 16, 17, 18, 19, 20 or more amino acid positions. In some embodiments, the modified PFK-1 polypeptide comprises a modification at position 529 and a modification at one additional amino acid position. In some embodiments, the modified PFK-1 polypeptide comprises an alanine at amino acid position 529 and a modification at 1, 2, 3, 4, 5, 6, 7, 8, 9, 10, 11, 12, 13, 14, 15, 16, 17, 18, 19, 20 or more additional amino acid positions.

Provided herein are nucleic acids encoding modified PFK-1 polypeptides. Methods for deducing nucleic acids that encode particular polypeptides are known in the art and involve standard molecular biology techniques. Exemplary nucleic acids encoding modified PFK-1 polypeptides provided herein are provided. It is understood that due to the degeneracy of the genetic code multiple variants nucleic acids exist that encode the same polypeptide. Nucleic acids that encode the modified PFK-1 polypeptides provided herein encompass such variants.

In some embodiments, the nucleic acid encoding a modified PFK-1 polypeptide provided herein is a DNA or an RNA molecule. In some embodiments, the nucleic acid encoding a modified PFK-1 polypeptide comprises a modification where the encoded polypeptide comprises a substitution of the amino acid serine at the position corresponding to amino acid position 529 of the wild-type PFK-1 polypeptide set forth in SEQ ID NO: 1. In some embodiments, the nucleic acid comprises a variant of the nucleic acid sequence set forth in SEQ ID NO: 3, wherein the nucleic acid codon encoding amino acid at position 529 is modified to encode an amino acid other than serine or theorine. In some embodiments, the nucleic acid comprises a variant of the nucleic acid sequence set forth in SEQ ID NO: 3, wherein the nucleic acid has at least about 60%, 70%, 75%, 80%, 85%, 90%, 95%, 96%, 97%, 98%, 99% or more sequence identity with the nucleic acid having the sequence set forth in SEQ ID NO: 3, wherein the nucleic acid codon encoding amino acid at position 529 does not encode serine or theorine.

In some embodiments, the nucleic acid provided herein encoding a modified PFK-1 polypeptide is an isolated or synthetic nucleic acid. In some embodiments, the nucleic acid provided herein encoding a modified PFK-1 polypeptide is a DNA molecule. In some embodiments, the nucleic acid provided herein encoding a modified PFK-1 polypeptide is a cDNA molecule. In some embodiments, the nucleic acid provided herein encoding a modified PFK-1 polypeptide is an RNA molecule. In some embodiments, the nucleic acid provided herein encoding a modified PFK-1 polypeptide is an inhibitory RNA molecule (i.e. RNAi). In some embodiments, the nucleic acid provided herein is a nucleic acid molecule that is complementary, or binds to, a nucleic acid encoding a modified PFK-1 polypeptide.

In some embodiments, the nucleic acid provided herein is a vector that comprises a nucleic acid molecule encoding a modified PFK-1 polypeptide provided herein. In some embodiments, the nucleic acid provided herein is a vector that comprises nucleic acid encoding a modified PFK-1 polypeptide provided herein is an expression vector. In some embodiments, the nucleic acid encoding a modified PFK-1 polypeptide provided herein is operably linked to a promoter. In some embodiments, the promoter is a constitutive or an inducible promoter. In some embodiments, provided herein is a host cell, comprising the vector or nucleic acid molecule encoding a modified PFK-1 polypeptide provided herein. In some embodiments, the cell is a prokaryotic cell or a eukaryotic cell. Also provided herein is a modified PFK-1 polypeptide expressed by the host cell.

In some embodiments, the vector is a viral or plasmid vector. In some embodiments, the viral vector is a DNA or RNA viral vector. Exemplary viral vectors include, but are not limited to, a vaccinia, adenovirus, adeno-associated virus (AAV), retrovirus, or herpesvirus vector.

In some embodiments, an isolated nucleic acid molecule encoding a modified PFK-1 polypeptide provided herein is inserted into an expression vector and expressed in a host cell or a non-cell extract. In some embodiments, an isolated nucleic acid molecule encoding a modified PFK-1 polypeptide provided herein is operatively linked to a promoter for expression of the encoding polypeptide in a cell or non-cell extract. In some embodiments, the promoter is a constitutive promoter. In some embodiments, the promoter is an inducible promoter.

In some embodiments, the nucleic acid molecule encoding a modified PFK-1 polypeptide provided herein is "exogenous" to a cell, which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference.

Methods for the expression of a protein in a cell are well known in the art and include, for example, expression in cells, such as animal and plant cells. Exemplary animal cells for the expression of modified PFK-1 polypeptide provided herein include but are not limited to bacteria, yeast, insect cells, amphibian, and mammalian cells, such as for example, human, primate, rodent, bovine, and ovine cells. In some embodiments, the nucleic acid encoding the modified PFK-1 is integrated into the genome of the host cell.

In some embodiments, a method for the expression of a modified PFK-1 polypeptide provided herein comprises culturing a host cell containing an expression vector encoding a modified PFK-1 polypeptide such that the modified PFK-1 polypeptide is produced by the cell. In some methods, the nucleic acid encoding as mutant polypeptide is connected to nucleic acid encoding a signal sequence such that the signal sequence is expressed as a fusion peptide with the modified PFK-1 polypeptide. In some embodiments the signal sequence allows for the secretion of the modified PFK-1 polypeptide by the host cell.

In some embodiments the modified PFK-1 polypeptide is isolated from a host cell expressing the mutant polypeptide.

In some embodiments an extract is prepared from the host cell and the modified PFK-1 polypeptide is isolated by purification methods such as but not limited to chromatography or immunoaffinity with an antibody that is specific for PFK-1 polypeptides or specific to the modified PFK-1 polypeptide in particular.

Therapeutic Treatment

In one aspect, the invention provides a method of reducing cancer formation or cancer progression. In some embodiments, the method comprises administering to a cancer cell an effective amount of (i) a therapeutic anti-cancer agent identified by a method comprising: a) contacting a cancer cell that expresses PFK-1 with a candidate agent; and b) identifying the candidate agent as a therapeutic anti-cancer agent when the cell exhibits a decreased level of phosphofructokinase 1 (PFK-1) glycosylation relative to a control cell upon contacting said candidate agent; (ii) a therapeutic anti-cancer agent that specifically reduces glycosylation at serine 529 of PFK-1; or (iii) a therapeutic anti-cancer agent that binds to a site encompassing serine 529. In some embodiments, the method comprises administering to a cancer cell an effective amount of a therapeutic anti-cancer agent that specifically increases PFK-1 expression or activity to counteract the effects of PFK-1 glycosylation. In some embodiments, the method comprises administering to a cancer cell an effective amount of a therapeutic anti-cancer agent that activates the glycosylated form of PFK-1 to counteract the effects of glycosylation without decreasing the level of PFK-1 glycosylation.

In one aspect, the invention provides a method of inducing cancer cell death. In some embodiments, the method comprises contacting the cancer cell with an effective amount of (i) a therapeutic anti-cancer agent identified by a method comprising: a) contacting a cancer cell that expresses PFK-1 with a candidate agent; and b) identifying said candidate agent as a therapeutic anti-cancer agent when the cell exhibits a decreased level of phosphofructokinase 1 (PFK-1) glycosylation relative to a control cell upon contacting said candidate agent; (ii) a therapeutic anti-cancer agent that specifically reduces glycosylation at serine 529 of PFK-1; or (iii) a therapeutic anti-cancer agent that binds to a site encompassing serine 529. In some embodiments, the method comprises contacting a cancer cell an effective amount of a therapeutic anti-cancer agent that specifically increases PFK-1 expression or activity to counteract the effects of PFK-1 glycosylation. In some embodiments, the method comprises contacting a cancer cell with an effective amount of a therapeutic anti-cancer agent that activates the glycosylated form of PFK-1 to counteract the effects of glycosylation without decreasing the level of PFK-1 glycosylation.

In one aspect, the invention provides a method of reducing PFK-1 glycosylation at serine 529 in a cell. In some embodiments, the method comprises contacting a cell with an agent that reduces glycosylation at serine 529.

In another aspect, the invention provides a method of increasing PFK-1 activity in a cell. In some embodiments, the method comprises contacting the cell with an agent that reduces PFK-1 glycosylation thereby reducing PFK-1 activity. In some embodiments, the method comprises contacting a cancer cell with an agent that specifically increases PFK-1 expression or activity to counteract the effects of PFK-1 glycosylation. In some embodiments, the method comprises contacting a cancer cell with an agent that activates the glycosylated form of PFK-1 to counteract the effects of glycosylation without decreasing the level of PFK-1 glycosylation.

Any of the agents described herein are suitable for practice one or more treatment methods disclosed. Non-limiting examples include antibodies specifically bind to PFK-1.

Decrease in cancer formation or cancer progression, or increase in cancer cell death, can be measured using well-known methods. In some embodiments, decrease in cancer formation or cancer progression, or increase in cancer cell death, can be measured using in vivo mouse models such as a xenograft model (e.g., SCID, SCID/beige or NOD/SCID mice). The effects of a candidate agent can be evaluated by many means known to those skilled in the art, e.g., microscopy for quantitative or qualitative measures of alterations in morphological features, e.g., tube or blood vessel formation, measurement of changes in RNA or protein levels for angiogenesis or tumorigenesis-associated sequences, measurement of RNA stability, identification of downstream or reporter gene expression (CAT, luciferase, β-gal, GFP and the like), e.g., via chemiluminescence, fluorescence, colorimetric reactions, antibody binding, inducible markers, etc. In addition, increase in cancer cell death can be measured by, e.g., increased chromatin condensation, increased internucleosomal DNA fragmentation and/or TUNEL staining. In some embodiments, increase in cancer cell death can be measured by, e.g., increased mitochondrial swelling and/or cytoplasmic vacuolation.

In some embodiments, treatment with a therapeutic anti-cancer agent decreases the propensity or likelihood for cancer formation or cancer progression of a cell or tissue (e.g., a cell or tissue having PFK-1 glycosylation) by about or more than about 5%, 10%, 15%, 20%, 25%, 30%, 35%, 40%, 45%, 50%, 55%, 60%, 70%, 80%, 90%, 95%, 96%, 97%, 98%, 99%, or more compared to a similar untreated cell or tissue. In some embodiments, treatment with an inhibitor of metastasis decreases the propensity or likelihood for cancer formation or cancer progression of a cell or tissue (e.g., a cell or tissue having PFK-1 glycosylation) by about or more than about 2-fold, 3-fold, 4-fold, 5-fold, 6-fold, 7-fold, 8-fold, 9-fold, 10-fold, 20-fold, 50-fold, 100-fold, 1000-fold, or more compared to a similar untreated cell or tissue. In some embodiments, treatment with a therapeutic anti-cancer agent increases the propensity or likelihood for cancer cell death of a cancerous cell or tissue (e.g., a cell or tissue having PFK-1 glycosylation) by about or more than about 5%, 10%, 15%, 20%, 25%, 30%, 35%, 40%, 45%, 50%, 55%, 60%, 70%, 80%, 90%, 95%, 96%, 97%, 98%, 99%, or more compared to a similar untreated cell or tissue. In some embodiments, treatment with an inhibitor of metastasis increases the propensity or likelihood for cancer cell death of a cancerous cell or tissue (e.g., a cell or tissue having PFK-1 glycosylation) by about or more than about 2-fold, 3-fold, 4-fold, 5-fold, 6-fold, 7-fold, 8-fold, 9-fold, 10-fold, 20-fold, 50-fold, 100-fold, 1000-fold, or more compared to a similar untreated cell or tissue. In some embodiments, treatment with a therapeutic anti-cancer agent decreases the numbers of cancer cells or cancer cell colonies formed by about or more than about 5%, 10%, 15%, 20%, 25%, 30%, 35%, 40%, 45%, 50%, 55%, 60%, 70%, 80%, 90%, 95%, 96%, 97%, 98%, 99%, or more compared to a similar untreated cell or tissue. In some embodiments, treatment with a therapeutic anti-cancer agent decreases the numbers of cancer cells or cancer cell colonies formed by about or more than about 2-fold, 3-fold, 4-fold, 5-fold, 6-fold, 7-fold, 8-fold, 9-fold, 10-fold, 20-fold, 50-fold, 100-fold, 1000-fold, or more compared to a similar untreated cell or tissue.

In some embodiments, the agent (e.g., the therapeutic anti-cancer agent) is an agent that binds to serine 529 of PFK-1 and blocks glycosylation. In some embodiments, the agent (e.g., the therapeutic anti-cancer agent) is an agent that binds to a site adjacent to serine 529 of PFK-1 thereby reduces glycosylation at serine 529. In some embodiments, the agent (e.g., the therapeutic anti-cancer agent) is an antibody or antigen-binding antibody fragment thereof. In some embodiments, the antibody or antigen-binding antibody fragment thereof specifically binds to an epitope comprising serine 529 of PFK-1. Preferably, the antibody or antigen-binding antibody fragment thereof specifically binds to an epitope comprising non-glycosylated serine 529 of PFK-1. In some embodiments, the antibody or antigen-binding antibody fragment thereof binds to an epitope adjacent to non-glycosylated serine 529 of PFK-1 thereby reduces glycosylation at serine 529. In some embodiments, the antibody is a monoclonal antibody, a humanized antibody, or a human antibody.

Methods of treatment employing antibodies as therapeutic agents are known in the art, with specific treatment regimens selected based on a variety of parameters, including but not limited to physical characteristics of the subject (e.g. height, weight, sex, and age), type and stage of disease, and whether or not treatment includes additional therapeutic agents.

Various delivery systems are known and can be used to administer an agent of the invention, e.g., encapsulation in liposomes, microparticles, microcapsules, expression by recombinant cells, receptor-mediated endocytosis (see, e.g., Wu and Wu, (1987), *J. Biol. Chem.* 262:4429-4432), construction of a therapeutic nucleic acid as part of a retroviral or other vector, etc. Methods of delivery include but are not limited to intra-arterial, intra-muscular, intravenous, intra-nasal, and oral routes. In a specific embodiment, it may be desirable to administer the pharmaceutical compositions of the invention locally to the area in need of treatment; this may be achieved by, for example, and not by way of limitation, local infusion during surgery, by injection, or by means of a catheter.

Administration of the selected agent can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician.

The preparation of pharmaceutical compositions of this invention is conducted in accordance with generally accepted procedures for the preparation of pharmaceutical preparations. See, for example, *Remington's Pharmaceutical Sciences* 18th Edition (1990), E. W. Martin ed., Mack Publishing Co., PA. Depending on the intended use and mode of administration, it may be desirable to process the active ingredient further in the preparation of pharmaceutical compositions. Appropriate processing may include mixing with appropriate non-toxic and non-interfering components, sterilizing, dividing into dose units, and enclosing in a delivery device.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or aerosol when used with an appropriate aerosolizer device.

Liquid pharmaceutically acceptable compositions can, for example, be prepared by dissolving or dispersing a polypeptide embodied herein in a liquid excipient, such as water, saline, aqueous dextrose, glycerol, or ethanol. The composition can also contain other medicinal agents, pharmaceutical agents, adjuvants, carriers, and auxiliary substances such as wetting or emulsifying agents, and pH buffering agents.

Where desired, the pharmaceutical compositions can be formulated in slow release or sustained release forms, whereby a relatively consistent level of the active compound are provided over an extended period.

Kits

In one aspect, the invention provides kits containing any one or more of the elements disclosed in the above methods and compositions. In some embodiments, a kit comprises a composition of the invention, in one or more containers. A kit of the invention may comprise one or more compositions of the invention and instructions instructing the use of said composition. For example, a kit may comprise one or more of the following: reagents suitable for detecting a PFK-1 glycosylation, such as an oligonucleotide or a protein binding agent; one or more buffers for a detection reaction; a protocol for carrying out an assay; optionally any additional reagents; and optionally any reference standard. In some embodiments, a kit comprises one or more of the following: an expression vector and/or transgenic cell; one or more buffers; one or more standards; a protocol for the use of said expression vector and/or transgenic cell; and optionally any other reagents for an assay.

The invention can be further understood by reference to the following examples, which are provided by way of illustration and are not meant to be limiting.

EXAMPLES

Example 1

Cell Culture and Tumor Tissues

The cell lines 293T, A549, H1299, LNCaP, MCF-10A, MCF-7, MDA-mb-231, PrEc, DU145, HepG2, HCT15, HeLa and human dermal fibroblasts were obtained from ATCC and cultured according to ATCC protocols. MCF-10AT cells were obtained from the Barbara Ann Karmanos Cancer Institute (Detroit, Mich.). MCF10-DCIS.com cells were purchased from Asterand, Inc. Both MCF-10AT and MCF10-DCIS.com cells were cultured in Dulbecco's modified Eagle media (DMEM)/F12 (1:1) medium (Invitrogen) with 5% horse serum (Invitrogen), 0.029 M sodium bicarbonate, 10 mM HEPES, 10 µg ml$^{-1}$ insulin (Sigma-Aldrich), and 0.5 µg ml$^{-1}$ hydrocortisone (Sigma-Aldrich)

Breast tumor tissues and matching tumor-adjacent normal tissues from the same patient were obtained from Agios Pharmaceuticals (Cambridge, Mass.). Lung tumor tissues and matching tumor-adjacent normal tissues from the same patient were obtained from the Tumor and Tissue Bank, University of Massachusetts Medical School.

Example 2

Immunoblotting

SDS lysis buffer (1% SDS, 50 mM Tris-HCl, pH 7.5, 100 mM NaCl, 10 µM PUGNAc, and Complete™ protease inhibitors (Roche)) was used to lyse the cells, and the lysate was resolved by 4-12% SDS-PAGE, transferred to Immobilon-FL PVDF membrane (Millipore), and immunoblotted with the indicated antibodies. Antibodies used in this study were obtained from the following sources: O-GlcNAc antibody (RL-2, Affinity BioReagents, 1:1000 working dilution), PFK1 antibody (Santa Cruz Biotechnology, 1:1000 working dilution), Flag antibody (Sigma-Aldrich, 1:5000 working dilution), Myc antibody (Sigma-Aldrich, 1:5000 working dilution), OGT antibody (DM-17, Sigma-Aldrich, 1:1000 working dilution), OGA antibody (Sigma-Aldrich, 1:1000 working dilution), and tubulin antibody (Sigma-Aldrich, 1:5000 working dilution). The BCA protein assay (Pierce) was used to measure all protein concentrations. Western blots were visualized and quantified using an Odyssey Infrared Imaging System (LI-COR Biosciences, Version 2.1).

Example 3

Modulation of Cellular O-GlcNAc Levels

Cellular O-GlcNAc levels were modulated by OGT overexpression or PUGNAc treatments. For OGT overexpression experiments, H1299, A549, or 293T cells were transiently transfected with a pDEST26/HA-OGT vector (provided by L. Wells) using Lipofectamine 2000 reagent (Invitrogen) according to the manufacturer's protocol. Cells were collected 36 h after transfection, lysed in SDS lysis buffer containing 5 µM O-(2-acetamido-2-deoxy-D-glucopyranosylidene) amino Nphenylcarbamate (PUGNAc; Toronto Research Chemicals), and immunoblotted for OGlcNAc levels. For PUGNAc treatments to enhance O-GlcNAc levels, cells cultured in DMEM high glucose media (with 10% FBS, penicillin/streptomycin (100 U ml$^{-1}$); Invitrogen) or RPMI 1640 media (with 10% FBS, penicillin/streptomycin (100 U ml$^{-1}$); Invitrogen) were treated with PUGNAc (100 µM) for 9 h and then immunoblotted for OGlcNAc levels. OGT overexpression and PUGNAc treatment did not affect cell viability, as determined by trypan blue exclusion.

Example 4

Cellular Metabolism Measurements

The conversion of 5-$^3$H-glucose to $^3$H$_2$O was followed to measure the cellular glycolytic rates. Briefly, cells (H1299, A549, 293T, and various H1299 PFK1 rescue cells, in the presence or absence of OGT overexpression) were cultured overnight in appropriate complete culture media (DMEM or RPMI 1640, supplemented with 10% FBS, penicillin/streptomycin (100 U ml$^{-1}$)) at a concentration of 2×10$^6$ cells per well in a 6-cm tissue culture plate. The cells were washed once in phosphate buffered saline (PBS) and incubated in Krebs buffer (126 mM NaCl, 2.5 mM KCl, 25 mM NaHCO$_3$, 1.2 mM NaH$_2$PO$_4$, 1.2 mM MgCl$_2$, 2.5 mM CaCl$_2$) for 30 min at 37° C. The buffer was replaced with fresh Krebs buffer containing 10 mM glucose dosed with 10 µCi of 5-$^3$H-glucose. After 1 h, a diffusion chamber was used to determine the amount of $^3$H$_2$O generated. Cellular lactate production was measured using a colorimetric-based assay kit (BioVision) according to the manufacturer's protocol. Briefly, the cells described above were cultured in complete media containing 10 mM glucose overnight. On the day of the experiment, the media was replaced with fresh media (without FBS). After 1 h, lactate levels were measured from media aliquots on a Victor 3 micro-plate reader (Perkin Elmer) and normalized for cell number. Intracellular ATP concentrations were measured using CellTiter-Glo Luminescent Assay kit (Promega). Luminescence was recorded on a Victor 3 micro-plate reader and normalized to protein concentration. For experiments involving PUGNAc treatments, PUGNAc (100 µM) was added to the cell culture medium 9 h before the measurements were carried out. For experiments involving hypoxic treatments, cells were cultured at 30% confluency under hypoxic conditions (0.5% O$_2$, 5% CO$_2$, and 94.5% N$_2$) at 37° C. for 24 h before the measurements were carried out.

Example 5

Generation of PFK1 Expression Vectors for Transient Mammalian Cell Expression

Flag-tagged WT human PFK1 (L isoform) cDNA (ATCC, NCBI accession #NM_002626) was cloned into the expression vector pFLAG-CMV-6a (Sigma-Aldrich). Myc-tagged PFKP and PFKM expression clones (both subcloned in pCMV6-Entry) were obtained from Origene. The S529A and T527A PFKL mutants were generated using the QuikChange II Site Directed Mutagenesis Kit (Agilent Technologies).

Example 6

Generation of Stable Cell Lines

In order to generate the PFK1 rescue H1299 cell lines, Flagtagged WT PFK1 and S529A PFK1 (L isoform) were cloned into the expression vector pLenti6.2/V5-DEST (Invitrogen). The PFK1 sequence was made resistant to the PFK1 shRNA by introducing silent mutations (lower case: CCTAGTaGGaagCATCGAcAA (SEQ ID NO: 5)) using the QuikChange II Site Directed Mutagenesis Kit. Lentiviruses were produced from these constructs using a three-plasmid packaging system. H1299 cells were infected with the lentiviruses and selected with blasticidin (10 µg ml$^{-1}$, Invitrogen) for 1 week. To knockdown endogenous PFK1 in these cells, the shRNA sequence 5'-CCTAGTGGGCTCCATCGATAA-3' (SEQ ID NO: 6) (obtained from the RNAi Consortium) or the corresponding scramble sequence 5'-AGTCCTTAGTCGAATCAGCCG-3' (SEQ ID NO: 7) was inserted into the vector pLKO.1 (Addgene). Lentiviruses containing the PFK1 or scramble shRNA construct were obtained as describe above. H1299 cells stably expressing WT or S529A Flag-tagged PFK1 were infected with lentiviruses containing the PFK1 or scramble shRNA constructs and selected with puromycin (2 µg ml-1) for 2 weeks.

In order to stably knockdown OGT in 293T and H1299 cells, the following OGT targeting shRNA sequence was inserted into the pLKO.1 vector: 5'-CCAAACTTTCTGGATGCTTAT-3' (SEQ ID NO: 8). The scramble sequence was 5'-TTCGATCTCAATTGCTATCGA-3' (SEQ ID NO: 9). Cells were infected with lentiviruses containing the OGT or scramble shRNA constructs and selected with puromycin (2 µg ml$^{-1}$) as described above. OGT expression was knocked down by approximately 75% using shRNA, and no deleterious effects on cell viability were observed over the 24 h period of our experiments, as determined by trypan blue exclusion and ATP levels.

In order to obtain WT or S529A PFK1 (L isoform) H1299 rescue cells overexpressing OGT, human OGT cDNA (nucleocytoplasmic long form, ncOGT, Open Biosystems, NCBI accession #BC014434.1) was cloned into the pcDNA3.1/Hygro vector (Invitrogen), transfected into cells using Lipofectamine 2000 reagent, and selected with hygromycin (400 μg ml$^{-1}$) for 2 weeks. Colonies were selected for the highest expression levels of OGT, as determined by immunoblotting.

Example 7

Analysis of PFK1 Glycosylation

To carry out chemoenzymatic labeling and biotinylation of proteins in cell lysates, cell lines and tissues were first lysed in lysis buffer (1% SDS, 50 mM Tris-HCl, pH 7.5, 100 mM NaCl, 10 μM PUGNAc, and Complete™ protease inhibitors (Roche)). The cell lysate (400 μg) was then labeled according to the Click-iT O-GlcNAc Enzymatic Labeling System protocol (Invitrogen) and conjugated with an alkyne-biotin compound as per the Click-iT Protein Analysis Detection Kit protocol (Invitrogen). Control experiments were carried out in parallel in the absence of the labeling enzyme GalT. Biotinylated lysates were precipitated using methanol and chloroform as described in the Click-iT Protein Analysis Detection Kit protocol, resolubilized in 1% SDS, and neutralized with an equal volume of neutralization buffer (6% NP-40, 100 mM Na$_2$HPO$_4$, 150 mM NaCl). Lysates were then incubated with streptavidin resin (Pierce) with end-to-end rotation at 4° C. overnight. Resin was then washed 5 times with 1 ml of low salt buffer (100 mM Na$_2$HPO$_4$, 150 mM NaCl, 0.1% SDS, 1% Triton X-100, 0.5% sodium deoxycholate) and 5 times with 1 ml of high salt buffer (100 mM Na$_2$HPO$_4$, 500 mM NaCl, 0.2% Triton X-100). Biotinylated proteins were eluted by boiling the resin in 50 mM Tris-HCl pH 6.8, 2.5% SDS, 100 mM DTT, 10% glycerol and 20 mM biotin for 10 min. To quantify the percentage of glycosylation, the intensity of the band eluted from resin (the glycosylated protein fraction) and the band from the input (the total protein) were measured. The ratio of the intensity (corrected with the percentage of protein input) was taken as the glycosylation stoichiometry.

To carry out chemoenzymatic labeling of PFK1 with a 5-kD PEG mass tag, the labeled lysates were subjected to 4-12% SDS-PAGE and immunoblotted. The percentage of glycosylation on Flag-tagged PFK1 was determined by using an antibody to Flag. To quantify the percentage of glycosylation, the intensity of the PEG-shifted band (the glycosylated protein fraction) and the unshifted band (the non-glycosylated protein fraction) were measured and the ratio of the intensity of the glycosylated protein fraction over the intensity of the total protein (glycosylated protein fraction plus non-glycosylated protein fraction) was taken as the glycosylation stoichiometry.

Example 8

PFK1 Purification and Enzymatic Assay

Lipofectamine 2000 was used to transiently transfect Human PFK1 isoforms (Flag-tagged PFKL, Myc-tagged PFKP and Myc-tagged PFKP) into 293T cells. To purify Flag-tagged PFKL, cells were lysed 36 h after transfection in Triton X-100 lysis buffer (50 mM Tris-HCl, pH 7.4, 150 mM NaCl, 1% Triton X-100, 5 μM PUGNAc and Complete™ protease inhibitor cocktail). The lysate (7 mg) was diluted to 2 mg ml$^{-1}$ with NETFS buffer (100 mM NaCl, 50 mM Tris-HCl pH 7.4, 5 mM EDTA, 5 μM PUGNAc and Complete™ protease inhibitor cocktail). The sample was incubated with Flag M2 immunoaffinity resin (400 μl; Sigma-Aldrich) at 4° C. overnight with end-to-end rotation. The gel was then washed twice with 10 ml of NETFS containing 1% Triton X-100, and twice with 10 ml of NETFS. The Flag-PFK1 protein was eluted with the 3 Å~Flag peptide (Sigma-Aldrich) in NETFS buffer according to the manufacturer's protocol. The eluent was further purified and concentrated using an Amicon Ultra Centrifugal Filter (10-kD molecular weight cutoff; Millipore) in a buffer containing 50 mM Tris-HCl pH 7.5, 100 mM KCl, 5 mM MgCl2 and 5% glycerol.

In order to purify Myc-tagged PFKP and PFKM, the same lysis buffer was used to lyse transfected cells as described above. The samples were incubated with Myc immunoaffinity resin (100 μl; Sigma-Aldrich) at 4° C. overnight with end-to-end rotation. The resin was then washed three times with 2 ml of PBS. The Myc-PFK1 proteins were eluted with 5 ml of 0.1 M NH$_4$OH according to the manufacturer's protocol. The eluent was neutralized with 1 N acetic acid and further purified and concentrated using an Amicon Ultra Centrifugal Filter (10-kD molecular weight cutoff) in a buffer containing 50 mM Tris-HCl pH 7.5, 100 mM KCl, 5 mM MgCl$_2$ and 5% glycerol.

In order to measure PFK1 activity, a reaction was performed using either cell lysate (20 μg) or recombinant purified PFK1 (0.1 μg) in 1 ml of reaction buffer containing 50 mM Tris-HCl pH 7.5, 100 mM KCl, 5 mM MgCl$_2$, 1 mM ATP, 0.2 mM NADH, 5 mM Na$_2$HPO$_4$, 0.1 mM AMP, 1 mM NH$_4$Cl, 5 mM fructose-6-phosphate, 5 U of triose phosphate isomerase (Sigma-Aldrich), 1 U of aldolase (Sigma-Aldrich) and 1 U of α-glycerophosphate dehydrogenase (Sigma-Aldrich). Absorbance was recorded at 340 nm at room temperature every 15 s for 10 min using a Uvikon UV-Vis spectrophotometer (Research Instruments International). One unit of PFK1 activity is defined as the amount of enzyme that catalyzes the conversion of 1 μmol of fructose-6-phosphate to fructose-1,6-bisphosphate per min.

In order to determine the activation of PFK1 by F-2,6-BP (Sigma-Aldrich) over the indicated concentrations, reactions were performed in similar buffer conditions as described above except that an inhibitory concentration of ATP (3 mM) was used. In experiments to determine the allosteric regulation by ATP, reactions were performed in similar buffer conditions with a fixed F-2,6-BP concentration of 100 nM, and ATP concentrations from 0.05 to 10 mM.

Example 9

Enzymatic Assays of Hexokinase (HK), Phosphoglycerate Kinase (PGK) and Pyruvate Kinase (PK)

To determine enzyme activities, endogenous HK, PGK and PK from 293T cell lysates were collected. HK reactions were carried out using 20 μg of 293T cell lysate in 1 ml of reaction buffer containing 50 mM Tris-HCl pH 7.5, 10 mM MgCl$_2$, 0.6 mM ATP, 100 mM glucose, 0.2 mM NAD$^+$, and 10 U of glycerol-6-phosphate dehydrogenase (Sigma-Aldrich). Absorbance was recorded at 340 nm at room temperature every 15 s for 10 min as described above. PGK reactions were carried out using 20 μg of 293T cell lysate in 1 ml of reaction buffer containing 50 mM Tris-HCl pH 7.5, 5 mM MgCl$_2$, 5 mM ATP, 0.2 mM NADH, 10 mM glycerol-3-phosphate, and 10 U of GAPDH (Sigma-Aldrich). Absorbance was recorded at 340 nm at room temperature every 15 s for 10 min as described above. PK reactions were carried out with 10 μg of 293T cell lysate in 1 ml of reaction buffer containing 50 mM Tris-HCl pH 7.5, 100 mM KCl, 5 mM MgCl$_2$, 0.6 mM ADP, 0.5 mM PEP, 0.18 mM NADH, 0.01 mM fructose-1,6-bisphosphate, and 10 U of lactate dehydrogenase (Sigma-Aldrich). Absorbance was recorded at 340 nm at room temperature every 15 s for 10 min.

Example 10

Hypoxic and Glucose Deprivation Treatment

Hypoxia experiments were performed using a sealed hypoxia chamber (Proox Model 110, BioSpherix, Ltd.) filled with 0.5% O$_2$, 5% CO$_2$, and 94.5% N$_2$ at 37° C. and 30% cell confluency for the indicated periods of time. For glucose deprivation experiments, H1299 cells were seeded at a density of 1 Å~10$^5$ cells ml$^{-1}$ in a 6-well tissue culture plate. The cells were cultured in RPMI 1640 media overnight before switching to RPMI 1640 media without glucose (Sigma-Aldrich) for the indicated periods of time.

Example 11

Mouse T Lymphocyte Isolation and Activation

The spleens were dissected from mice (C57BL/6, male, Charles River Laboratories) and placed in a clean 10-cm tissue culture dish containing 10 ml of RPMI 1640 media supplemented with 5% FBS and penicillin/streptomycin (100 U ml$^{-1}$). The spleens were disrupted, and the cells were passed through a 40-micron cell strainer (Fisher Scientific) and collected by centrifugation at 1500 rpm for 8 min. The supernatant was discarded, and the cells were resuspended in 6 ml of PBS buffer containing 0.1% BSA and 2 mM EDTA. Cell numbers were counted under a microscope by trypan blue staining T cells were then isolated using the Dynal Mouse T Cell Negative Isolation Kit (Invitrogen) according to the manufacturer's protocol and plated at a density of 1 Å~10$^6$ cells ml$^{-1}$ in RPMI 1640 media supplemented with 5% FBS and penicillin/streptomycin (100 U ml$^{-1}$).

Dynabeads Mouse TActivator CD3/CD28 (Invitrogen), as well as 30 U ml$^{-1}$ of recombinant mouse interleukin-2 (Invitrogen), was used to activate and expand T cells according to the manufacturer's recommendation. The cells were incubated in a humidified CO$_2$ incubator at 37° C. for 72 h. Cell numbers were determined by measuring intracellular ATP levels using the CellTiter-Glo Luminescent Cell Viability Assay Kit (Promega) according to the manufacturer's protocol.

Example 12

Culturing of Human Dermal Fibroblasts and Analysis of Cell Cycle by Flow Cytometry Primary human dermal fibroblasts (ATCC) were maintained in DMEM media supplemented with 10% FBS and penicillin/streptomycin (100 U ml$^{-1}$). Proliferating cells were seeded at a density of 1 Å~10$^5$ cells ml$^{-1}$ and subcultured when they reached confluency. Cells were made quiescent via contact inhibition by maintaining them at confluency in the above DMEM media for 1 week. Cells were harvested in PBS buffer containing 5% FBS, pelleted, resuspended in ice-cold 70% ethanol (1 ml per 1 Å~10$^6$ cells), and stored at 4° C. overnight. Cells were pelleted, washed twice with PBS, and resuspended in PBS containing 100 µg ml$^{-1}$ ribonuclease A (Sigma-Aldrich). Samples were incubated at room temperature for 1 h. Propidium iodide (PI, Sigma-Aldrich) was added to the samples at a final concentration of 50 µg ml$^{-1}$, and the samples were incubated in the dark at room temperature for 1 h.

A Becton Dickinson FACSCalibur flow cytometer equipped with a 488 nm argon laser was used to analyze the treated samples. Propidium iodide was excited at 488 nm, and emitted fluorescence was collected and triggered on detector FL2 with a bandpass filter of 585/42 nm. Samples were gated by forward scatter against right angle light scatter and a secondary gate placed around the single cell population on a pulse area versus pulse width FL2 signal processing dot plot to gate out doublets. At least 10,000 cells were collected, and the cell cycle distribution was analyzed with FlowJo off-line software (Treestar).

Example 13

Site-Mapping of PFK1 Glycosylation

Lipofectamine 2000 was used to cotransfect Flag-tagged PFKL and HA-tagged OGT into 293T cells. After 36 h, Flag-tagged PFKL was isolated from the cells using Flag M2 immunoaffinity resin. The bound protein was eluted in a buffer (4% SDS and 100 mM Tris-HCl, pH 8.0). After SDS-PAGE (4-12% Bis-Tris gels) and staining with Bio-Safe Coomassie blue R250 Stain (0.25%; Bio-Rad), the PFKL protein band was excised and manually digested ingel with chymotrypsin. The extracted peptides were lyophilized and reconstituted in 1× binding buffer (Glycoprotein Isolation Kit WGA, Thermo Scientific) and incubated with WGA lectin resin (Glycoprotein Isolation Kit WGA, Thermo Scientific) at 4° C. with end-to-end rotation overnight. The resin was washed according to the manufacturer's protocol, and the bound peptides were eluted with the provided elution buffer. The eluent was further purified by reverse-phase HPLC (Agilent 1100) using a preparative reverse-phase column (Agilent Eclipse XDB-C18; 5 µm, 9.4×250 mm) and a gradient of 5-30% B buffer over 20 min at 4 ml min$^{-1}$ (A buffer, 0.5% aqueous AcOH; B buffer, 100% MeCN). Fractions eluting between 5-12 min were collected, pooled, lyophilized, and subjected to ETD-MS analysis.

Example 14

PFK1 Structure Modeling

The following PDB files were used to model the F-2,6-BP binding site in rabbit PFK: *Saccharomyces cerevisiae* PFK α$_4$β$_4$ octamer cocrystallized with F-2,6-BP (3O8O, chains C, D), rabbit skeletal muscle PFK crystallized without F-2,6-BP (3O8L). The rabbit PFK homology model was determined by aligning chain B of the rabbit PFK with chain C of the yeast PFK, and aligning chain A of the rabbit PFK with chain D of the yeast PFK (RMSD: 1.684 and 1.727 Å, respectively) and minimizing this structure as previously described. F-2,6-BP was extracted from the PBD file 3O8O, hydrogen atoms were added, and charges were assigned to each atom using the charge equilibration (QEq) method. The F-2,6-BP was fully minimized under conditions of Surface Generalized Born (SGB) continuum solvation, was combined with the minimized rabbit PFK homology model, and the combined structure was minimized under conditions of SGB continuum solvation. Residues within 5 Å of F-2,6-BP were considered part of the F-2,6-BP binding site.

In order to model O-GlcNAc glycosylation of rabbit PFK at Ser$^{530}$, N-acetyl-glucosamine was extracted from PDB file 1E6Z (NAG 1) and was prepared as described for F-2,6-BP above. MoleculeGL was used to create 959 conformations of the O-GlcNAc residue, and each conformation was modeled into the minimized rabbit PFK homology model at $Ser^{530}$. Each of the glycosylated structures was minimized for 50 steps under conditions of SGB continuum solvation. Side chains within 4 Å of the O-GlcNAc residues in the top 50 lowest energy structures were optimized, and then the structures were fully minimized under conditions of SGB continuum solvation. The five lowest energy structures following complete minimization were considered as models of glycosylated PFK. Pymol was used to perform all alignments and distance measurements and to create the images. The final coordinates of the optimum structure are attached.

Example 15

Generation of Low and High Glycoforms of PFK1

293T cells were transiently transfected with Flag-tagged PFKL, Myc-tagged PFKP, or Myc-tagged PFKM. To enhance levels of glycosylation, the transfected cells were grown to 30% cell confluency under hypoxic conditions (0.5% $O_2$, 5% $CO_2$, and 94.5% $N_2$) at 37° C. for 24 h. Alternatively, 293T cells were transiently co-transfected with Flag-tagged PFKL and HA-OGT, and cultured in complete high glucose DMEM media under hypoxic conditions (1% $O_2$, 5% $CO_2$, and 94% $N_2$) at 37° C. for 24 h. PUGNAc (100 µM) was added to the cell culture 9 h before the cells were harvested. Forms of Flag-tagged PFKL, Myc-tagged PFKP, or Myc-tagged PFKM containing low glycosylation levels were obtained by culturing the transfected cells under normoxic conditions. PFK1 proteins were purified using Flag M2 or Myc immunoaffinity resin as described above. Similar experiments were performed using the Flag-tagged S529A mutant PFKL construct. Glycosylation levels were analyzed by chemoenzymatic labeling with a 5-kD mass tag, and PFK1 activities were measured on the purified proteins as described above.

Example 16

Analysis of PFK1 Oligomerization

Flag-tagged PFK1 (L isoform) was transiently expressed in 293T cells with or without co-expression of HA-tagged OGT. After 36 h, Flag-tagged PFK1 was isolated from the lysate using Flag M2 immunoaffinity resin and eluted with a 3 Å~Flag peptide as described above. The eluent was concentrated using Amicon Ultra Centrifugal Filters (10-kD molecular weight cutoff). Similarly, 293T cells expressing Flag-tagged PFK1 were treated with PUGNAc (100 µM, 12 h) or cultured under hypoxic conditions (0.5% $O_2$, 5% $CO_2$, and 94.5% $N_2$) at 37° C. for 24 h, before protein isolation. As a control, heat treatment of PFK1 in the presence or absence of 50 nM F-2,6-BP was performed at 50° C. for 30 min. The proteins were then subjected to native gel electrophoresis (Bio-Rad) and visualized by Coomassie blue staining as described above.

PFK1 oligomerization was analyzed by co-immunoprecipitation as follows: WT or S529A PFKL containing 3 consecutive Flag tags was cloned into the expression vector pCAG-3Flag (provided by B. Zhuang) and transiently expressed in 293T cells with or without co-expression of HA-tagged OGT. Cells were lysed 36 h after transfection in Triton X-100 lysis buffer. The Flag-tagged proteins were then immunoprecipitated using Flag M2 immunoaffinity resin as described above, eluted in 100 mM Tris-HCl, pH 8.0 containing 4% SDS, subjected to SDS-PAGE and PVDF transfer, and immunoblotted with the indicated antibodies.

Example 17

Analysis of the Pentose Phosphate Pathway (PPP) Activity, and Determination of NADPH and GSH Levels In order to determine PPP activity, $2 \times 10^6$ cells (WT or S529A PFK1 H1299 rescue cells, with or without OGT overexpression) were grown in a 6-cm culture plate in sodium bicarbonate free RPMI medium supplemented with 10% FBS, 20 mM HEPES, 5 mM glucose and 0.2 µCi of $[1-^{14}C]$-glucose or $[6-^{14}C]$-glucose (American Radiolabeled Chemicals). The cells were placed in a closed glass vial, the center of which was covered with filter paper soaked in 100 µl of 5% KOH, and incubated at 37° C. for 4 h. The filter paper was removed, and the radioactivity was determined using a LS 6500 Multi-Purpose Scintillation Counter (Beckman Coulter). PPP activity was calculated as the difference between the radioactivity levels of samples obtained from [1-14C]-glucose and samples obtained from $[6-^{14}C]$-glucose, normalized to cell number.

NADPH levels were determined using a colorimetric $NADP^+$/NADPH Quantitation Kit (BioVision) according to the manufacturer's protocol. The signal at 450 nm was recorded using a Victor 3 micro-plate reader and normalized to protein concentration. GSH levels were measured using a Glutathione Assay Fluorimetric Kit (Sigma-Aldrich) according to the manufacturer's procedure. Fluorimetric signal was recorded on a Victor 3 micro-plate reader and normalized to protein concentration.

Example 18

Cell Preparation for Metabolomic Analysis of PPP Flux

WT or S529A PFK1 H1299 rescue cells (with or without OGT overexpression) were seeded at a concentration of 200,000 cells per well in a 6-well tissue culture plate and grown in complete RPMI 1640 culture medium for 24 h. The medium was changed to RPMI 1640 medium supplemented with 5 mM glucose and 2 mM glutamine, and the cells were allowed to grow for 16 h. The cells were then incubated for 3 h with fresh RPMI 1640 medium supplemented with 5 mM glucose and 2 mM glutamine before replacing the unlabeled medium with the corresponding labeled medium (RPMI 1640 supplemented with 5 mM $[1,2-^{13}C]$-glucose and 2 mM glutamine). After incubation for 4 h, the medium was aspirated, and the cells were washed twice with cold PBS. Pre-chilled 80% aqueous methanol (−80° C.; 1 ml) was quickly added to each well. Cells were scraped off the well and transferred into microcentrifuge tubes. The extraction was repeated, and both fractions were combined and centrifuged at 20,000×g for 2 min. Supernatants were obtained and dried by speedvac.

Example 19

LC-MS and Flow-Injection-Analysis Mass Spectrometry for Metabolomics

Cell extracts obtained as described above were analyzed for relative abundance of $^{13}C$-metabolites by liquid chromatography-triple quadrupole mass spectrometry (LC-MS) using scheduled selective reaction monitoring (SRM) for each metabolite of interest, with the detector set to negative mode. Prior to injection, dried extracts were reconstituted in LC-MS grade water. LC separation was achieved by reverse-phase ion-pairing chromatography as described. Extracted metabolite concentrations were calculated from standard metabolite build-up curves using natural $^{12}C$ synthetic metabolites and normalized against cell number as well as the internal $^{13}C$-labeled metabolite standards added at the time of metabolite extraction. The relative percentage of PPP flux was calculated.

In order to acquire the data for flow-injection analysis for metabolomics, the platform consisting of an Agilent Series 1100 LC pump coupled to an Agilent 6520 Series Quadrupole Time-of-flight mass spectrometer (Agilent) equipped with an electrospray source operated in negative and positive mode. The flow rate was 150 µl min$^{-1}$ of mobile phase consisting of isopropanol/water (60:40, v/v) buffered with 5 mM ammonium carbonate at pH 8.5. Mass spectra were recorded from m/z 50 to 1000 with a frequency of 1.4 spectra/s for 0.48 min using the highest resolving power (4 GHz HiRes). All steps of data processing and analysis were performed with Matlab R2010b (The Mathworks, Natick) using functions native to the Bioinformatics, Statistics, Database, and Parallel Computing toolboxes.

Example 20

Measurement of Reactive Oxygen Species (ROS) Levels and $H_2O_2$-Mediated Cell Death The redox-sensitive dye 5(6)-chloromethyl-2'7'-dichloro-dihydrofluorescein diacetateacetyl ester (CM-H2DCFDA; Molecular Probes) was used to measure ROS levels in cell lines. Briefly, cells (H1299 cells with or without OGT overexpression) were cultured overnight at a concentration of 4×10$^5$ cells per well in a 12-well tissue culture plate in complete RPMI 1640 media supplemented with 10% FBS, penicillin/streptomycin (100 U ml-1). After treating cells with various concentrations of diamide (Sigma-Aldrich) as indicated for 10 min, fresh culture medium was added. The cells were then incubated with 10 µM CM-H$_2$DCFDA for 20 min and rinsed three times with PBS. The cells were lysed in 1% SDS and sonicated. The mixture was centrifuged (15,000×g, 2 min) to remove any cell pellets. 100-µl aliquots were taken, and the fluorescence intensity was measured on a Victor 3 micro-plate reader. Signal intensity was normalized to protein concentration.

A lactate dehydrogenase (LDH)-based toxicology assay (Sigma-Aldrich) was used to measure the percentage of cell death according to the manufacturer's protocol. Briefly, cells (H1299 cells with or without OGT overexpression) were cultured overnight at a concentration of 2×10$^5$ cells per well in a 96-well tissue culture plate. The culture media (complete RPMI 1640, supplemented with 10% FBS, penicillin/streptomycin (100 U ml$^{-1}$)) was replaced with fresh media without FBS, and the cells were treated with the indicated concentrations of $H_2O_2$ for 30 min. Control experiments without the $H_2O_2$ treatment were carried out in parallel for measuring total cell numbers. The percentage of cell death was determined by comparing the amount of cytoplasmic LDH released into the culture medium relative to the total cytoplasmic LDH, as determined by the reduction of NAD$^+$.

Example 21

Cell Proliferation Analysis

A CellTiter-Glo Luminescent Cell Viability Assay Kit (Promega) was used to perform cell proliferation assays. Cells were seeded at a concentration of 2,000 cells per well in a 96-well tissue culture plate. Luminescence was measured using a Victor 3 micro-plate reader. The luminescence signal measured from the cells 6 h after seeding was taken as the initial value, and measurements were performed every 24 h for 96 h.

Example 22

Xenograft Studies

Nude mice (nu/nu, male, 6-8 week old, Charles River Laboratories) were injected subcutaneously with 5×10$^6$ cells (resuspended in 200 µl of PBS) from each of the following H1299 rescue cell lines: Flag-tagged WT PFK1 rescue cells; Flagtagged S529A PFK1 rescue cells; Flag-tagged WT PFK1 rescue cells with OGT overexpression; and Flag-tagged S529A PFK1 rescue cells with OGT overexpression. Tumor growth was monitored every 3 days over a 7-week period. At the end of the seventh week, the tumors were harvested and weighed. Experiments were performed in accordance with the Caltech Institutional Animal Care and Use Committee guidelines.

Example 23

Effects of O-GlcNAcylation on Cellular Metabolism

Figure 5:
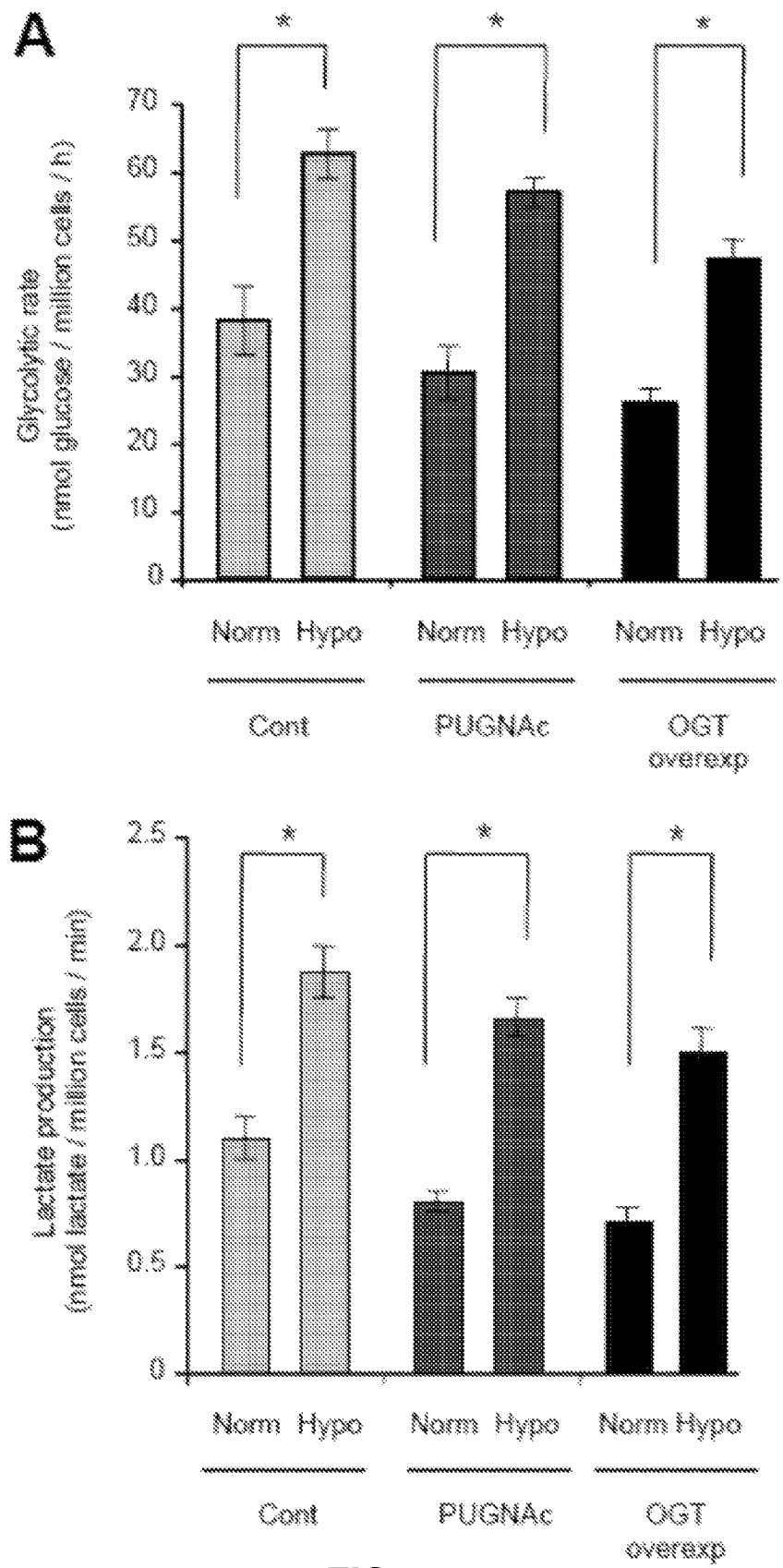
FIGS. 5A-B show bar graphs illustrating effects of O-GlcNAcylation on cellular metabolism in H1299 cells under normoxic (Norm) and hypoxic (Hypo) conditions.
Figure 6:
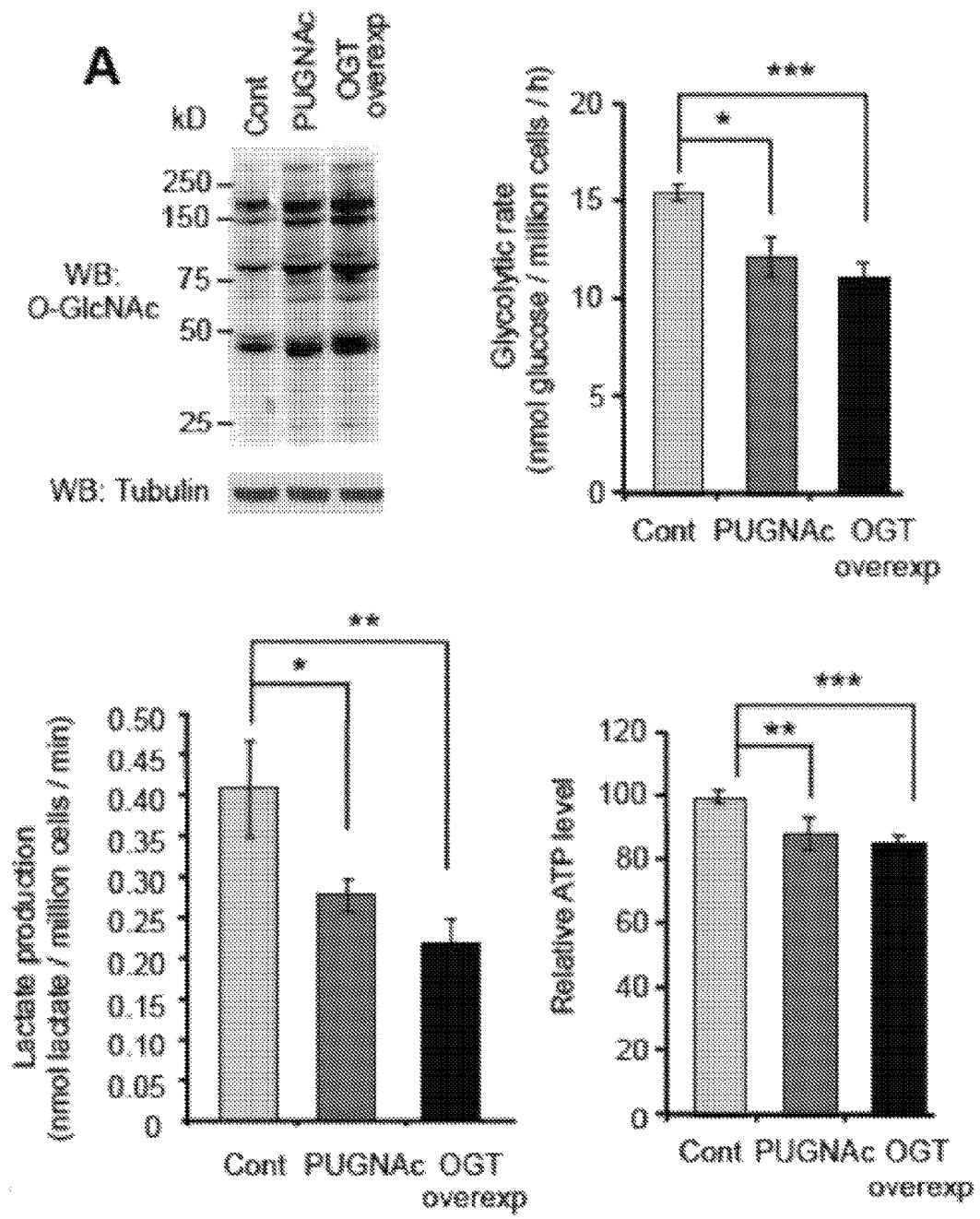
FIGS. 6A-B show immunoblots and bar graphs illustrating effects of O-GlcNAcylation on cellular metabolism in (A) A549 and (B) 293T cells.
Figure 6:
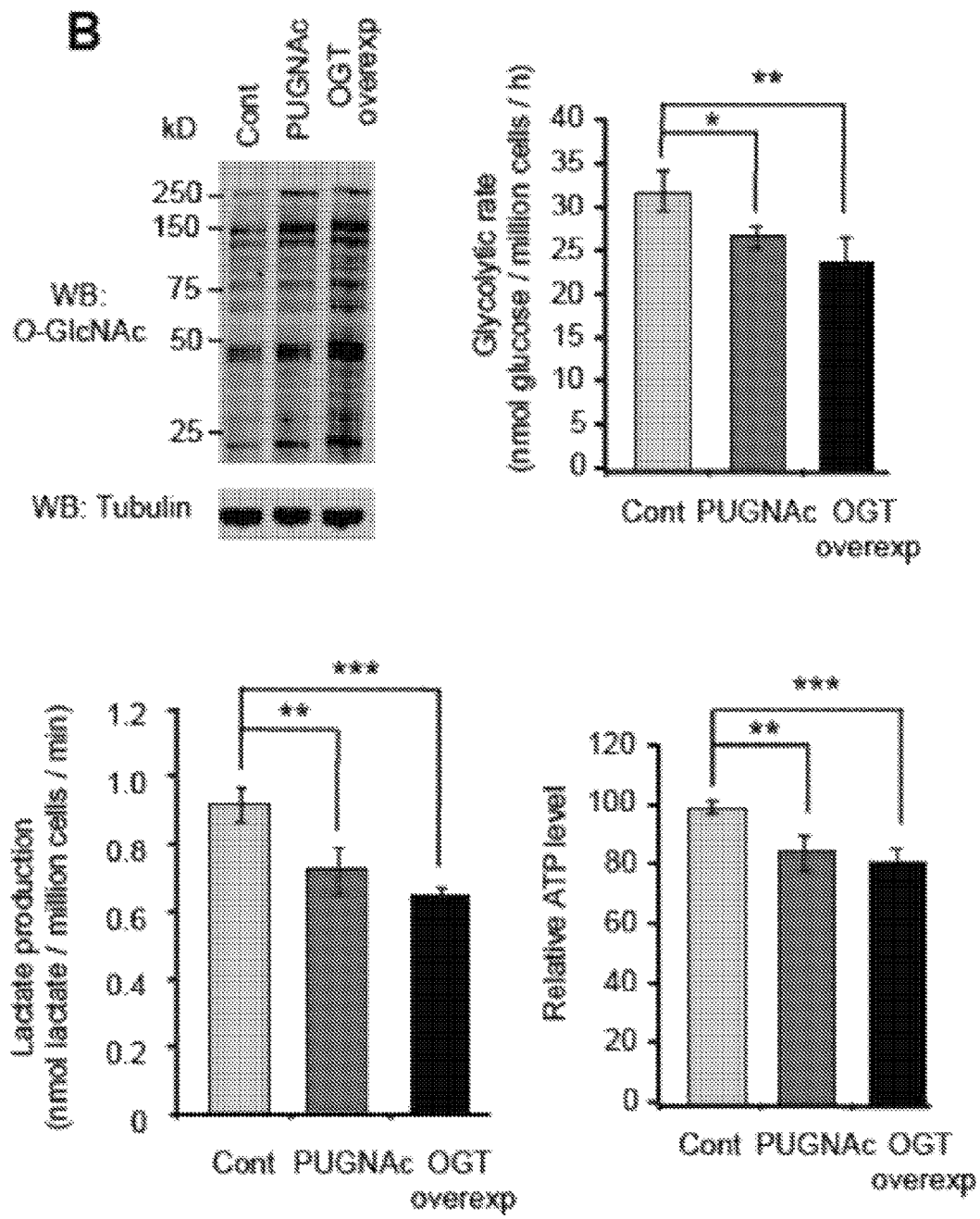

In order to determine whether O-GlcNAcylation directly couples nutrient sensing to cellular metabolism, O-GlcNAc concentrations were modulated, and then the effects on aerobic glycolysis were measured. Through overexpressing OGT or pharmacological inhibition of β-N-acetylglucosaminidase (O-GlcNAcase or OGA), global abundance of O-GlcNAc was increased by two- to fourfold in human lung cancer H1299 cells (FIG. 1A). Increasing the abundance of O-GlcNAc caused decreased rates of glucose metabolism relative to those of untreated cells under both normoxic and hypoxic conditions, as measured by the conversion of 5-$^3$H-glucose to $^3H_2O$, which is catalyzed by enolase in the penultimate step of glycolysis (FIG. 1B and FIG. 5). Enhancing O-GlcNAcylation also resulted in reduced lactate production and lowered cellular concentrations of ATP (FIG. 1B). Similar effects were observed in other cells, including invasive human lung cancer A549 cells (FIG. 6A) and human embryonic kidney 293T cells (FIG. 6B).

Figure 7:
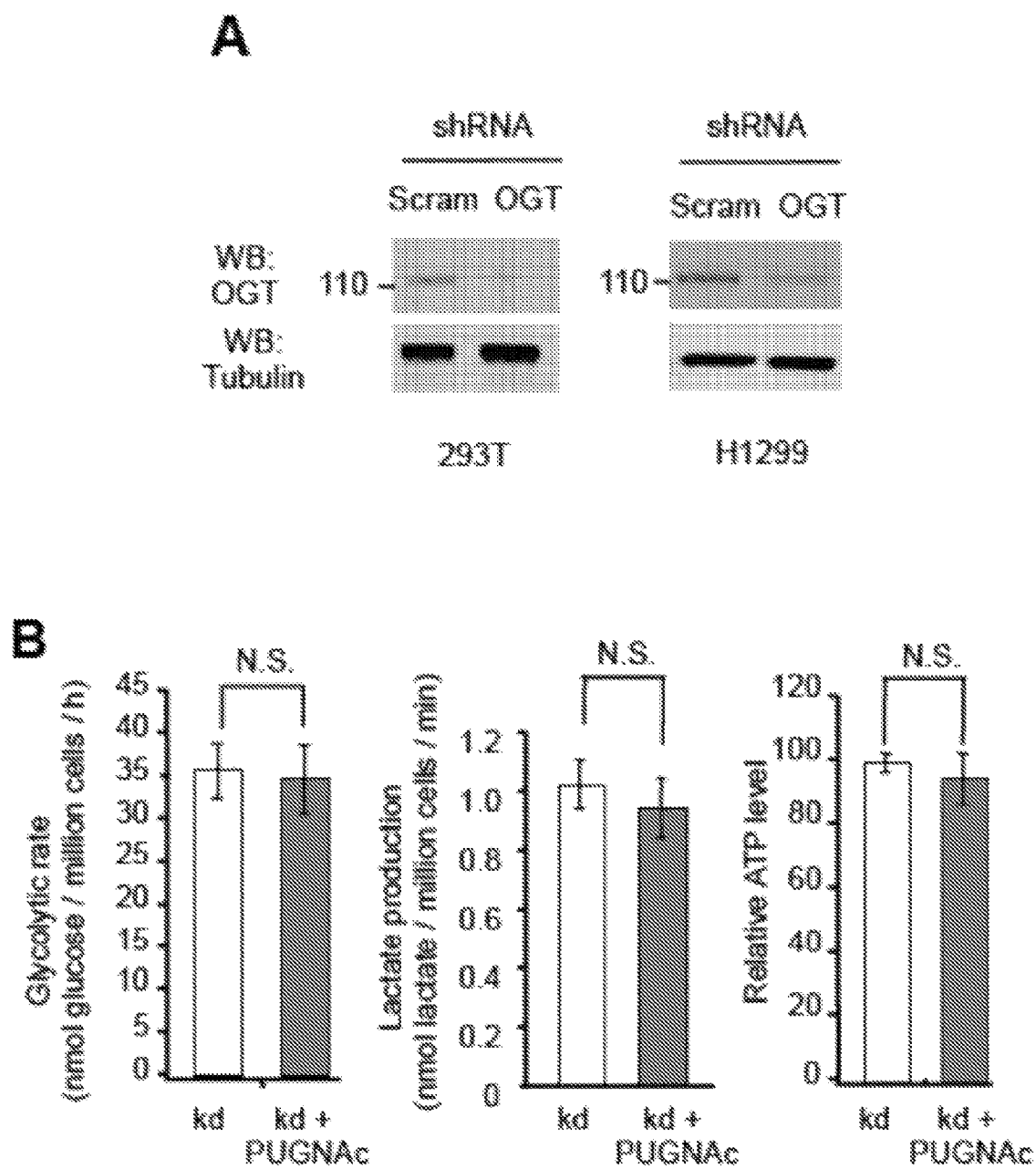
FIGS. 7A-D show immunoblots and bar graphs illustrating effects of O-GlcNAcylation on cellular metabolism.
Figure 7:
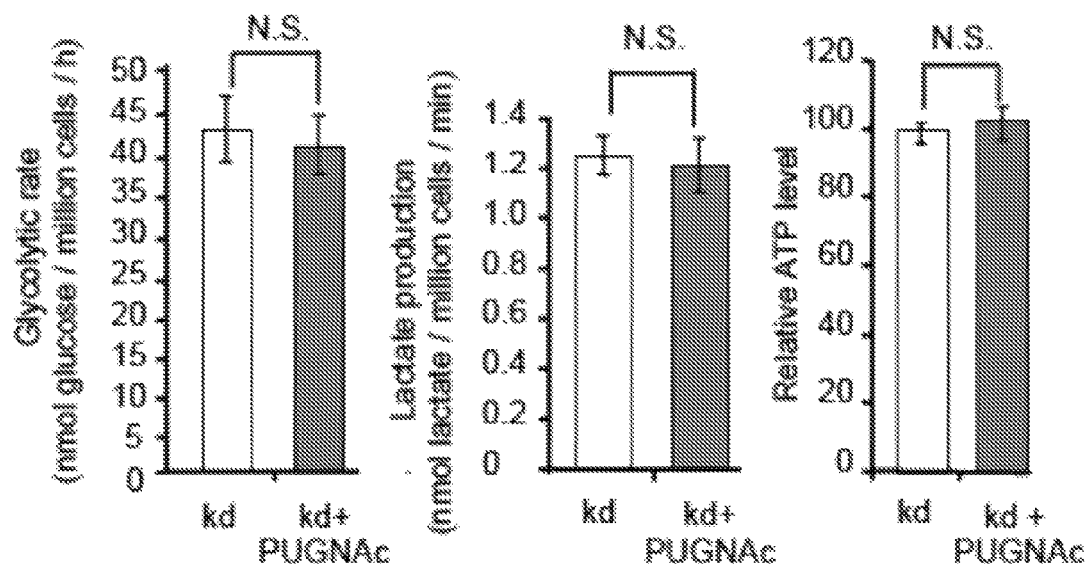
Figure 7:
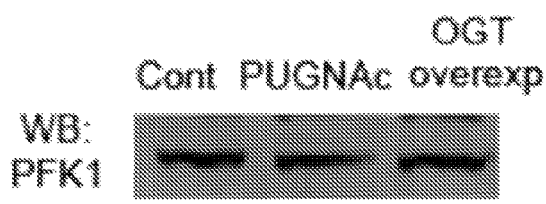

It has been reported that glycolytic flux is 5 to 15 times higher in cancer cells than flux through other central pathways in cancer cells. (Sidorenko et al., Biotechnol. Prog. 24, 311 (2008)). Small alterations in glycolysis can result in substantial changes in the relative flow of branching pathways. (Possemato et al., Nature 476, 346 (2011)). In order to assess whether OGT-dependent glycosylation of protein substrates contributes to these effects, OGT in H1299 and 293T cells was stably depleted through the expression of short hairpin RNA (shRNA) (FIG. 7). The inhibition of OGA in these OGT-deficient cells had no significant effect on glucose metabolism, lactate production, or ATP production (FIG. 7).

Example 24

Effects of O-GlcNAcylation on Glycosylation of PFK1

Figure 8:
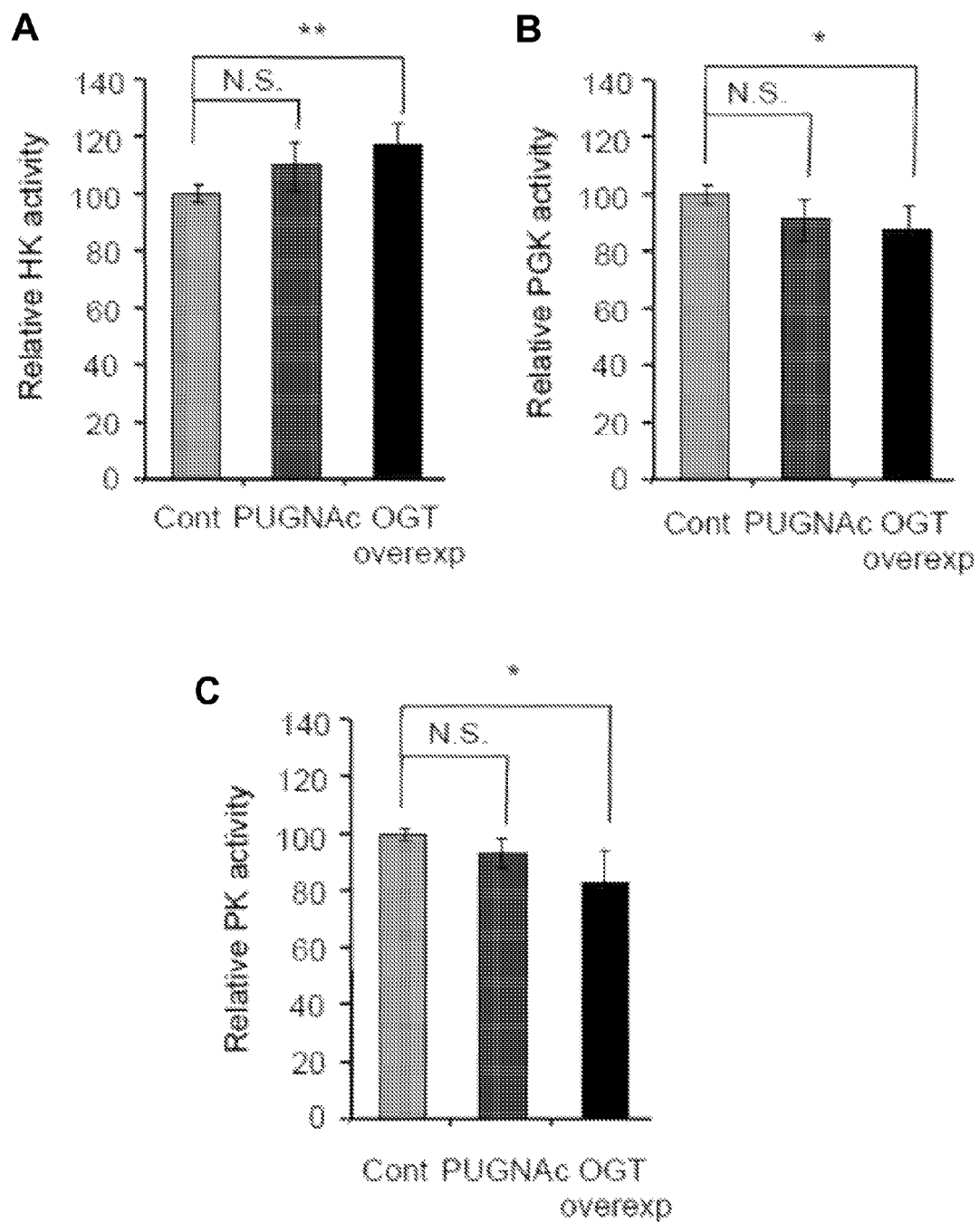
FIGS. 8A-C show bar graphs illustrating effects of enhancement of O-GlcNAcylation levels on activity of other glycolytic enzymes.

The amounts of O-GlcNAc in 293T were modulated, and the activity of the enzymes in the glycolytic pathway was assayed. Increased amounts of O-GlcNAc resulted decreased activity of phosphofructokinase 1 (PFK1), a major regulatory enzyme that controls flux through glycolysis (FIG. 1C). The expression level of PFK1 protein was not changed (FIG. 7D). Enhancing the abundance of O-GlcNAc had little effect on other key regulatory points in the pathway, including hexokinase, phosphoglycerate kinase, and pyruvate kinase (FIG. 8), nor did it affect other glycolytic enzymes.

Figure 9:
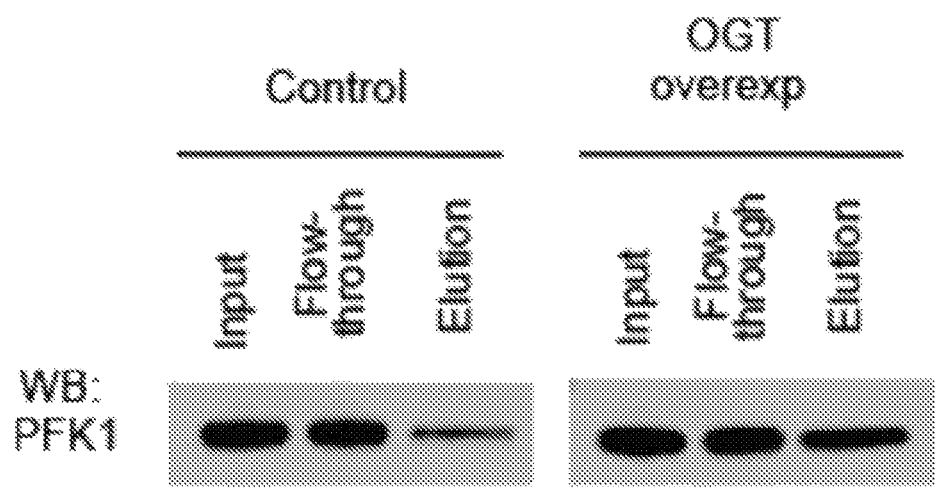
FIG. 9 shows immunoblot results for biotinylation, capture, and detection of glycosylated PFK1 from untreated or OGT-overexpressing 293T cells.

In order to test whether PFK1 is directly O-GlcNAcylated, O-GlcNAc-modified proteins from 293T cell lysates was labeled with a non-natural azido sugar through exposure to an exogenous galactosyltransferase enzyme that specifically glycosylates terminal GlcNAc sugars. Labeled proteins were then biotinylated through [3+2] azide-alkyne cycloaddition chemistry and isolated with streptavidin-agarose beads. Strong O-GlcNAcylation of PFK1 was showed by immunoblotting of the purified proteins with an antibody to PFK1 (FIG. 1D), which was further enhanced by overexpression of OGT (FIG. 9).

Figure 10:
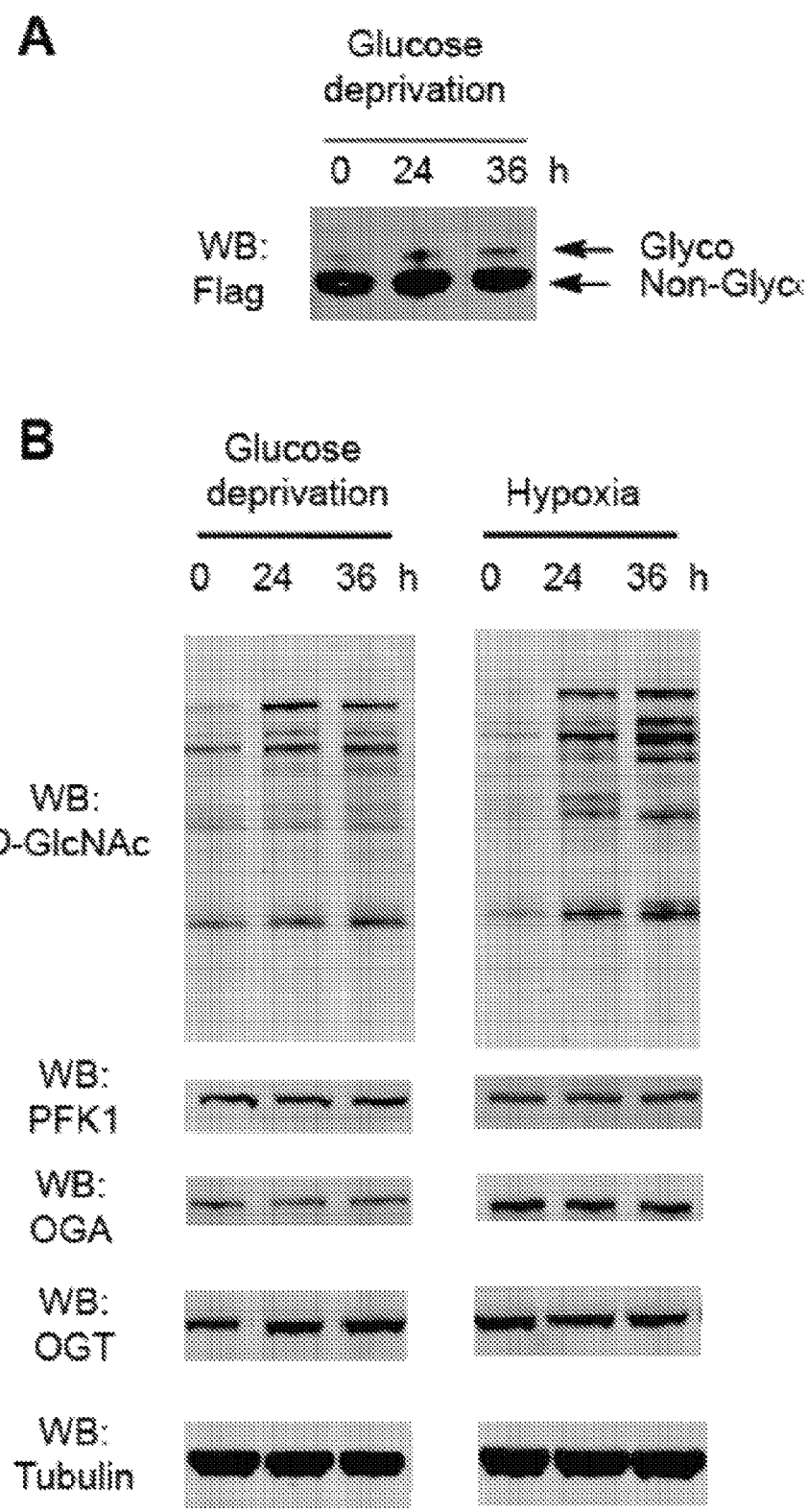
FIGS. 10A-B show immunoblots illustrating induction of PFK1 glycosylation in response to glucose deprivation and hypoxia.

To further test whether PFK1 is directly O-GlcNAcylated, a stable cell line expressing Flag-tagged PFK1 was generated and O-GlcNAc-modified proteins in the lysate was selectively labeled with a 5-kD polyethylene glycol (PEG) mass tag to shift their molecular mass. Both the nonglycosylated and glycosylated species of Flag-PFK1 was visualized by immunoblotting with an antibody to Flag (FIG. 1E). The population of glycosylated PFK1 significantly increased upon OGT overexpression or OGA inhibition. Moreover, PFK1 glycosylation was induced under hypoxic conditions within minutes and accumulated in a time-dependent manner on 32.3±3.8% of PFK1 (FIG. 1F and FIG. 10). It has been reported that O-GlcNAc levels and OGT expression are increased by nutrient deprivation and other forms of cell stress. (Taylor et al., *J. Biol. Chem.* 283, 6050 (2008)). Consistent with that, Glycosylation was also stimulated when cells were deprived of glucose (13.3±2.2%; FIG. 10).

Figure 11:
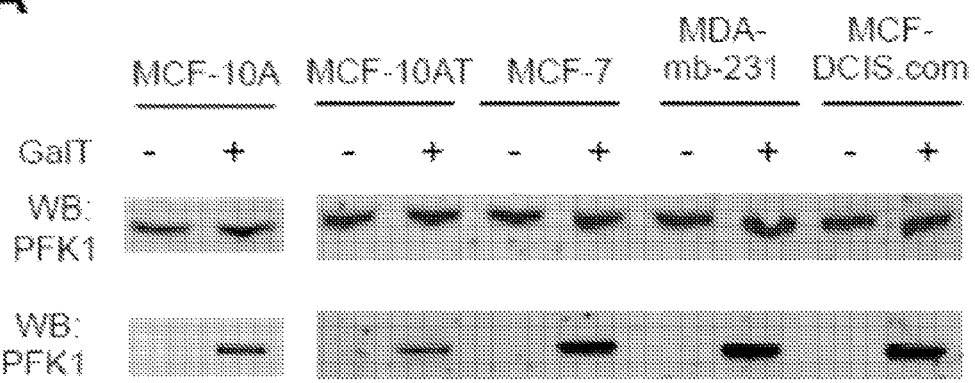
FIGS. 11A-C show immunoblots illustrating PFK1 glycosylation in various human solid tumor cell lines, including enhancement in malignant compared to non-tumorigenic cell lines.
Figure 11:
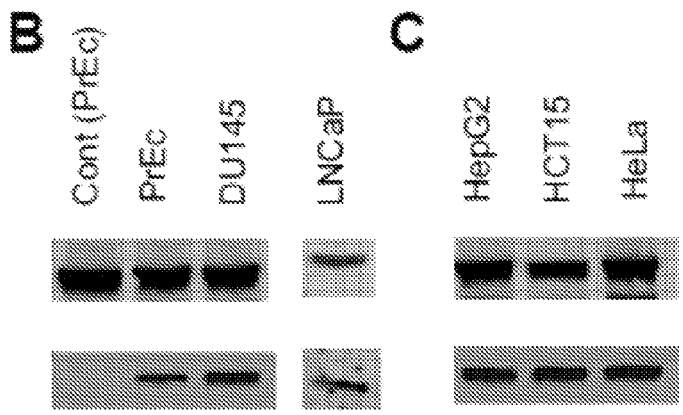
Figure 12:
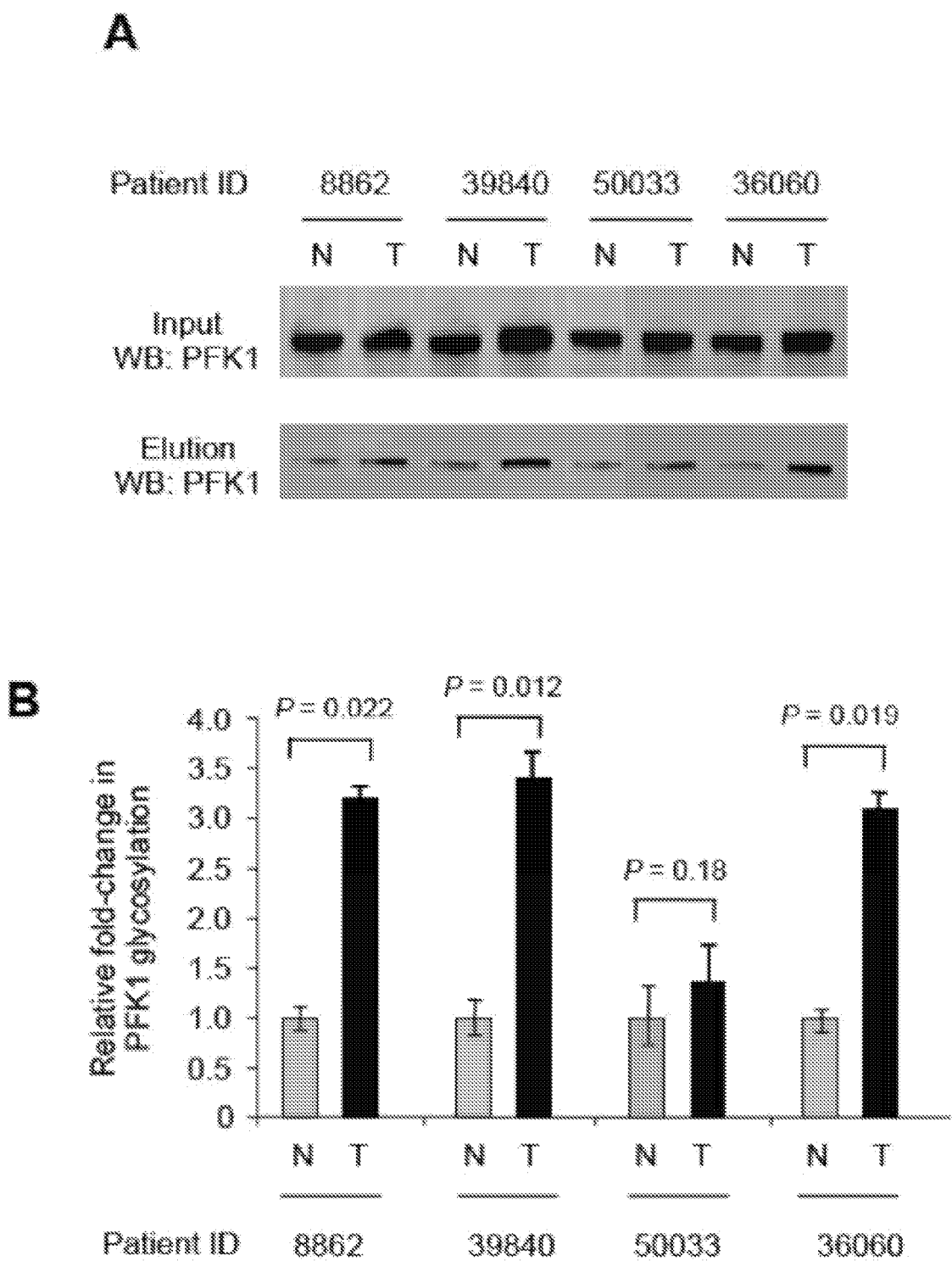
FIGS. 12A-B show an immunoblot and bar graph illustrating PFK1 glycosylation levels in human breast tumor (T) or normal (N) tissues.
Figure 13:
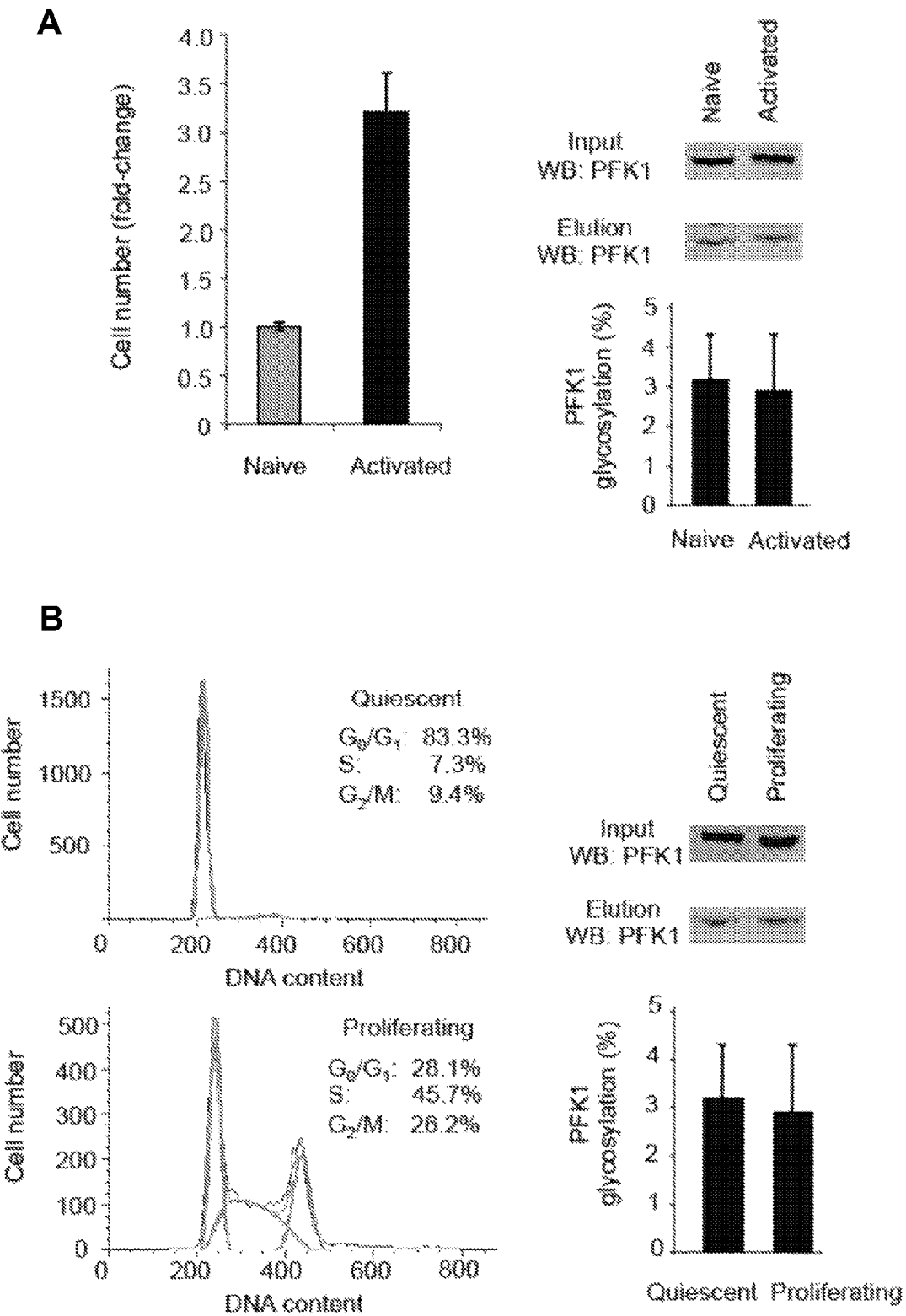
FIGS. 13A-B shows immunoblots and graphs illustrating PFK1 glycosylation levels in rapidly proliferating normal cells compared to quiescent normal cells.

Glycosylation of PFK1 was also examined in cancer cell lines and cancer tissues. PFK1 was glycosylated in multiple cell lines from human solid tumors, including breast, prostate, liver, colon, and cervical cells, and glycosylation was greater in malignant than in nontumorigenic breast and prostate cell lines (FIG. 11). Glycosylation of PFK1 also occurred in human breast and lung tumor tissues and was significantly elevated by two- to fourfold in the majority of tumors relative to tumor-adjacent normal tissues from the same patient (FIG. 1G and FIG. 12). Low-stage (stages I and II) lung adenocarcinoma tumors exhibited on average a 1.8-fold increase in PFK1 glycosylation as compared to that of the matched normal tissue, whereas high-stage (stages III and IV) lung adenocarcinomas showed an average 3.2-fold increase in glycosylation. PFK1 glycosylation was not induced in rapidly proliferating normal mouse T lymphocytes and human dermal fibroblast cells, as compared to their quiescent counterparts (FIG. 13). Thus, PFK1 is modified with O-GlcNAc in cancer cells both in vitro and in vivo, and glycosylation is increased specifically under conditions associated with tumorigenesis and tumor growth.

Example 25

Identification of Glycosylation Site(s) on PFK1

Figure 14:
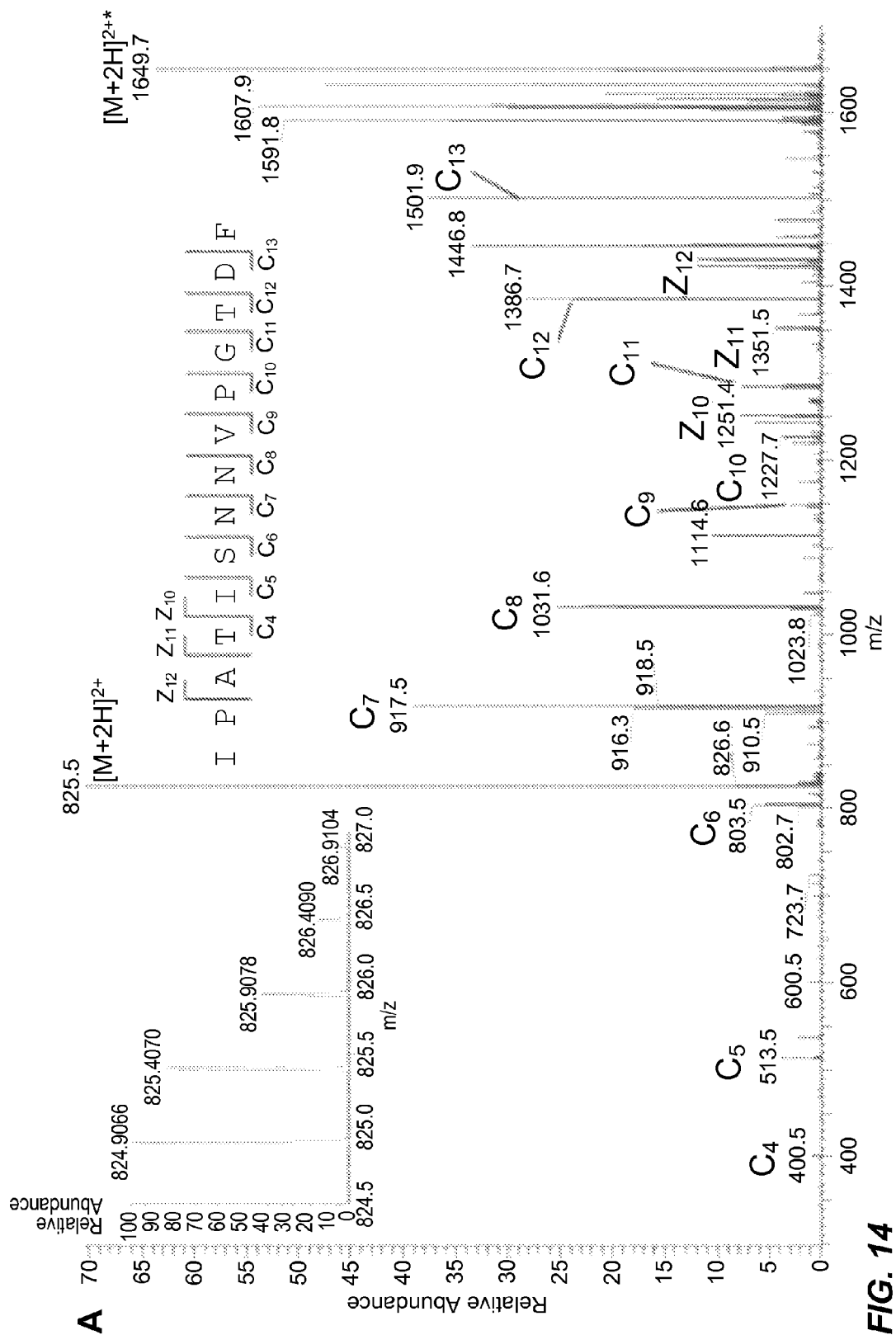
FIGS. 14A-C show mass spectrometry results identifying a glycosylation site of PFK1 (Residues 524-537 of SEQ ID NO: 1), a sequence alignment of residuces surrounding Ser529 across different species (Residues 519-537 of SEQ ID NO: 1 and SEQ ID NOS 10-19, respectively, in order of appearance), and an immunoblot of PFK1 compared to a PFK1 mutant.

In order to identify the glycosylation site(s) on PFK1, Flag-tagged PFK1 and OGT were transiently overexpressed in 293T cells. After immunoprecipitation and proteolytic digestion of PFK1, O-GlcNAcylated peptides were enriched by wheat germ agglutinin lectin affinity chromatography and subjected to electron transfer dissociation mass spectrometry analysis. A single site of glycosylation at $Ser^{529}$, a highly conserved residue important for allosteric regulation of PFK1 by fructose-2,6-bisphosphate (F-2,6-BP) was identified (FIG. 14). F-2,6-BP is the dominant activator of PFK1 at the high ATP concentrations (2 to 5 mM) found in cancer cells. The glycosylation of PFK1 in 293T cells was abolished by mutating $Ser^{529}$ to alanine (S529A), whereas alanine mutation of $Thr^{527}$ had no effect (FIG. 14).

Figure 15:
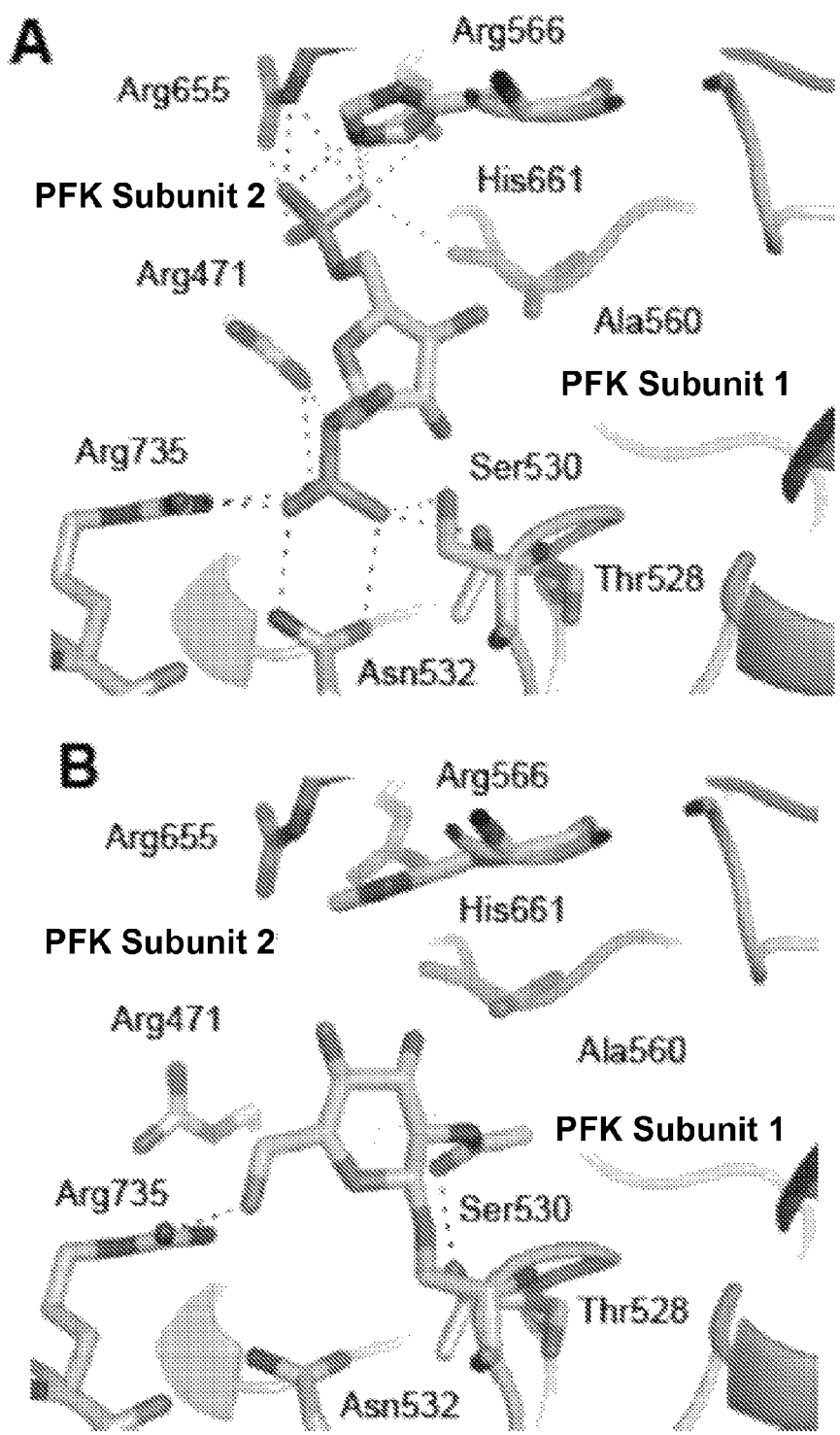
FIGS. 15A-B show computational models of rabbit PFK1 bound to F-2,6-BP and O-GlcNAc-modified PFK1.

In order to generate structural models of rabbit PFK1 complexed to F-2,6-BP and O-GlcNAcylated rabbit PFK1, the *Saccharomyces cerevisiae* structure, which shares 82% sequence identity within the F-2,6-BP binding site, and the rabbit structure, which shares 97% sequence identity was used. (FIG. 15; the root mean square deviation between the rabbit and yeast structures was only 1.70 Å). $Ser^{529}$ formed a hydrogen bond with the 2-phosphate group of F-2,6-BP, and the O-GlcNAc moiety occupied the F-2,6-BP-binding pocket, indicating that O-GlcNAcylation might inhibit PFK1 activity by blocking binding of F-2,6-BP and disrupting PFK1 oligomerization.

Example 26

Inhibition of PFK1 Activity and Oligomerization by Glycosylation

Figure 2:
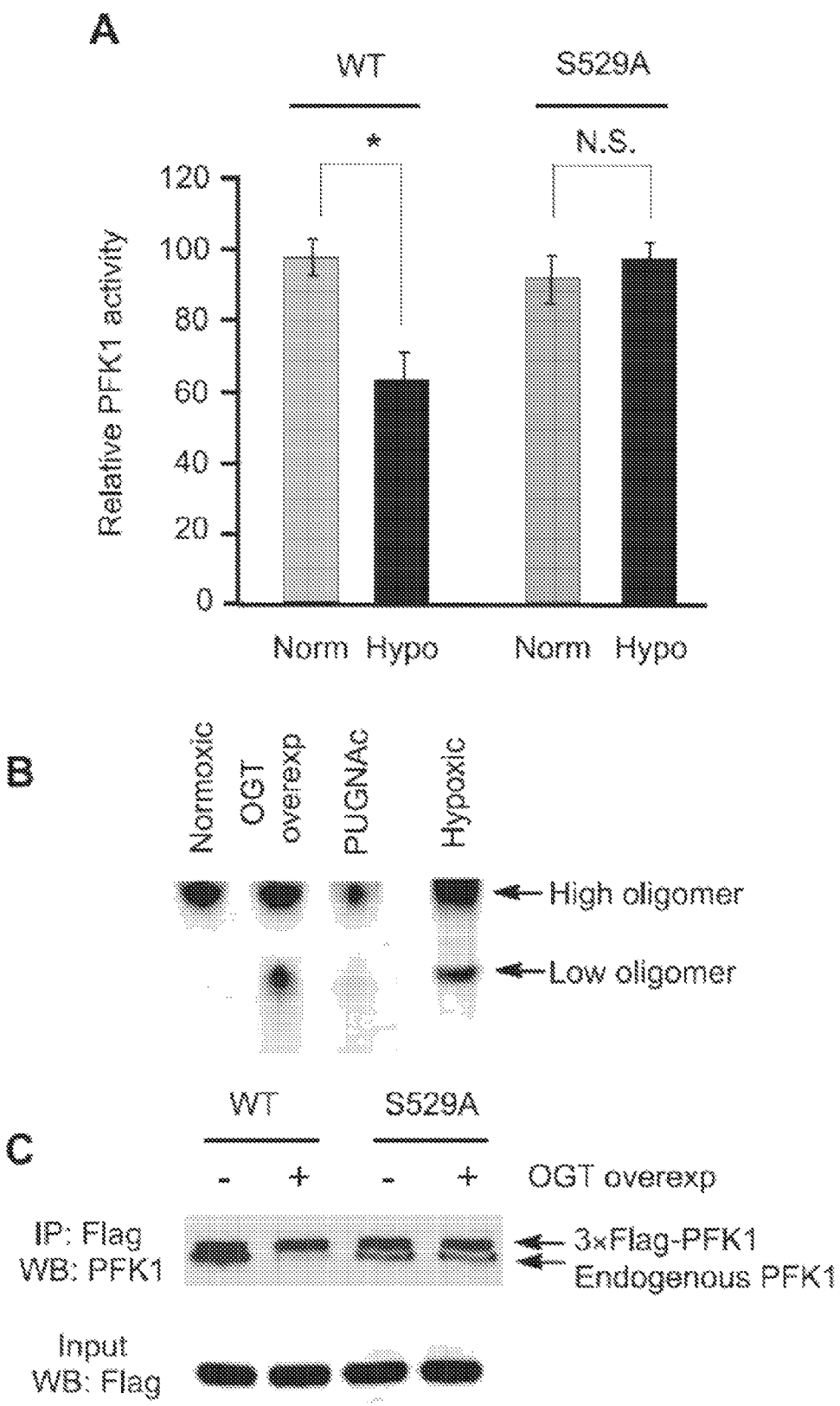
FIGS. 2A-C illustrate inhibtion of PFK1 activity and oligomerization by glycosylation.
Figure 16A:
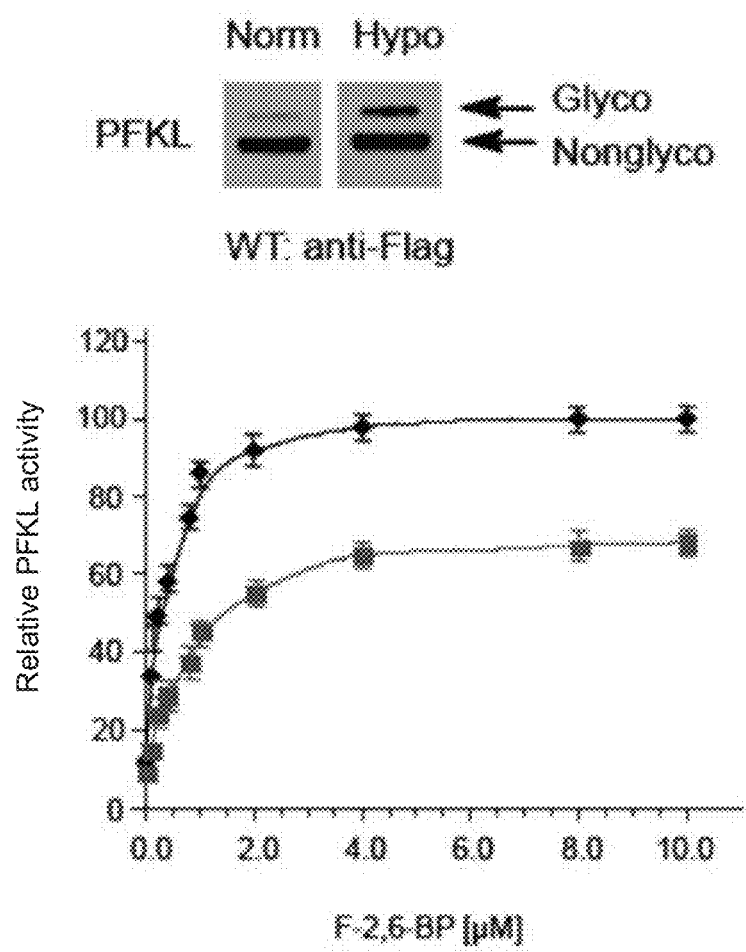
FIGS. 16A-C show immunoblots and graphs illustrating effects of glycosylation on different PFK1 isoforms across a rang of F-2,6-BP concentrations.
Figure 16B:
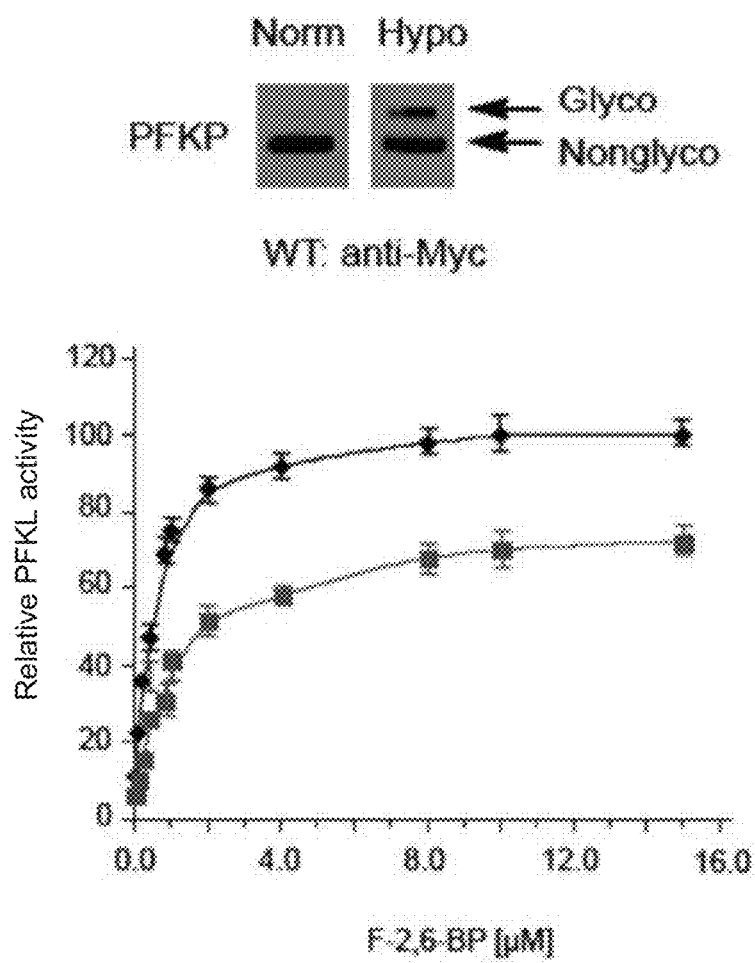
Figure 16C:
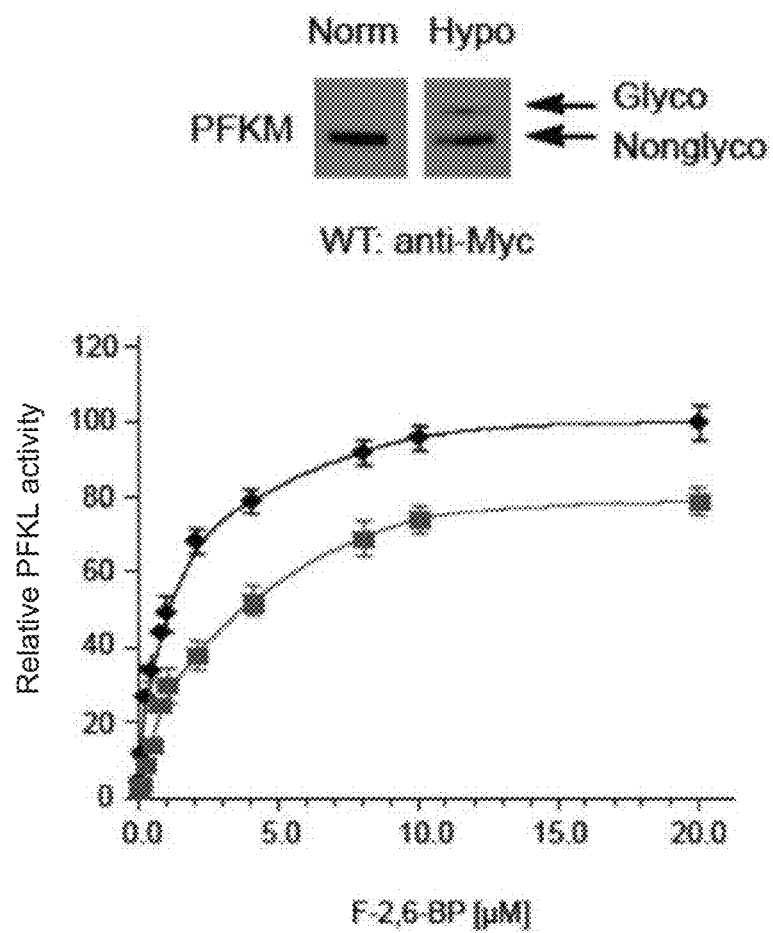
Figure 17:
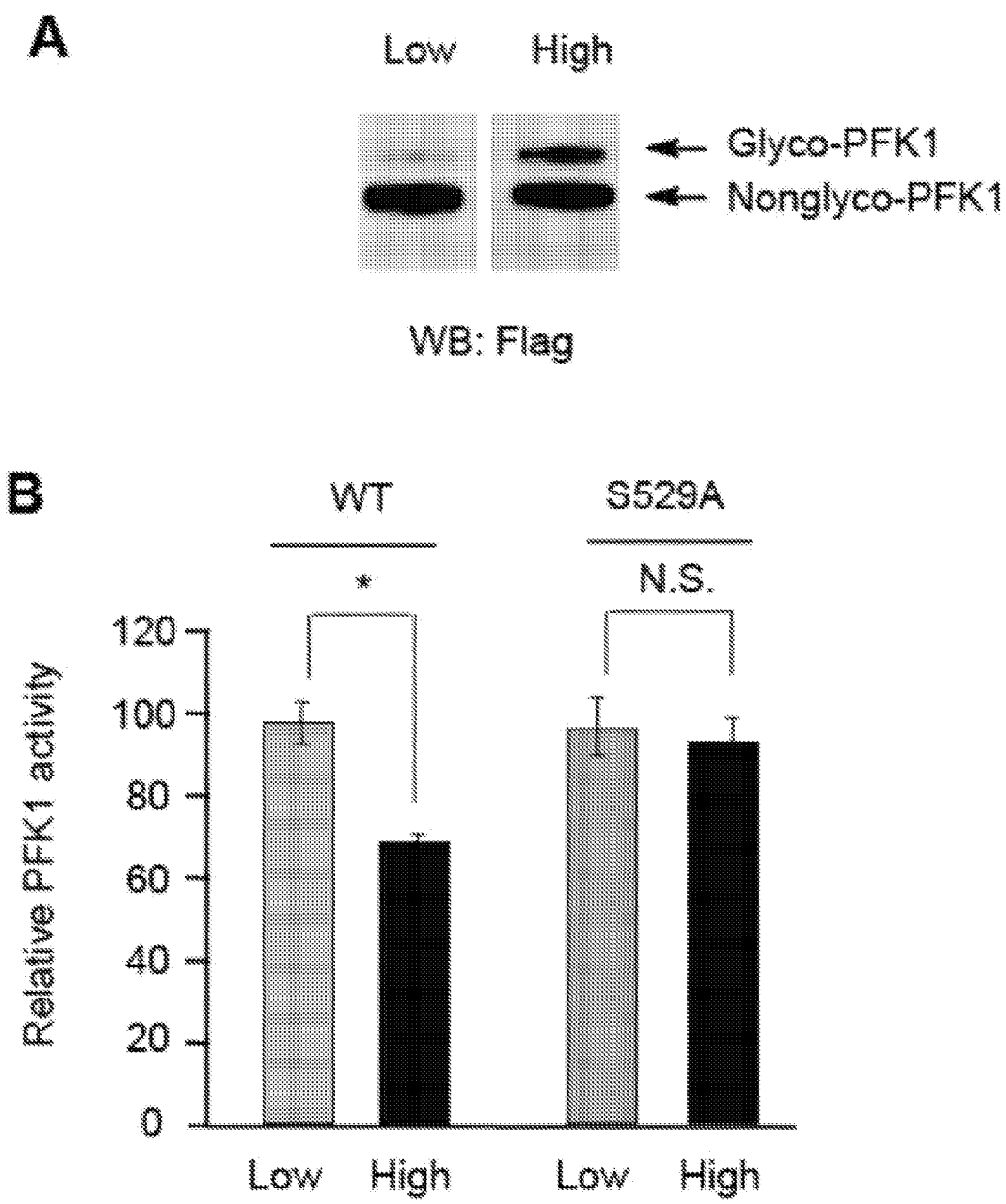
FIGS. 17A-B show immunoblots and bar graphs illustrating effects of O-GlcNAc levels on WT and S529A PFK1.
Figure 18:
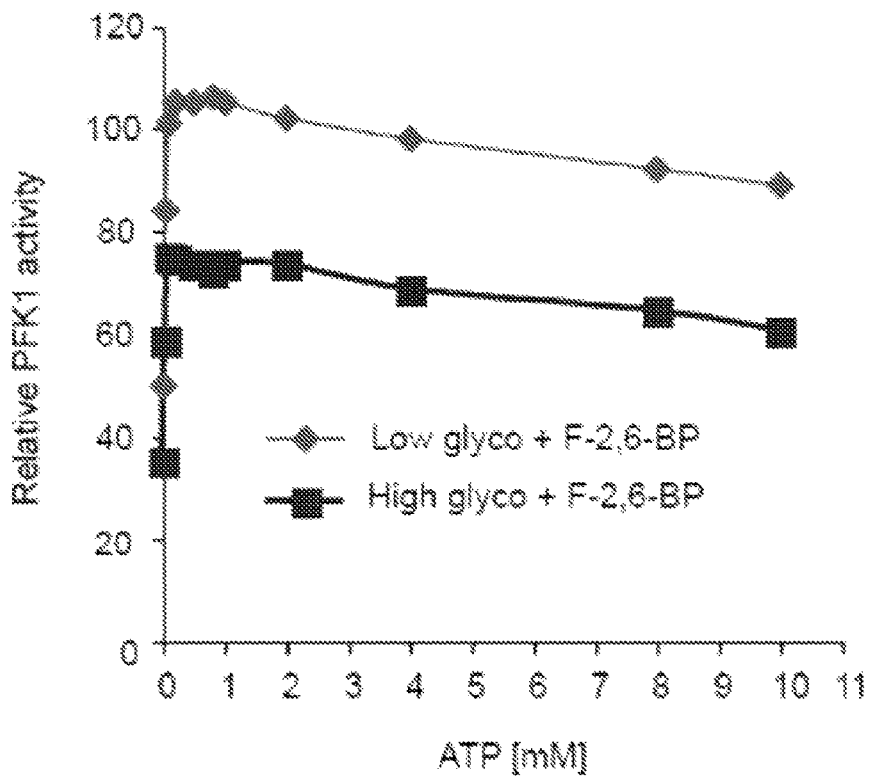
FIGS. 18A-B show graphs illustrating inhibition of PFK1 activity by glycosylation across a range of ATP concentrations in the presence and absence of F-2,6-BP.
Figure 18:
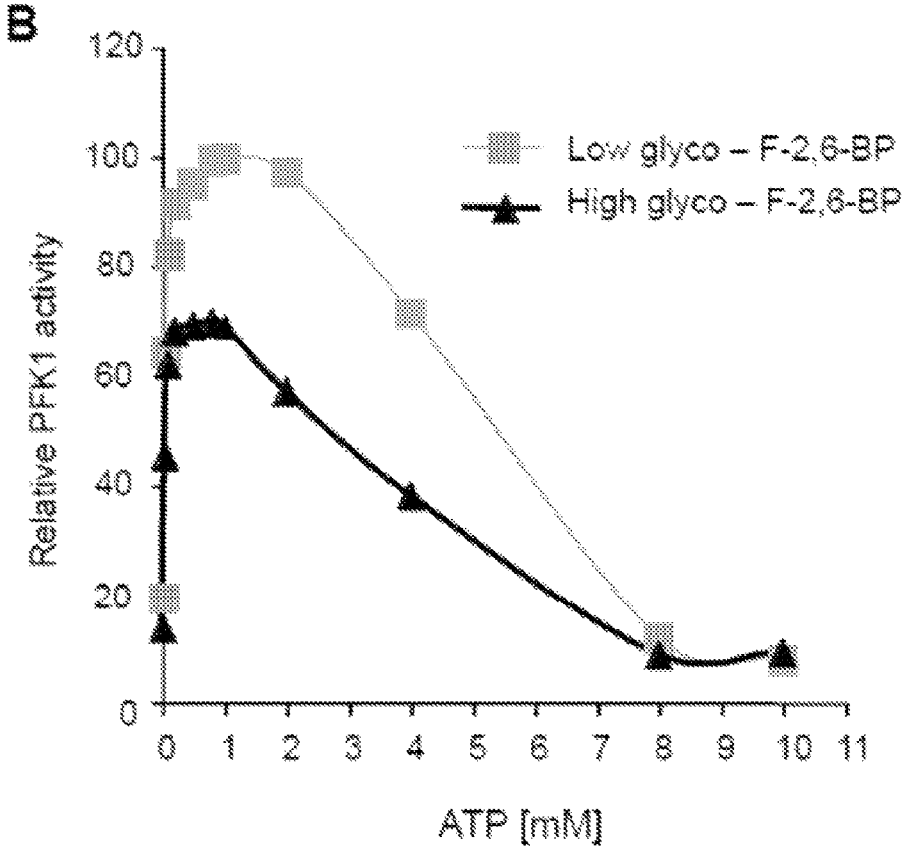
Figure 19:
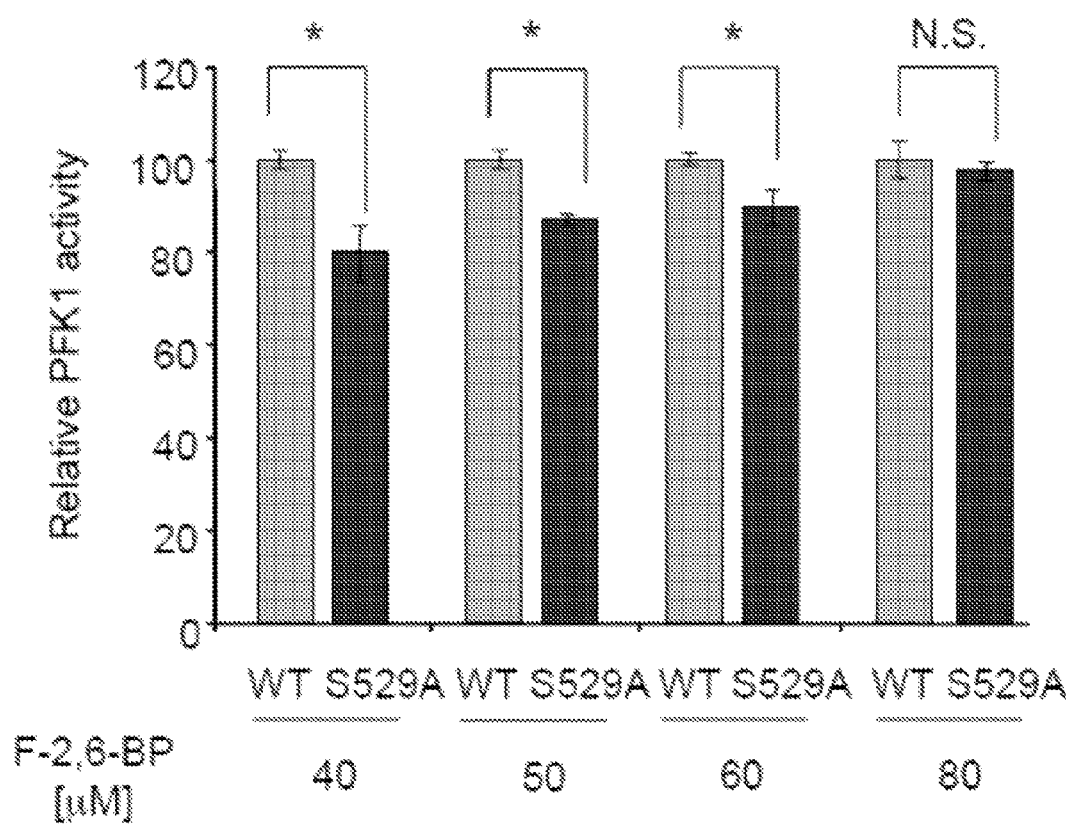
FIG. 19 shows a bar graph illustrating relative activities of Flag-tagged WT and S529A PFK1 at the indicated concentrations of F-2,6-BP.

In order to examine the effects of O-GlcNAcylation on PFK1 activity, human Flag-tagged PFK1 (L, M, and P isoforms) was expressed in 293T cells in the presence or absence of hypoxic conditions, which enhance PFK1 glycosylation. Increasing O-GlcNAcylation of PFK1 by 25 to 33% because of hypoxia decreased the activity of all three isoforms by 21 to 36%, with the L and P isoforms being most sensitive to glycosylation (FIG. 2A and FIG. 16). PFK1 activity was not significantly changed under hypoxia when $Ser^{529}$ was mutated to alanine (FIG. 2A). Similar effects on PFK1 activity were observed when O-GlcNAcylation was increased by means of other cellular treatments (FIG. 17). Furthermore, glycosylation inhibited PFK1 activity across a wide ATP concentration range in the presence and absence of F-2,6-BP (FIG. 18). Consistent with the importance of $Ser^{529}$ in recognition of the allosteric activator, the activity of S529A PFK1 was impaired at lower F-2,6-BP concentrations (FIG. 19).

Figure 20:
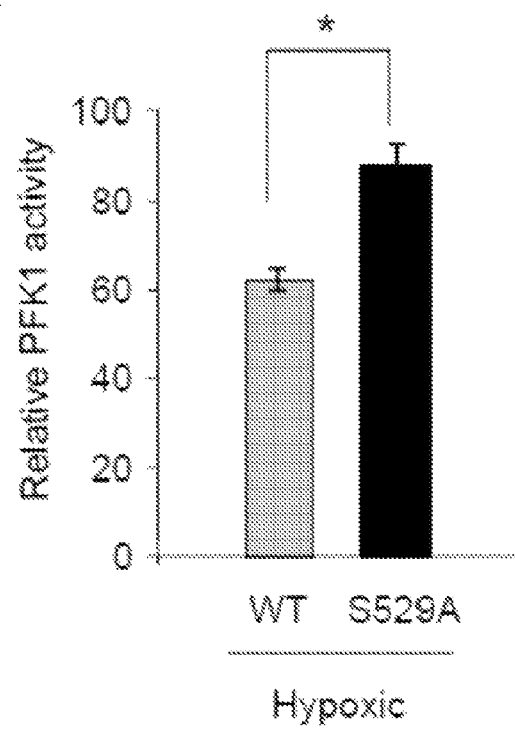
FIGS. 20A-B show bar graphs illustrating S529A mutation rescue of inhibition of PFK1 activity by glycosylation.
Figure 20:
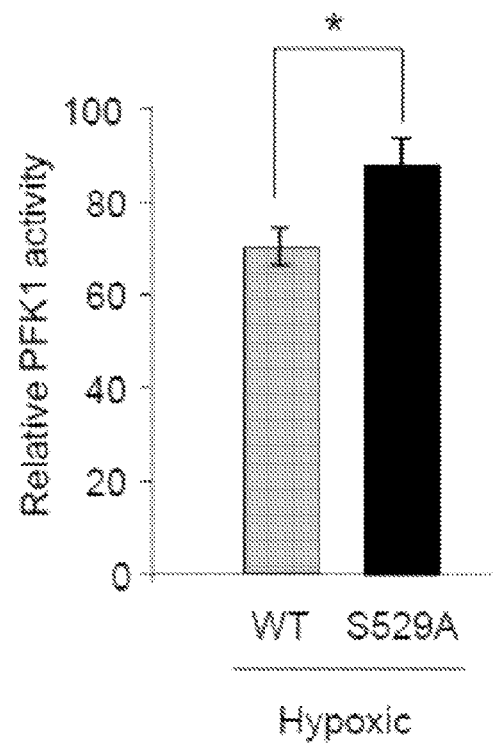

The effects of glycosylation in the presence of endogenous F-2,6-BP concentrations in 293T cells or 8.5 µM F-2,6-BP, which is within the physiological range for cancer cells, were also examined. In both cases, the activity of wild-type (WT) PFK1 was significantly lower than that of S529A PFK1 when glycosylation was induced by hypoxia (FIG. 20). Therefore, glycosylation has a strong inhibitory effect on PFK1 activity, and the mutation of $Ser^{529}$ to Ala rescues the inhibitory effect, indicating that O-GlcNAcylation of PFK1 at $Ser^{529}$ provides a mechanism to overcome the allosteric regulation of PFK1 by ATP and F-2,6-BP.

Figure 21:
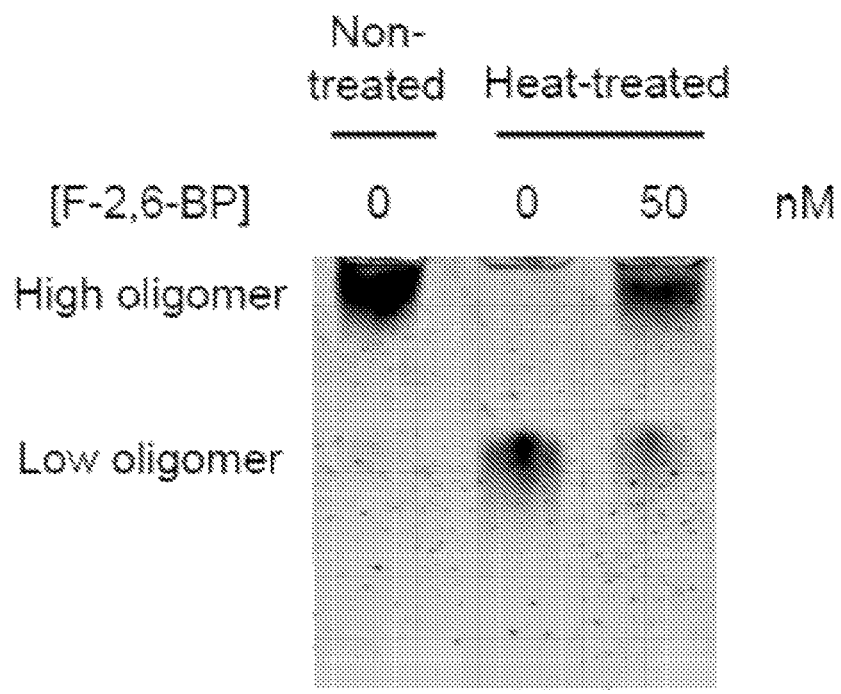
FIG. 21 shows an immunoblot illustrating reduction of oligomerization state of PFK1 by heat denaturation, and partial rescue by F-2,6-BP.

It has been reported that F-2,6-BP slows the dissociation of complexes of PFK1 and promotes the association of PFK1 into tetramers and higher oligomers with enhanced catalytic activity. (Sola-Penna et al., *IUBMB Life* 62, 791 (2010)). Flag-tagged PFK1 was expressed in 293T cells under normoxic or hypoxic conditions. After hypoxia treatment, a fraction of PFK1 exhibited faster mobility during native gel electrophoresis (FIG. 2B). A similar shift in mobility was observed when PFK1 glycosylation levels were increased by OGT overexpression or OGA inhibition and when PFK1 was heat-denatured (FIG. 21), suggesting that this complex represents a lower oligomeric state of PFK1.

The association of Flag-tagged PFK1 with endogenous PFK1 was also examined by coimmunoprecipitation. Overexpression of OGT impaired the coimmunoprecipitation of PFK1 subunits, and this effect was blocked by alanine mutation of $Ser^{529}$ (FIG. 2C), suggesting that O-GlcNAcylation not only inhibits the activity of PFK1 but also appears to perturb the equilibrium between different oligomeric forms.

Example 27

PFK1 Glycosylation at $Ser^{529}$ Regulates Glycolysis, Increases PPP Flux, and Protects Cells from ROS-Mediated Cell Death In order to test the effects of PFK1 glycosylation on cellular metabolism, endogenous PFK1 was depleted and Flag-tagged WT or S529A PFK1 was stably expressed in H1299 cells (henceforth referred to as WT PFK1 or S529A PFK1 rescue cells; FIG. 3A). Upon OGT overexpression, cells expressing WT PFK1 exhibited reduced glycolysis and lactate production relative to control cells (FIG. 3B). No change in glycolytic rate or lactate production was observed in cells expressing S529A PFK1 upon OGT overexpression.

Figure 3:
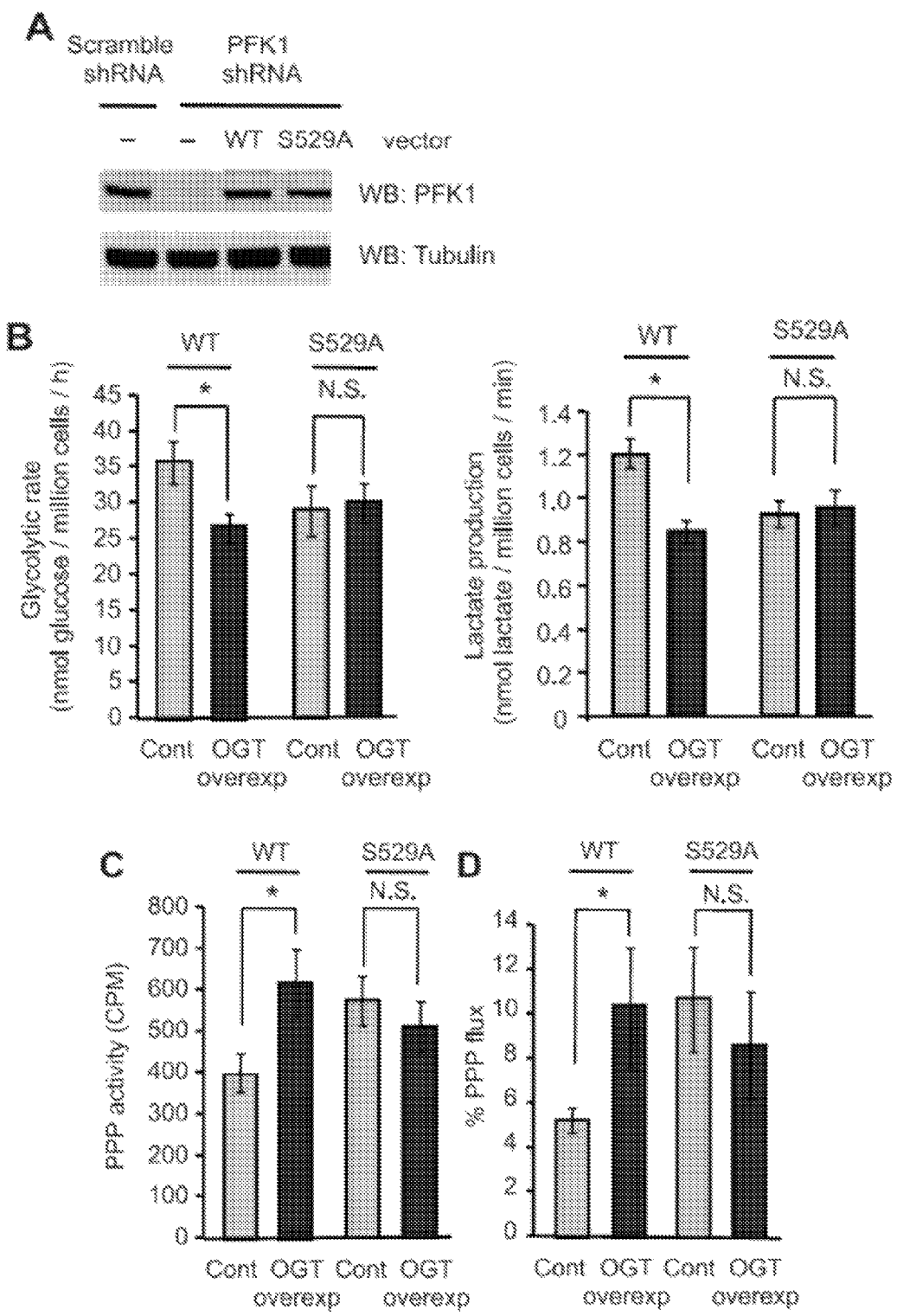
FIG. 3A shows results of a PFK-1 immunoblot of cells stably expressing shRNA and rescue constructs.
FIGS. 3B-F show bar graphs illustrating effects of PFK-1 mutation.
FIG. 3G shows a bar graph of cellular ROS levels induced by varying concentrations of diamide in untreated cells (Cont) and cells overexpressing OGT.
FIG. 3H shows a bar graph of percentage of cell death induced by varying concentration of hydrogen peroxide in untreated cells (Cont) and cells overexpressing OGT.
Figure 3:
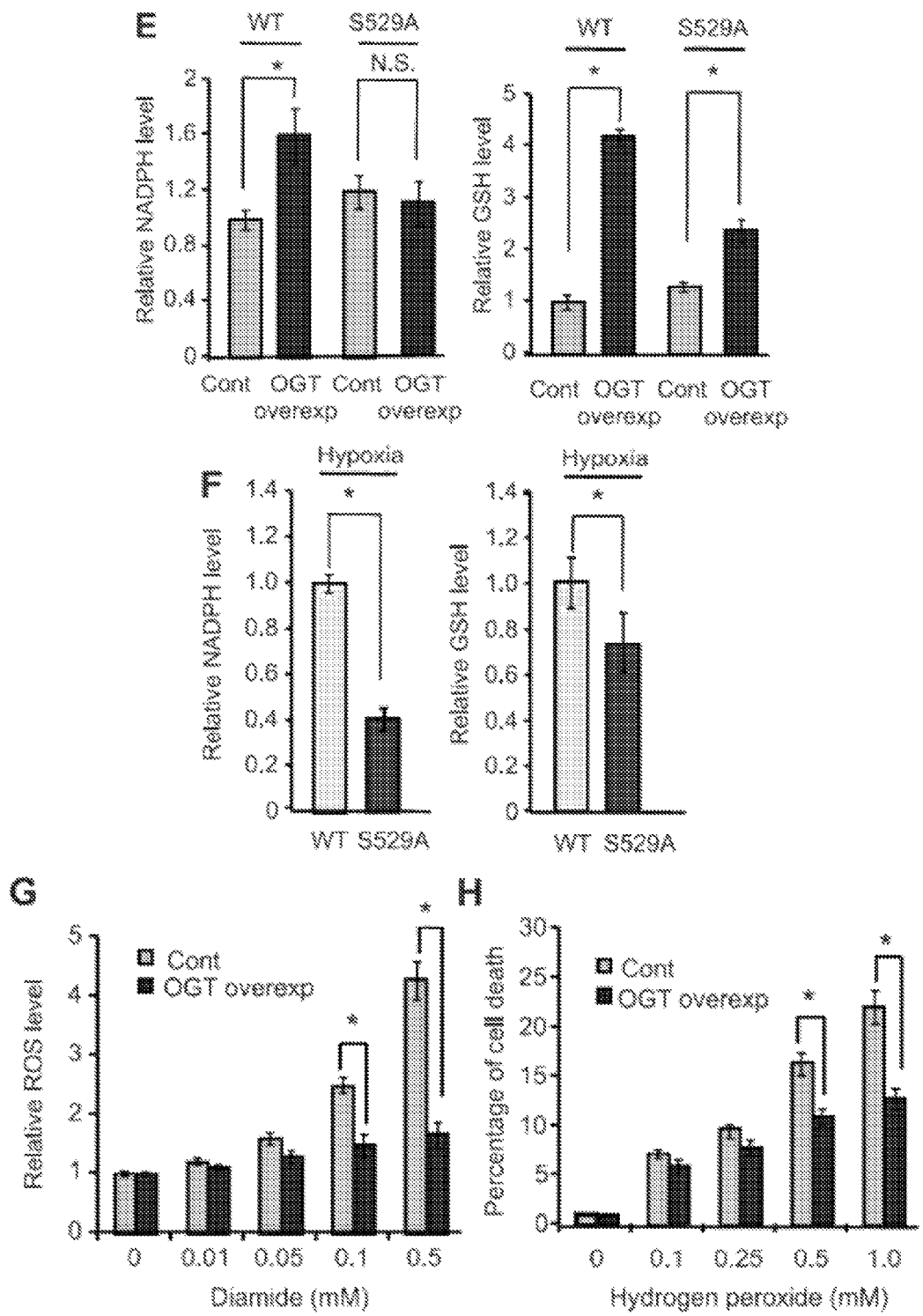

Enhanced O-GlcNAcylation in WT PFK1 rescue cells also increased total and proportional flux through the oxidative PPP pathway, as measured by the amount of released $^{14}CO_2$ from [1-$^{14}C$]-glucose, and by relative accumulation of singly versus doubly [$^{13}C$]-labeled lactate from a [1,2-$^{13}C$]-glucose feed (FIGS. 3, C and D). In contrast, PPP flux remained unaffected in S529A PFK1 rescue cells; however, it was increased as compared to that of untreated WT PFK1 rescue cells, possibly because of inhibitory effects of the S529A mutation on PFK1 activity (FIG. 19).

Consistent with increased PPP flux, Enhanced O-GlcNAcylation by OGT overexpression in WT PFK1 rescue cells led to 1.6-fold and 4-fold increases in amounts of NADPH and GSH, respectively (FIG. 3E). Blocking glycosylation of PFK1 at $Ser^{529}$ prevented the increase in NADPH and partially prevented the increase in GSH. Under hypoxic conditions, amounts of NADPH and GSH were also increased in WT PFK1 rescue cells as compared to those in S529A PFK1 rescue cells (FIG. 3F). Furthermore, steady-state concentrations of GSH, amino acids, and nucleotide precursors was also enhanced in WT PFK1 rescue cells relative to those in S529A PFK1 rescue cells.

The sensitivity of H1299 cells to ROS-mediated cell death upon overexpression of OGT was measured. Enhancing O-GlcNAcylation prevented the increase in ROS levels induced by diamide (FIG. 3G) and protected the cells from hydrogen peroxide-mediated cell death (FIG. 3H), indicating that increases in PPP flux induced by PFK1 glycosylation help promote cancer cell survival.

Example 28

PFK1 Glycosylation Contributes to Cell Proliferation and Tumor Growth

Figure 4:
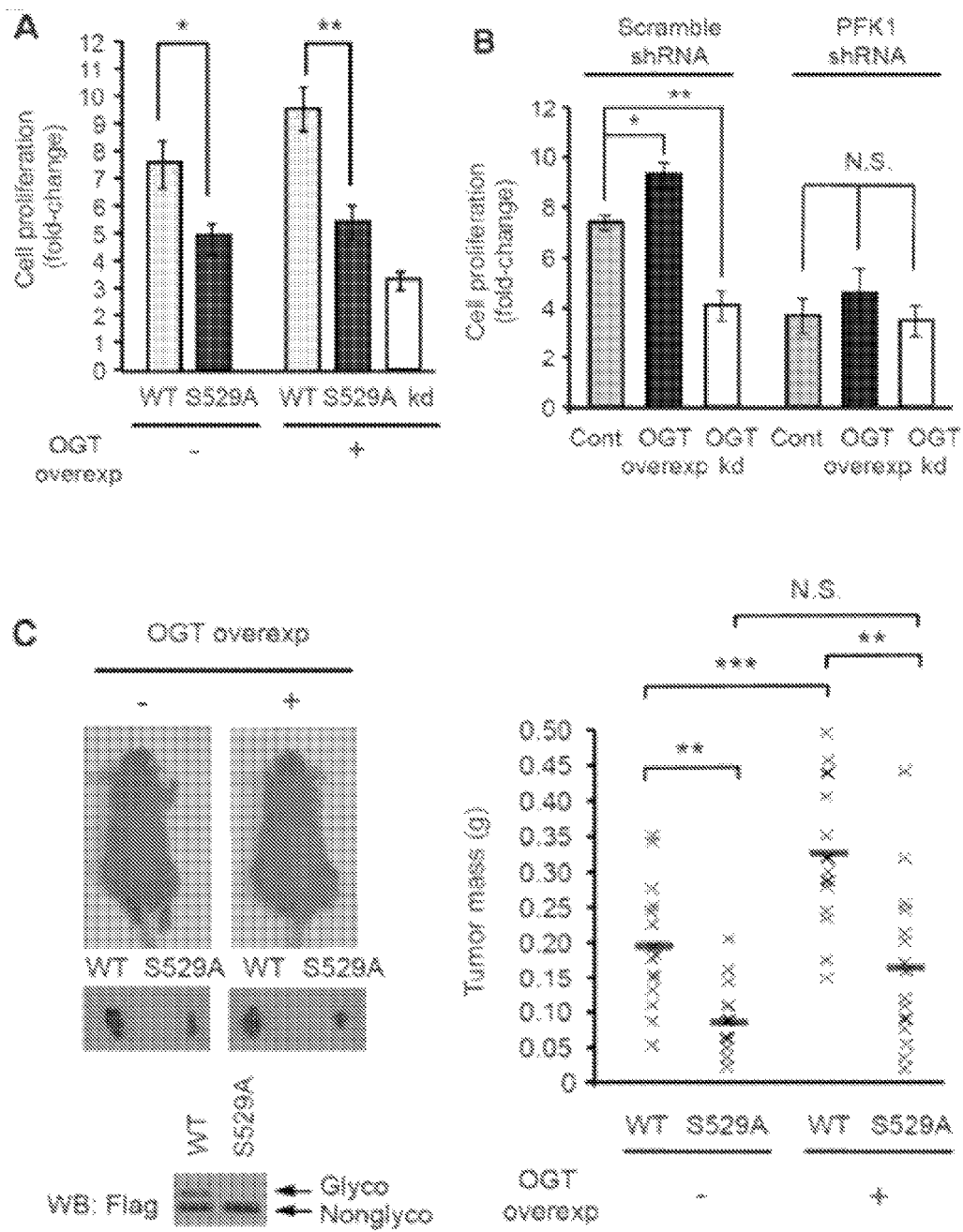
FIGS. 4A-C show experimental results illustrating effects of PFK-1 glycosylation on cell proliferation and tumor growth.

Consistent with reduced flux through the PPP, cells expressing the S529A mutant proliferated more slowly than cells expressing WT PFK1 under hypoxic conditions (FIG. 4A). Upon OGT overexpression, the proliferation rate of WT PFK1-expressing cells was further enhanced, whereas that of S529A PFK1-expressing cells was unchanged. Cell proliferation under hypoxic conditions was enhanced by OGT overexpression, while decreased by OGT depletion (FIG. 4B). Depletion of PFK1 abolished these effects, indicating that O-GlcNAcylation stimulates cell proliferation through a PFK1-dependent mechanism.

Figure 22:
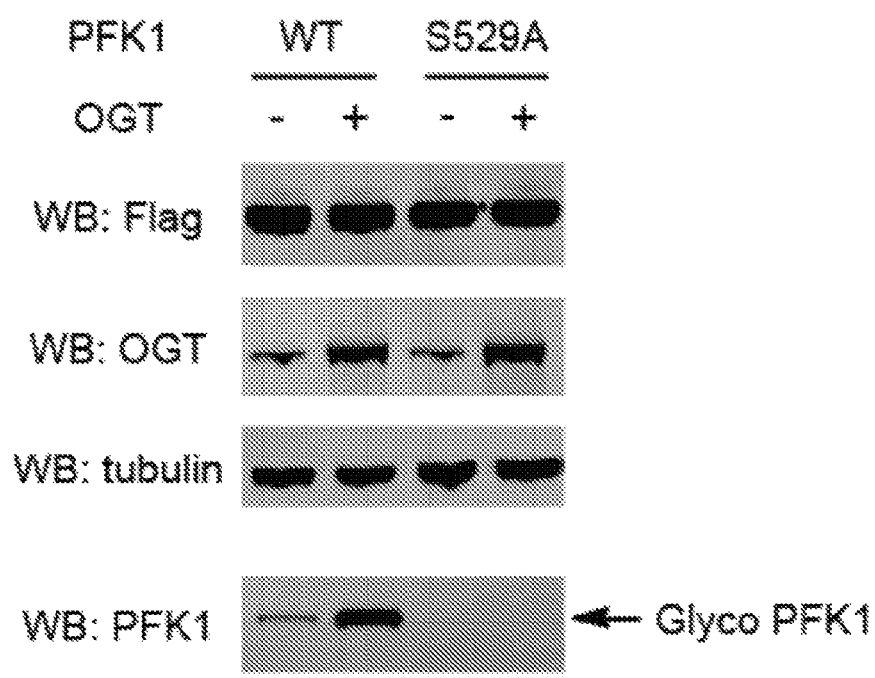
FIG. 22 shows immunoblots of proteins from H1299 cells transgenic for shRNA-resistant Flag-WT or S529A PFK1, and expressing scrambled shRNA or shRNA to endogenous PFK1. The bottom panel shows signal from glycosylated PFK1.

In order to assay for tumor formation, WT PFK1 or S529A PFK1 rescue cells were injected into immunocompromised mice (nu/nu) in the presence or absence of OGT overexpression (FIG. 22). Mice injected with S529A PFK1 rescue cells showed decreased tumor mass as compared to mice injected with WT PFK1 rescue cells (FIG. 4C). Moreover, overexpression of OGT in WT PFK1 rescue cells enhanced tumor growth but had no significant effect on S529A PFK1 rescue cells. Protein immunoblot analysis confirmed that the Flag-tagged WT or S529A PFK1 proteins were retained in the tumors and that WT PFK1 was O-GlcNAcylated (FIG. 4C). These results indicate that glycosylation of PFK1 at $Ser^{529}$ provides a critical growth advantage to tumor cells in vivo.

Example 29

Screening of Anti-Cancer Agents that Reduce PFK-1 Glycosylation

A cancer cell line can be used to screen for anti-cancer agents that reduce PFK-1 glycosylation. The cancer cell line is treated with a candidate anti-cancer agent. Glycosylation of PFK-1 is assayed by methods described in Example 7. If the candidate anti-cancer agent reduced PFK-1 glycosylation in treated cells as compared to control cells not administered the candidate anti-cancer agent, the candidate anti-cancer agent is selected for further development as a therapeutic agent for cancer treatment.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

Phosphofructokinase 1 (PFK-1)
SEQ ID NO: 1
MAAVDLEKLRASGAGKAIGVLTSGGDAQGMNAAVRAVTRMGIYVGAK

VFLIYEGYEGLVEGGENIKQANWLSVSNIIQLGGTIIGSARCKAFTT

REGRRAAAYNLVQHGITNLCVIGGDGSLTGANIFRSEWGSLLEELVA
EGKISETTARTYSHLNIAGLVGSIDNDFCGTDMTIGTDSALHRIMEV
IDAITTTAQSHQRTFVLEVMGRHCGYLALVSALASGADWLFIPEAPP
EDGWENFMCERLGETRSRGSRLNIIIIAEGAIDRNGKPISSSYVKDL
VVQRLGFDTRVTVLGHVQRGGTPSAFDRILSSKMGMEAVMALLEATP
DTPACVVTLSGNQSVRLPLMECVQMTKEVQKAMDDKRFDEATQLRGG
SFENNWNIYKLLAHQKPPKEKSNFSLAILNVGAPAAGMNAAVRSAVR
TGISHGHTVYVVHDGFEGLAKGQVQEVGWHDVAGWLGRGGSMLGTKR
TLPKGQLESIVENIRIYGIHALLVVGGFEAYEGVLQLVEARGRYEEL
CIVMCVIPATISNNVPGTDFSLGSDTAVNAAMESCDRIKQSASGTKR
RVFIVETMGGYCGYLATVTGIAVGADAAYVFEDPFNIHDLKVNVEHM
TEKMKTDIQRGLVLRNEKCHDYYTTEFLYNLYSSEGKGVFDCRTNVL
GHLQQGGAPTPFDRNYGTKLGVKAMLWLSEKLREVYRKGRVFANAPD
SACVIGLKKKAVAFSPVTELKKDTDFEHRMPREQWWLSLRLMLKMLA
QYRISMAAYVSGELEHVTRRTLSMDKGF phosphofructokinase 1 (PFK-1) S529A
SEQ ID NO: 2
MAAVDLEKLRASGAGKAIGVLTSGGDAQGMNAAVRAVTRMGIYVGAK
VFLIYEGYEGLVEGGENIKQANWLSVSNIIQLGGTIIGSARCKAFTT
REGRRAAAYNLVQHGITNLCVIGGDGSLTGANIFRSEWGSLLEELVA
EGKISETTARTYSHLNIAGLVGSIDNDFCGTDMTIGTDSALHRIMEV
IDAITTTAQSHQRTFVLEVMGRHCGYLALVSALASGADWLFIPEAPP
EDGWENFMCERLGETRSRGSRLNIIIIAEGAIDRNGKPISSSYVKDL
VVQRLGFDTRVTVLGHVQRGGTPSAFDRILSSKMGMEAVMALLEATP
DTPACVVTLSGNQSVRLPLMECVQMTKEVQKAMDDKRFDEATQLRGG
SFENNWNIYKLLAHQKPPKEKSNFSLAILNVGAPAAGMNAAVRSAVR
TGISHGHTVYVVHDGFEGLAKGQVQEVGWHDVAGWLGRGGSMLGTKR
TLPKGQLESIVENIRIYGIHALLVVGGFEAYEGVLQLVEARGRYEEL
CIVMCVIPATIANNVPGTDFSLGSDTAVNAAMESCDRIKQSASGTKR
RVFIVETMGGYCGYLATVTGIAVGADAAYVFEDPFNIHDLKVNVEHM
TEKMKTDIQRGLVLRNEKCHDYYTTEFLYNLYSSEGKGVFDCRTNVL
GHLQQGGAPTPFDRNYGTKLGVKAMLWLSEKLREVYRKGRVFANAPD
SACVIGLKKKAVAFSPVTELKKDTDFEHRMPREQWWLSLRLMLKMLA
QYRISMAAYVSGELEHVTRRTLSMDKGF Phosphofructokinase 1 (PFK-1) nucleic
acid sequence
SEQ ID NO: 3
ATGGCCGCGGTGGACCTGGAGAAGCTGCGGGCGTCGGGCGCGGGCAA
GGCCATCGGCGTCCTGACCAGCGGCGGCGACGCGCAAGGCATGAACG
CTGCTGTCCGGGCTGTGACGCGCATGGGCATTTATGTGGGTGCCAAA
GTCTTCCTCATCTACGAGGGCTATGAGGGCCTCGTGGAGGGAGGTGA
GAACATCAAGCAGGCCAACTGGCTGAGCGTCTCCAACATCATCCAGC
TGGGCGGCACTATCATTGGCAGCGCTCGCTGCAAGGCCTTTACCACC
AGGGAGGGGCGCCGGGCAGCGGCCTACAACCTGGTCCAGCACGGCAT
CACCAACCTGTGCGTCATCGGCGGGGATGGCAGCCTTACAGGTGCCA
ACATCTTCCGCAGCGAGTGGGGCAGCCTGCTGGAGGAGCTGGTGGCG
GAAGGTAAGATCTCAGAGACTACAGCCCGGACCTACTCGCACCTGAA
CATCGCGGGCCTAGTGGGCTCCATCGATAACGACTTCTGCGGCACCG
ACATGACCATCGGCACGGACTCGGCCCTCCACCGCATCATGGAGGTC
ATCGATGCCATCACCACCACTGCCCAGAGCCACCAGAGGACCTTCGT
GCTGGAAGTGATGGGCCGGCACTGCGGGTACCTGGCGCTGGTATCTG
CACTGGCCTCAGGGGCCGACTGGCTGTTCATCCCCGAGGCTCCACCC
GAGGACGGCTGGGAGAACTTCATGTGTGAGAGGCTGGGTGAGACTCG
GAGCCGTGGGTCCCGACTGAACATCATCATCATCGCTGAGGGTGCCA
TTGACCGCAACGGGAAGCCCATCTCGTCCAGCTACGTGAAGGACCTG
GTGGTTCAGAGGCTGGGCTTCGACACCCGTGTAACTGTGCTGGGCCA
CGTGCAGCGGGGAGGGACGCCCTCTGCCTTCGACCGGATCCTGAGCA
GCAAGATGGGCATGGAGGCGGTGATGGCGCTGCTGGAAGCCACGCCT
GACACGCCGGCCTGCGTGGTCACCCTCTCGGGGAACCAGTCAGTGCG
GCTGCCCCTCATGGAGTGCGTGCAGATGACCAAGGAAGTGCAGAAAG
CCATGGATGACAAGAGGTTTGACGAGGCCACCCAGCTCCGTGGTGGG
AGCTTCGAGAACAACTGGAACATTTACAAGCTCCTGCCCCACCAGAA
GCCCCCCAAGGAGAAGTCTAACTTCTCCCTGGCCATCCTGAATGTGG
GGGCCCCGGCGGCTGGCATGAATGCGGCCGTGCGCTCGGCGGTGCGG
ACCGGCATCTCCCATGGACACACAGTATACGTGGTGCACGATGGCTT
CGAAGGCCTAGCCAAGGGTCAGGTGCAAGAAGTAGGCTGGCACGACG
TGGCCGGCTGGTTGGGGCGTGGTGGCTCCATGCTGGGGACCAAGAGG
ACCCTGCCCAAGGGCCAGCTGGAGTCCATTGTGGAGAACATCCGCAT
CTATGGTATTCACGCCCTGCTGGTGGTCGGTGGGTTTGAGGCCTATG
AAGGGGTGCTGCAGCTGGTGGAGGCTCGCGGGCGCTACGAGGAGCTC
TGCATCGTCATGTGTGTCATCCCAGCCACCATCAGCAACAACGTCCC
TGGCACCGACTTCAGCCTGGGCTCCGACACTGCTGTAAATGCCGCCA
TGGAGAGCTGTGACCGCATCAAACAGTCTGCCTCGGGGACCAAGCGC
CGTGTGTTCATCGTGGAGACCATGGGGGGTTACTGTGGCTACCTGGC
CACCGTGACTGGCATTGCTGTGGGGGCCGACGCCGCCTACGTCTTCG
AGGACCCTTTCAACATCCACGACTTAAAGGTCAACGTGGAGCACATG
ACGGAGAAGATGAAGACAGACATTCAGAGGGGCCTGGTGCTGCGGAA
CGAGAAGTGCCATGACTACTACACCACGGAGTTCCTGTACAACCTGT
ACTCATCAGAGGGCAAGGGCGTCTTCGACTGCAGGACCAATGTCCTG
GGCCACCTGCAGCAGGGTGGCGCTCCAACCCCCTTTGACCGGAACTA
TGGGACCAAGCTGGGGGTGAAGGCCATGCTGTGGTTGTCGGAGAAGC
TGCGCGAGGTTTACCGCAAGGGACGGGTGTTCGCCAATGCCCCAGAC
TCGGCCTGCGTGATCGGCCTGAAGAAGAAGGCGGTGGCCTTCAGCCC -continued

CGTCACTGAGCTCAAGAAAGACACTGATTTCGAGCACCGCATGCCAC

GGGAGCAGTGGTGGCTGAGCCTGCGGCTCATGCTGAAGATGCTGGCA

-continued

CAATACCGCATCAGTATGGCCGCCTACGTGTCAGGGGAGCTGGAGCA

CGTGACCCGCCGCACCCTGAGCATGGACAAGGGCTTC

---

What is claimed is:

1. An anti-glycosylated phosphofructokinase 1 (PFK-1) antibody that binds specifically to an endogenous glycosylated PFK-1 with an affinity that is 2 or more fold greater as compared to an affinity to a non-glycosylated PFK-1, and wherein the antibody binds a PFK-1 epitope comprising glycosylated serine 529 of PFK-1.

2. The antibody of claim 1, wherein the antibody is a monoclonal antibody.

3. The antibody of claim 1, wherein the antibody is a humanized antibody.

4. The antibody of claim 1, wherein the antibody is a human antibody.

5. The antibody of claim 1, wherein the antibody comprises a detectable label.

6. A kit for detecting glycosylated phosphofructokinase 1 (PFK-1) in a cancer tissue comprising:

(a) an anti-glycosylated phosphofructokinase 1 (PFK-1) antibody or a fragment thereof that binds specifically to an endogenous glycosylated PFK-1 with an affinity that is 2 or more fold greater as compared to an affinity to a non-glycosylated PFK-1, and wherein the antibody binds a PFK-1 epitope comprising glycosylated serine 529 of PFK-1; and
(b) instructions for use of the antibody or antigen-binding antibody fragment thereof.

7. The kit of claim 6, wherein the antibody is a monoclonal antibody.

8. The kit of claim 6, wherein the antibody is a humanized antibody.

9. The kit of claim 6, wherein the antibody is a human antibody.

* * * * *

SEQUENCE LISTING

<160> NUMBER OF SEQ ID NOS: 19

<210> SEQ ID NO 1
<211> LENGTH: 780
<212> TYPE: PRT
<213> ORGANISM: Homo sapiens

<400> SEQUENCE: 1

```
Met Ala Ala Val Asp Leu Glu Lys Leu Arg Ala Ser Gly Ala Gly Lys
1               5                   10                  15

Ala Ile Gly Val Leu Thr Ser Gly Gly Asp Ala Gln Gly Met Asn Ala
            20                  25                  30

Ala Val Arg Ala Val Thr Arg Met Gly Ile Tyr Val Gly Ala Lys Val
        35                  40                  45

Phe Leu Ile Tyr Glu Gly Tyr Glu Gly Leu Val Glu Gly Gly Glu Asn
    50                  55                  60

Ile Lys Gln Ala Asn Trp Leu Ser Val Ser Asn Ile Ile Gln Leu Gly
65                  70                  75                  80

Gly Thr Ile Ile Gly Ser Ala Arg Cys Lys Ala Phe Thr Thr Arg Glu
                85                  90                  95

Gly Arg Arg Ala Ala Ala Tyr Asn Leu Val Gln His Gly Ile Thr Asn
            100                 105                 110

Leu Cys Val Ile Gly Gly Asp Gly Ser Leu Thr Gly Ala Asn Ile Phe
        115                 120                 125

Arg Ser Glu Trp Gly Ser Leu Leu Glu Glu Leu Val Ala Glu Gly Lys
    130                 135                 140

Ile Ser Glu Thr Thr Ala Arg Thr Tyr Ser His Leu Asn Ile Ala Gly
145                 150                 155                 160

Leu Val Gly Ser Ile Asp Asn Asp Phe Cys Gly Thr Asp Met Thr Ile
                165                 170                 175

Gly Thr Asp Ser Ala Leu His Arg Ile Met Glu Val Ile Asp Ala Ile
            180                 185                 190

Thr Thr Thr Ala Gln Ser His Gln Arg Thr Phe Val Leu Glu Val Met
        195                 200                 205

Gly Arg His Cys Gly Tyr Leu Ala Leu Val Ser Ala Leu Ala Ser Gly
    210                 215                 220

Ala Asp Trp Leu Phe Ile Pro Glu Ala Pro Glu Asp Gly Trp Glu
225                 230                 235                 240

Asn Phe Met Cys Glu Arg Leu Gly Glu Thr Arg Ser Arg Gly Ser Arg
                245                 250                 255

Leu Asn Ile Ile Ile Ile Ala Glu Gly Ala Ile Asp Arg Asn Gly Lys
            260                 265                 270

Pro Ile Ser Ser Ser Tyr Val Lys Asp Leu Val Val Gln Arg Leu Gly
        275                 280                 285

Phe Asp Thr Arg Val Thr Val Leu Gly His Val Gln Arg Gly Gly Thr
    290                 295                 300

Pro Ser Ala Phe Asp Arg Ile Leu Ser Ser Lys Met Gly Met Glu Ala
305                 310                 315                 320

Val Met Ala Leu Leu Glu Ala Thr Pro Asp Thr Pro Ala Cys Val Val
```

```
                     325                 330                 335
Thr Leu Ser Gly Asn Gln Ser Val Arg Leu Pro Leu Met Glu Cys Val
                340                 345                 350
Gln Met Thr Lys Glu Val Gln Lys Ala Met Asp Asp Lys Arg Phe Asp
                355                 360                 365
Glu Ala Thr Gln Leu Arg Gly Gly Ser Phe Glu Asn Asn Trp Asn Ile
                370                 375                 380
Tyr Lys Leu Leu Ala His Gln Lys Pro Pro Lys Glu Lys Ser Asn Phe
385                 390                 395                 400
Ser Leu Ala Ile Leu Asn Val Gly Ala Pro Ala Gly Met Asn Ala
                405                 410                 415
Ala Val Arg Ser Ala Val Arg Thr Gly Ile Ser His Gly His Thr Val
                420                 425                 430
Tyr Val Val His Asp Gly Phe Glu Gly Leu Ala Lys Gly Gln Val Gln
                435                 440                 445
Glu Val Gly Trp His Asp Val Ala Gly Trp Leu Gly Arg Gly Gly Ser
                450                 455                 460
Met Leu Gly Thr Lys Arg Thr Leu Pro Lys Gly Gln Leu Glu Ser Ile
465                 470                 475                 480
Val Glu Asn Ile Arg Ile Tyr Gly Ile His Ala Leu Leu Val Val Gly
                485                 490                 495
Gly Phe Glu Ala Tyr Glu Gly Val Leu Gln Leu Val Glu Ala Arg Gly
                500                 505                 510
Arg Tyr Glu Glu Leu Cys Ile Val Met Cys Val Ile Pro Ala Thr Ile
                515                 520                 525
Ser Asn Asn Val Pro Gly Thr Asp Phe Ser Leu Gly Ser Asp Thr Ala
                530                 535                 540
Val Asn Ala Ala Met Glu Ser Cys Asp Arg Ile Lys Gln Ser Ala Ser
545                 550                 555                 560
Gly Thr Lys Arg Arg Val Phe Ile Val Glu Thr Met Gly Gly Tyr Cys
                565                 570                 575
Gly Tyr Leu Ala Thr Val Thr Gly Ile Ala Val Gly Ala Asp Ala Ala
                580                 585                 590
Tyr Val Phe Glu Asp Pro Phe Asn Ile His Asp Leu Lys Val Asn Val
                595                 600                 605
Glu His Met Thr Glu Lys Met Lys Thr Asp Ile Gln Arg Gly Leu Val
                610                 615                 620
Leu Arg Asn Glu Lys Cys His Asp Tyr Tyr Thr Thr Glu Phe Leu Tyr
625                 630                 635                 640
Asn Leu Tyr Ser Ser Glu Gly Lys Gly Val Phe Asp Cys Arg Thr Asn
                645                 650                 655
Val Leu Gly His Leu Gln Gln Gly Gly Ala Pro Thr Pro Phe Asp Arg
                660                 665                 670
Asn Tyr Gly Thr Lys Leu Gly Val Lys Ala Met Leu Trp Leu Ser Glu
                675                 680                 685
Lys Leu Arg Glu Val Tyr Arg Lys Gly Arg Val Phe Ala Asn Ala Pro
                690                 695                 700
Asp Ser Ala Cys Val Ile Gly Leu Lys Lys Lys Ala Val Ala Phe Ser
705                 710                 715                 720
Pro Val Thr Glu Leu Lys Lys Asp Thr Asp Phe Glu His Arg Met Pro
                725                 730                 735
Arg Glu Gln Trp Trp Leu Ser Leu Arg Leu Met Leu Lys Met Leu Ala
                740                 745                 750
```

```
Gln Tyr Arg Ile Ser Met Ala Ala Tyr Val Ser Gly Glu Leu Glu His
        755                 760                 765

Val Thr Arg Arg Thr Leu Ser Met Asp Lys Gly Phe
    770                 775                 780

<210> SEQ ID NO 2
<211> LENGTH: 780
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Ala Val Asp Leu Glu Lys Leu Arg Ala Ser Gly Ala Gly Lys
1               5                   10                  15

Ala Ile Gly Val Leu Thr Ser Gly Asp Ala Gln Gly Met Asn Ala
            20                  25                  30

Ala Val Arg Ala Val Thr Arg Met Gly Ile Tyr Val Gly Ala Lys Val
        35                  40                  45

Phe Leu Ile Tyr Glu Gly Tyr Glu Gly Leu Val Glu Gly Gly Glu Asn
 50                  55                  60

Ile Lys Gln Ala Asn Trp Leu Ser Val Ser Asn Ile Ile Gln Leu Gly
65                  70                  75                  80

Gly Thr Ile Ile Gly Ser Ala Arg Cys Lys Ala Phe Thr Thr Arg Glu
                85                  90                  95

Gly Arg Arg Ala Ala Ala Tyr Asn Leu Val Gln His Gly Ile Thr Asn
            100                 105                 110

Leu Cys Val Ile Gly Gly Asp Gly Ser Leu Thr Gly Ala Asn Ile Phe
        115                 120                 125

Arg Ser Glu Trp Gly Ser Leu Leu Glu Glu Leu Val Ala Glu Gly Lys
130                 135                 140

Ile Ser Glu Thr Thr Ala Arg Thr Tyr Ser His Leu Asn Ile Ala Gly
145                 150                 155                 160

Leu Val Gly Ser Ile Asp Asn Asp Phe Cys Gly Thr Asp Met Thr Ile
                165                 170                 175

Gly Thr Asp Ser Ala Leu His Arg Ile Met Glu Val Ile Asp Ala Ile
            180                 185                 190

Thr Thr Thr Ala Gln Ser His Gln Arg Thr Phe Val Leu Glu Val Met
        195                 200                 205

Gly Arg His Cys Gly Tyr Leu Ala Leu Val Ser Ala Leu Ala Ser Gly
210                 215                 220

Ala Asp Trp Leu Phe Ile Pro Glu Ala Pro Pro Glu Asp Gly Trp Glu
225                 230                 235                 240

Asn Phe Met Cys Glu Arg Leu Gly Glu Thr Arg Ser Arg Gly Ser Arg
                245                 250                 255

Leu Asn Ile Ile Ile Ala Glu Gly Ala Ile Asp Arg Asn Gly Lys
            260                 265                 270

Pro Ile Ser Ser Ser Tyr Val Lys Asp Leu Val Val Gln Arg Leu Gly
        275                 280                 285

Phe Asp Thr Arg Val Thr Val Leu Gly His Val Gln Arg Gly Gly Thr
290                 295                 300

Pro Ser Ala Phe Asp Arg Ile Leu Ser Ser Lys Met Gly Met Glu Ala
305                 310                 315                 320

Val Met Ala Leu Leu Glu Ala Thr Pro Asp Thr Pro Ala Cys Val Val
```

```
                    325                 330                 335
Thr Leu Ser Gly Asn Gln Ser Val Arg Leu Pro Leu Met Glu Cys Val
                340                 345                 350
Gln Met Thr Lys Glu Val Gln Lys Ala Met Asp Asp Lys Arg Phe Asp
                355                 360                 365
Glu Ala Thr Gln Leu Arg Gly Gly Ser Phe Glu Asn Asn Trp Asn Ile
                370                 375                 380
Tyr Lys Leu Leu Ala His Gln Lys Pro Pro Lys Glu Lys Ser Asn Phe
385                 390                 395                 400
Ser Leu Ala Ile Leu Asn Val Gly Ala Pro Ala Ala Gly Met Asn Ala
                405                 410                 415
Ala Val Arg Ser Ala Val Arg Thr Gly Ile Ser His Gly His Thr Val
                420                 425                 430
Tyr Val Val His Asp Gly Phe Glu Gly Leu Ala Lys Gly Gln Val Gln
                435                 440                 445
Glu Val Gly Trp His Asp Val Ala Gly Trp Leu Gly Arg Gly Gly Ser
                450                 455                 460
Met Leu Gly Thr Lys Arg Thr Leu Pro Lys Gly Gln Leu Glu Ser Ile
465                 470                 475                 480
Val Glu Asn Ile Arg Ile Tyr Gly Ile His Ala Leu Leu Val Val Gly
                485                 490                 495
Gly Phe Glu Ala Tyr Glu Gly Val Leu Gln Leu Val Glu Ala Arg Gly
                500                 505                 510
Arg Tyr Glu Glu Leu Cys Ile Val Met Cys Val Ile Pro Ala Thr Ile
                515                 520                 525
Ala Asn Asn Val Pro Gly Thr Asp Phe Ser Leu Gly Ser Asp Thr Ala
                530                 535                 540
Val Asn Ala Ala Met Glu Ser Cys Asp Arg Ile Lys Gln Ser Ala Ser
545                 550                 555                 560
Gly Thr Lys Arg Arg Val Phe Ile Val Glu Thr Met Gly Gly Tyr Cys
                565                 570                 575
Gly Tyr Leu Ala Thr Val Thr Gly Ile Ala Val Gly Ala Asp Ala Ala
                580                 585                 590
Tyr Val Phe Glu Asp Pro Phe Asn Ile His Asp Leu Lys Val Asn Val
                595                 600                 605
Glu His Met Thr Glu Lys Met Lys Thr Asp Ile Gln Arg Gly Leu Val
                610                 615                 620
Leu Arg Asn Glu Lys Cys His Asp Tyr Tyr Thr Thr Glu Phe Leu Tyr
625                 630                 635                 640
Asn Leu Tyr Ser Ser Glu Gly Lys Gly Val Phe Asp Cys Arg Thr Asn
                645                 650                 655
Val Leu Gly His Leu Gln Gln Gly Gly Ala Pro Thr Pro Phe Asp Arg
                660                 665                 670
Asn Tyr Gly Thr Lys Leu Gly Val Lys Ala Met Leu Trp Leu Ser Glu
                675                 680                 685
Lys Leu Arg Glu Val Tyr Arg Lys Gly Arg Val Phe Ala Asn Ala Pro
                690                 695                 700
Asp Ser Ala Cys Val Ile Gly Leu Lys Lys Lys Ala Val Ala Phe Ser
705                 710                 715                 720
Pro Val Thr Glu Leu Lys Lys Asp Thr Asp Phe Glu His Arg Met Pro
                725                 730                 735
Arg Glu Gln Trp Trp Leu Ser Leu Arg Leu Met Leu Lys Met Leu Ala
                740                 745                 750
```

Gln Tyr Arg Ile Ser Met Ala Ala Tyr Val Ser Gly Glu Leu Glu His
        755                 760                 765

Val Thr Arg Arg Thr Leu Ser Met Asp Lys Gly Phe
    770                 775                 780

<210> SEQ ID NO 3
<211> LENGTH: 2340
<212> TYPE: DNA
<213> ORGANISM: Homo sapiens

<400> SEQUENCE: 3

| | | | | | |
|---|---|---|---|---|---|
| atggccgcgg | tggacctgga | gaagctgcgg | gcgtcgggcg | cgggcaaggc | catcggcgtc | 60 |
| ctgaccagcg | gcggcgacgc | gcaaggcatg | aacgctgctg | tccgggctgt | gacgcgcatg | 120 |
| ggcatttatg | tgggtgccaa | agtcttcctc | atctacgagg | ctatgaggg | cctcgtggag | 180 |
| ggaggtgaga | acatcaagca | ggccaactgg | ctgagcgtct | ccaacatcat | ccagctgggc | 240 |
| ggcactatca | ttggcagcgc | tcgctgcaag | gcctttacca | ccaggagggg | cgccgggca | 300 |
| gcggcctaca | acctggtcca | gcacggcatc | accaacctgt | gcgtcatcgg | cggggatggc | 360 |
| agccttacag | gtgccaacat | cttccgcagc | gagtggggca | gctgctgga | ggagctggtg | 420 |
| gcggaaggta | agatctcaga | gactacagcc | cggacctact | cgcacctgaa | catcgcgggc | 480 |
| ctagtgggct | ccatcgataa | cgacttctgc | ggcaccgaca | tgaccatcgg | cacggactcg | 540 |
| gccctccacc | gcatcatgga | ggtcatcgat | gccatcacca | ccactgccca | gagccaccag | 600 |
| aggaccttcg | tgctggaagt | gatgggccgg | cactgcgggt | acctggcgct | ggtatctgca | 660 |
| ctggcctcag | gggccgactg | gctgttcatc | cccgaggctc | acccgaggga | cggctgggag | 720 |
| aacttcatgt | gtgagaggct | gggtgagact | cggagccgtg | ggtcccgact | gaacatcatc | 780 |
| atcatcgctg | agggtgccat | tgaccgcaac | gggaagccca | tctcgtccag | ctacgtgaag | 840 |
| gacctggtgg | ttcagaggct | gggcttcgac | accgtgtaa | ctgtgctggg | ccacgtgcag | 900 |
| cggggaggga | cgccctctgc | cttcgaccgg | atcctgagca | gcaagatggg | catggaggcg | 960 |
| gtgatggcgc | tgctggaagc | cacgcctgac | acgccggcct | gcgtggtcac | cctctcgggg | 1020 |
| aaccagtcag | tgcggctgcc | cctcatggag | tgcgtgcaga | tgaccaagga | agtgcagaaa | 1080 |
| gccatggatg | acaagaggtt | tgacgaggcc | acccagctcc | gtggtgggag | cttcgagaac | 1140 |
| aactggaaca | tttacaagct | cctcgcccac | cagaagcccc | caaggagaa | gtctaacttc | 1200 |
| tccctggcca | tcctgaatgt | gggggccccg | gcggctggca | tgaatgcggc | cgtgcgctcg | 1260 |
| gcggtgcgga | ccggcatctc | ccatggacac | acagtatacg | tggtgcacga | tggcttcgaa | 1320 |
| ggcctagcca | agggtcaggt | gcaagaagta | ggctggcacg | acgtggccgg | ctggttgggg | 1380 |
| cgtggtggct | ccatgctggg | gaccaagagg | accctgccca | agggccagct | ggagtccatt | 1440 |
| gtggagaaca | tccgcatcta | tggtattcac | gccctgctgg | tggtcggtgg | gtttgaggcc | 1500 |
| tatgaagggg | tgctgcagct | ggtggaggct | cgcgggcgct | acgaggagct | ctgcatcgtc | 1560 |
| atgtgtgtca | tcccagccac | catcagcaac | aacgtccctg | gcaccgactt | cagcctgggc | 1620 |
| tccgacactg | ctgtaaatgc | cgccatggag | agctgtgacc | gcatcaaaca | gtctgcctcg | 1680 |
| gggaccaagc | gccgtgtgtt | catcgtggag | accatggggg | gttactgtgg | ctacctggcc | 1740 |
| accgtgactg | gcattgctgt | ggggccgac | gccgcctacg | tcttcgagga | ccctttcaac | 1800 |
| atccacgact | taaaggtcaa | cgtggagcac | atgacgagag | agatgaagac | agacattcag | 1860 |
| agggggcctgg | tgctgcggaa | cgagaagtgc | catgactact | acaccaccgga | gttcctgtac | 1920 |

```
aacctgtact catcagaggg caagggcgtc ttcgactgca ggaccaatgt cctgggccac    1980
ctgcagcagg gtggcgctcc aaccccttt gaccggaact atgggaccaa gctggggtg     2040 aaggccatgc tgtggttgtc ggagaagctg cgcgaggttt accgcaaggg acgggtgttc    2100
gccaatgccc cagactcggc ctgcgtgatc ggcctgaaga agaaggcggt ggccttcagc    2160
cccgtcactg agctcaagaa agacactgat ttcgagcacc gcatgccacg ggagcagtgg    2220
tggctgagcc tgcggctcat gctgaagatg ctggcacaat accgcatcag tatgccgcc    2280 tacgtgtcag gggagctgga gcacgtgacc cgccgcaccc tgagcatgga caagggcttc    2340
```

<210> SEQ ID NO 4
<211> LENGTH: 4
<212> TYPE: PRT
<213> ORGANISM: Unknown
<220> FEATURE:
<223> OTHER INFORMATION: Description of Unknown: "KDEL" motif peptide

<400> SEQUENCE: 4

Lys Asp Glu Leu
1

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cctagtagga agcatcgaca a                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cctagtgggc tccatcgata a                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agtccttagt cgaatcagcc g                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccaaactttc tggatgctta t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
ttcgatctca attgctatcg a                                              21

<210> SEQ ID NO 10
<211> LENGTH: 19
<212> TYPE: PRT
<213> ORGANISM: Rattus norvegicus

<400> SEQUENCE: 10

Ile Pro Phe Val Val Ile Pro Ala Thr Val Ser Asn Asn Val Pro Gly
1               5                   10                  15

Ser Asp Phe

<210> SEQ ID NO 11
<211> LENGTH: 19
<212> TYPE: PRT
<213> ORGANISM: Mus musculus

<400> SEQUENCE: 11

Ile Val Met Cys Val Ile Pro Ala Thr Ile Ser Asn Asn Val Pro Gly
1               5                   10                  15

Thr Asp Phe

<210> SEQ ID NO 12
<211> LENGTH: 19
<212> TYPE: PRT
<213> ORGANISM: Cricetulus griseus

<400> SEQUENCE: 12

Ile Val Met Cys Val Ile Pro Ala Thr Ile Ser Asn Asn Val Pro Gly
1               5                   10                  15

Thr Asp Phe

<210> SEQ ID NO 13
<211> LENGTH: 19
<212> TYPE: PRT
<213> ORGANISM: Macaca fascicularis

<400> SEQUENCE: 13

Ile Pro Phe Val Val Ile Pro Ala Thr Val Ser Asn Asn Val Pro Gly
1               5                   10                  15

Ser Asp Phe

<210> SEQ ID NO 14
<211> LENGTH: 19
<212> TYPE: PRT
<213> ORGANISM: Pongo abelii

<400> SEQUENCE: 14

Ile Pro Phe Val Val Ile Pro Ala Thr Val Ser Asn Asn Val Pro Gly
1               5                   10                  15

Ser Asp Phe

```
<210> SEQ ID NO 15
<211> LENGTH: 19
<212> TYPE: PRT
<213> ORGANISM: Nomascus leucogenys

<400> SEQUENCE: 15

Ile Pro Phe Val Val Ile Pro Ala Thr Val Ser Asn Asn Val Pro Gly
1               5                   10                  15

Ser Asp Phe

<210> SEQ ID NO 16
<211> LENGTH: 19
<212> TYPE: PRT
<213> ORGANISM: Danio rerio

<400> SEQUENCE: 16

Ile Pro Met Val Ile Ile Pro Ala Thr Val Ser Asn Asn Val Pro Gly
1               5                   10                  15

Ser Asp Phe

<210> SEQ ID NO 17
<211> LENGTH: 19
<212> TYPE: PRT
<213> ORGANISM: Drosophila melanogaster

<400> SEQUENCE: 17

Ile Pro Ile Val Val Ile Pro Ser Thr Ile Ser Asn Asn Val Pro Gly
1               5                   10                  15

Thr Glu Phe

<210> SEQ ID NO 18
<211> LENGTH: 19
<212> TYPE: PRT
<213> ORGANISM: Saccharomyces cerevisiae

<400> SEQUENCE: 18

Ile Pro Met Cys Leu Ile Pro Ala Thr Val Ser Asn Asn Val Pro Gly
1               5                   10                  15

Thr Glu Tyr

<210> SEQ ID NO 19
<211> LENGTH: 19
<212> TYPE: PRT
<213> ORGANISM: Pichia pastoris

<400> SEQUENCE: 19

Ile Pro Met Cys Cys Leu Pro Ala Thr Val Ser Asn Asn Val Pro Gly
1               5                   10                  15

Thr Glu Tyr
```